US006783530B1

(12) United States Patent
Levy

(10) Patent No.: US 6,783,530 B1
(45) Date of Patent: *Aug. 31, 2004

(54) EXPANDABLE ORTHOPEDIC DEVICE

(75) Inventor: Mark Levy, Raanana (IL)

(73) Assignee: Expanding Orthopedics Inc., Raanana (IL)

( * ) Notice: Subject to any disclaimer, the term of this patent is extended or adjusted under 35 U.S.C. 154(b) by 126 days.

This patent is subject to a terminal disclaimer.

(21) Appl. No.: 10/111,243
(22) PCT Filed: Oct. 19, 2000
(86) PCT No.: PCT/IL00/00666
§ 371 (c)(1),
(2), (4) Date: Aug. 27, 2002
(87) PCT Pub. No.: WO01/28443
PCT Pub. Date: Apr. 26, 2001

(30) Foreign Application Priority Data

Oct. 22, 1999 (US) .......................................... 09/426,563

(51) Int. Cl.⁷ ............................................... A61B 17/56
(52) U.S. Cl. ............................. 606/63; 606/62; 606/64; 606/61
(58) Field of Search ........................... 606/200, 60, 61, 606/62, 63, 64, 65, 66, 67, 72, 73; 623/16.11, 17.11

(56) References Cited

U.S. PATENT DOCUMENTS

2002/0165544 A1 * 11/2002 Perren et al. ................. 606/63

* cited by examiner

Primary Examiner—Cary E. O'Connor
Assistant Examiner—Candice C. Melson
(74) Attorney, Agent, or Firm—Bingham McCutchen LLP

(57) ABSTRACT

An intramedullary device used to stabilize a variety of fractured bones includes a plurality of resilient spine elements. A porous interconnection structure interconnects the spine elements, such as a mesh or a plurality of struts connected between the spine elements. The device expands at one or both ends, and optionally, the shaft of the device can also expand. The end of the device, in its expanded state, has a circumference greater than a circumference of the shaft. The spine elements and/or the interconnection structure are pre-shaped, e.g., composed of a resilient material and pre-shaped, such that the end of the device expands in the absence of an external restraining force. The spine elements and/or interconnection structure can be composed of a shape memory material, such that the expandable end of the device expands when heated to a temperature above a transitional temperature of the shape memory material.

10 Claims, 29 Drawing Sheets

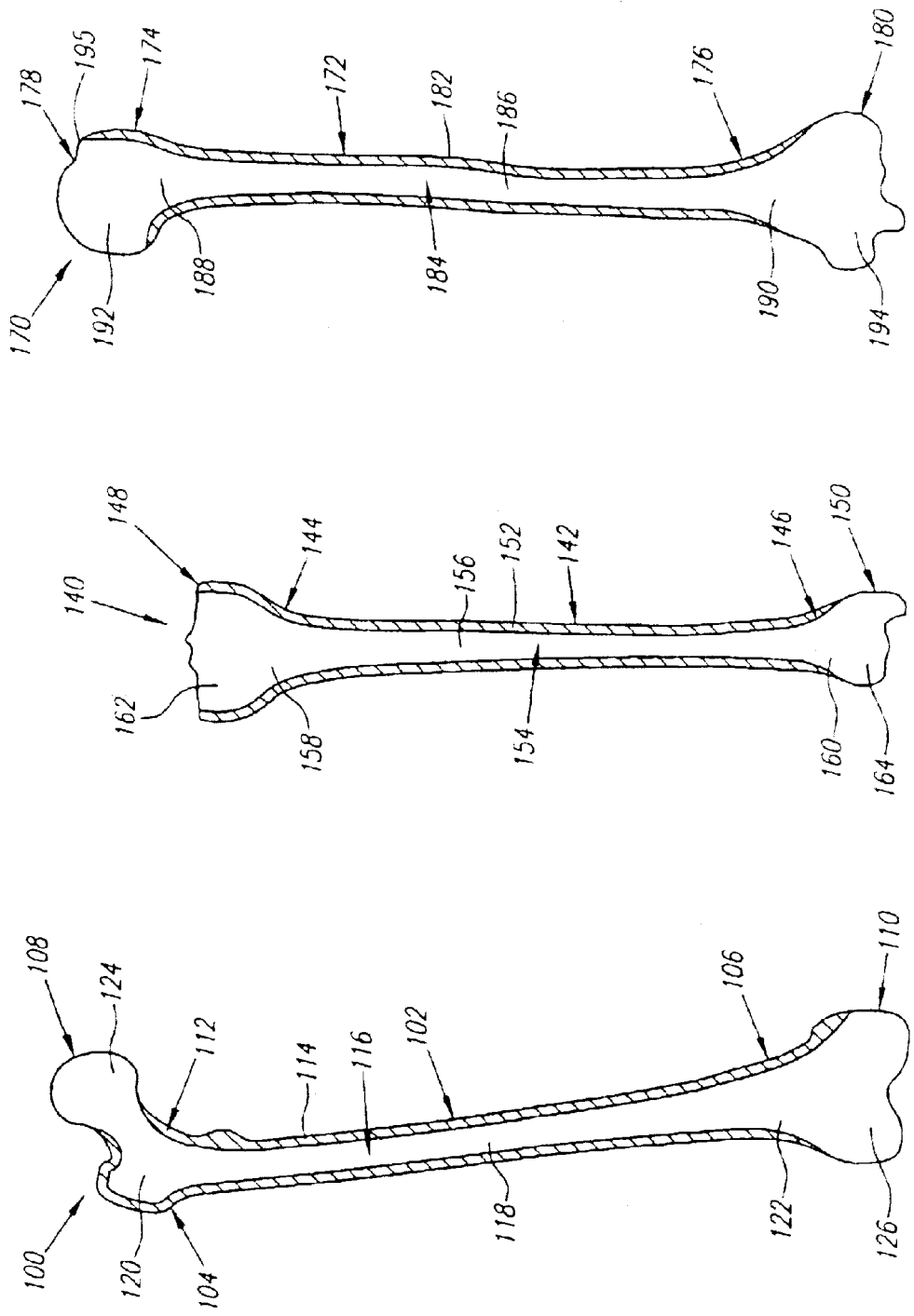

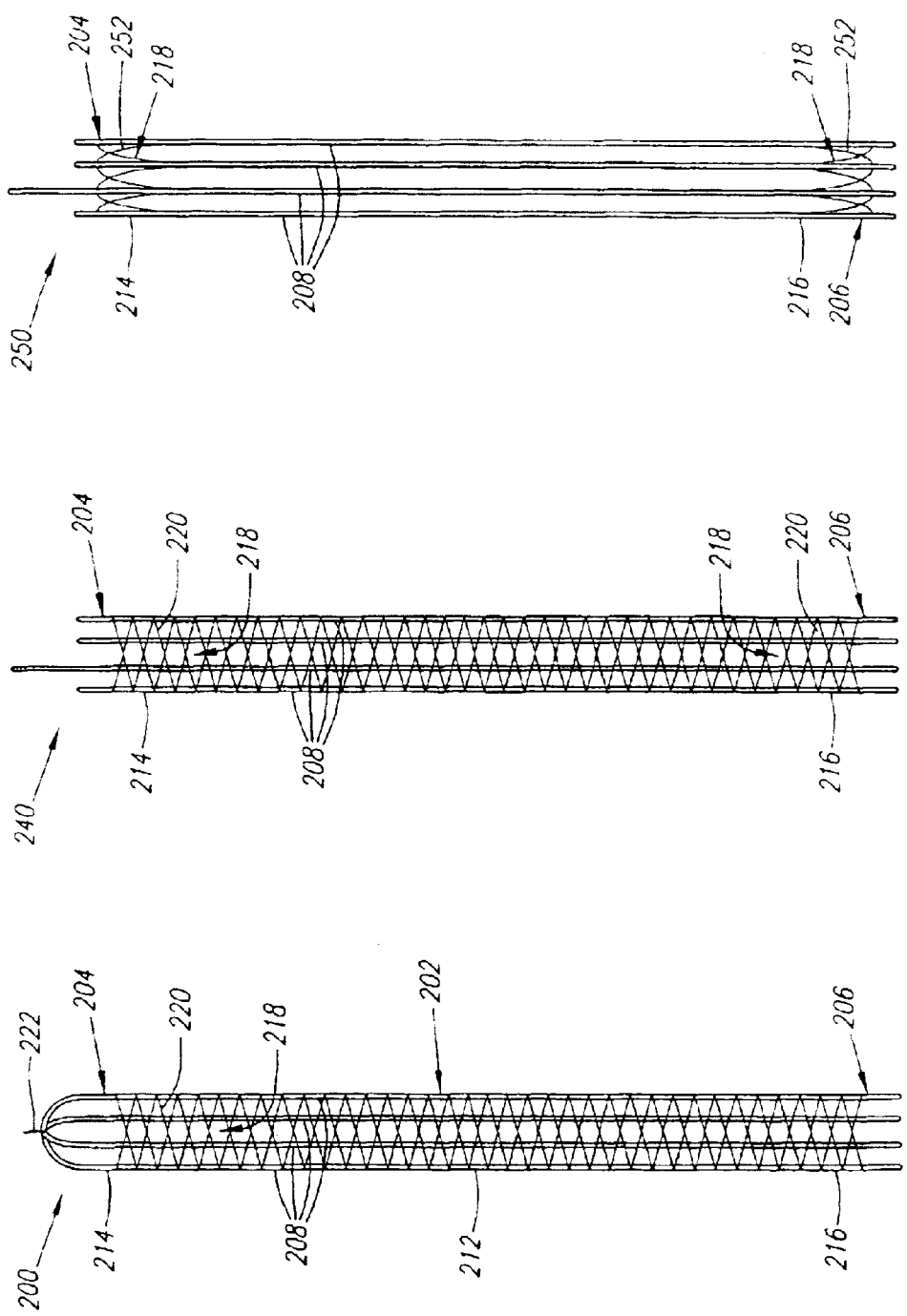

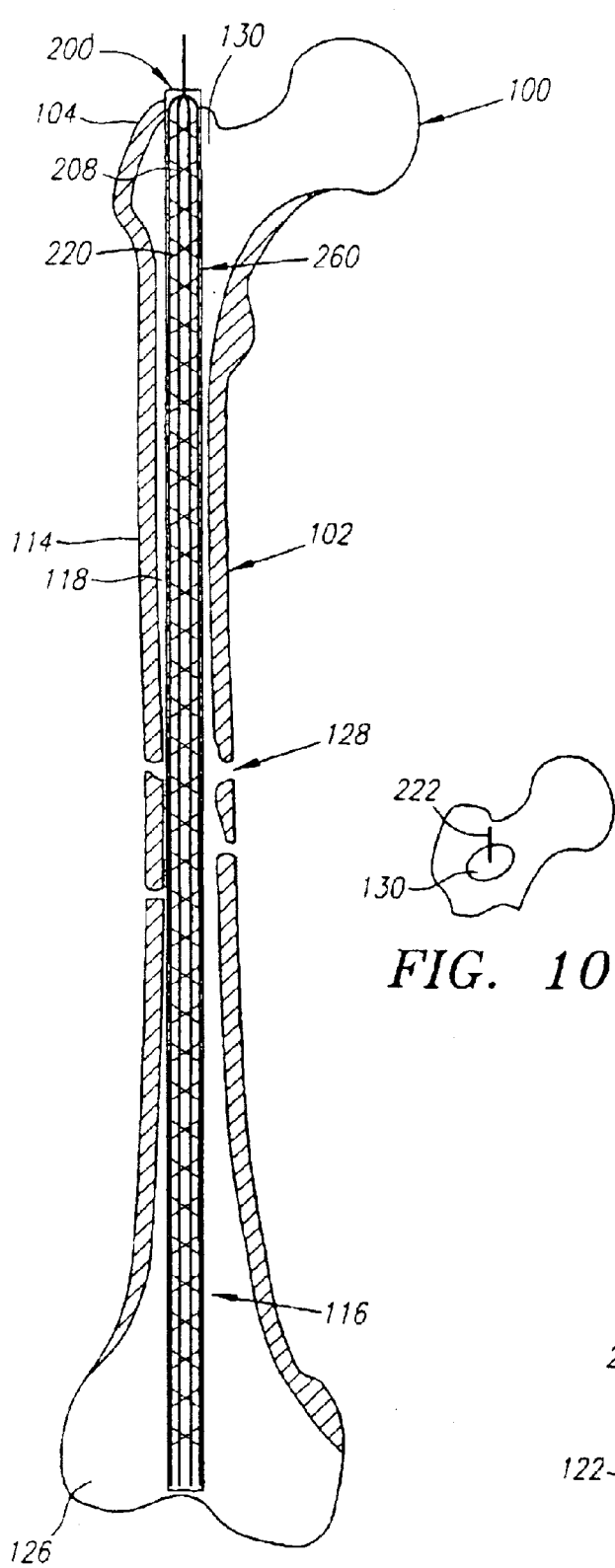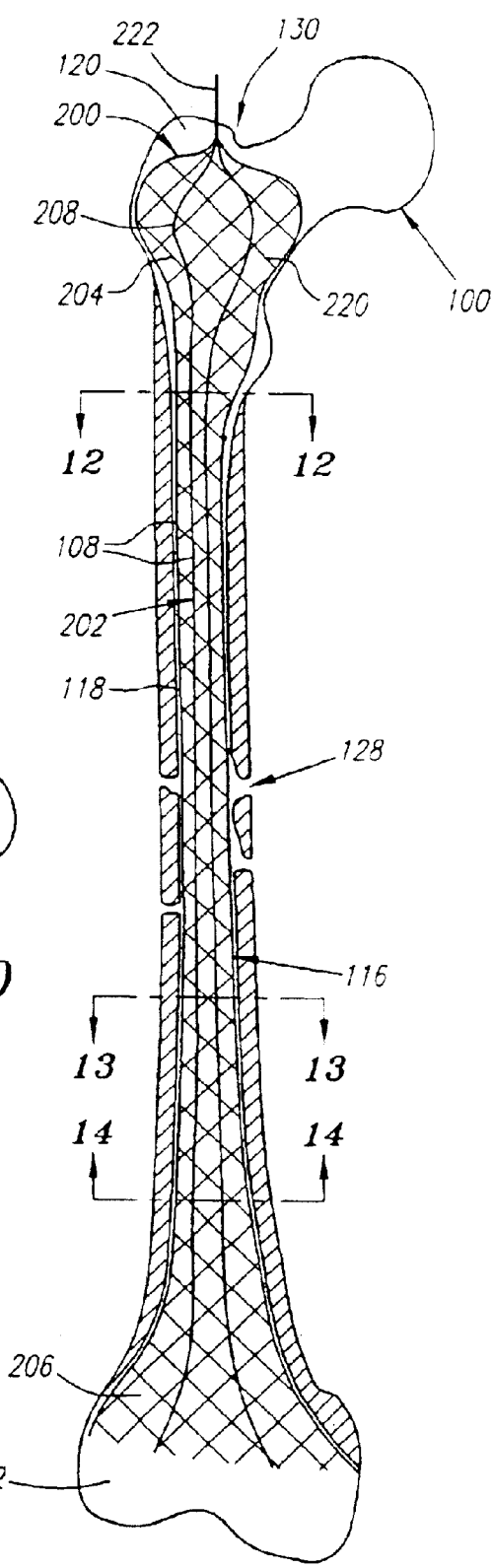
FIG. 9        FIG. 10        FIG. 11

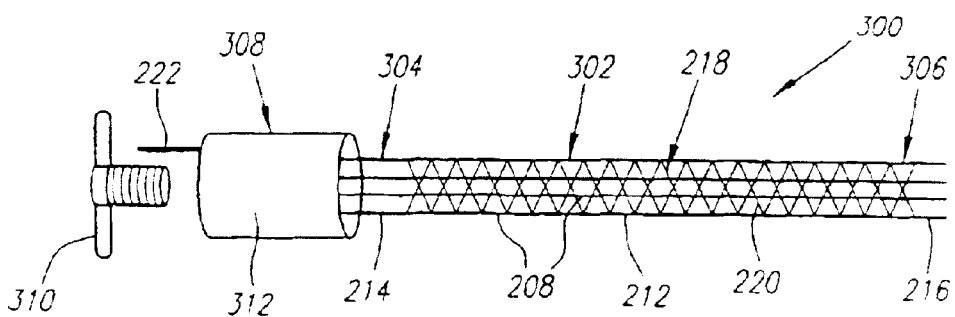
FIG. 23
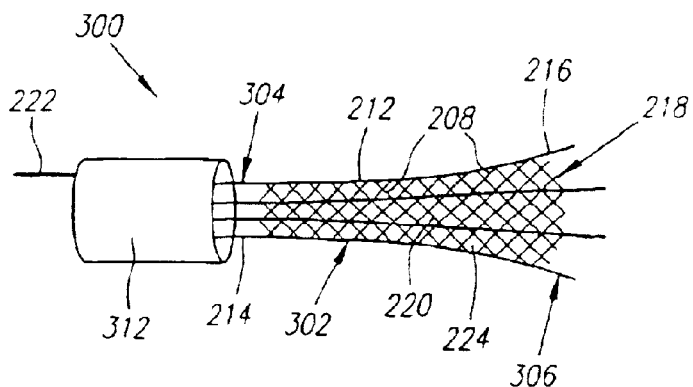
FIG. 24
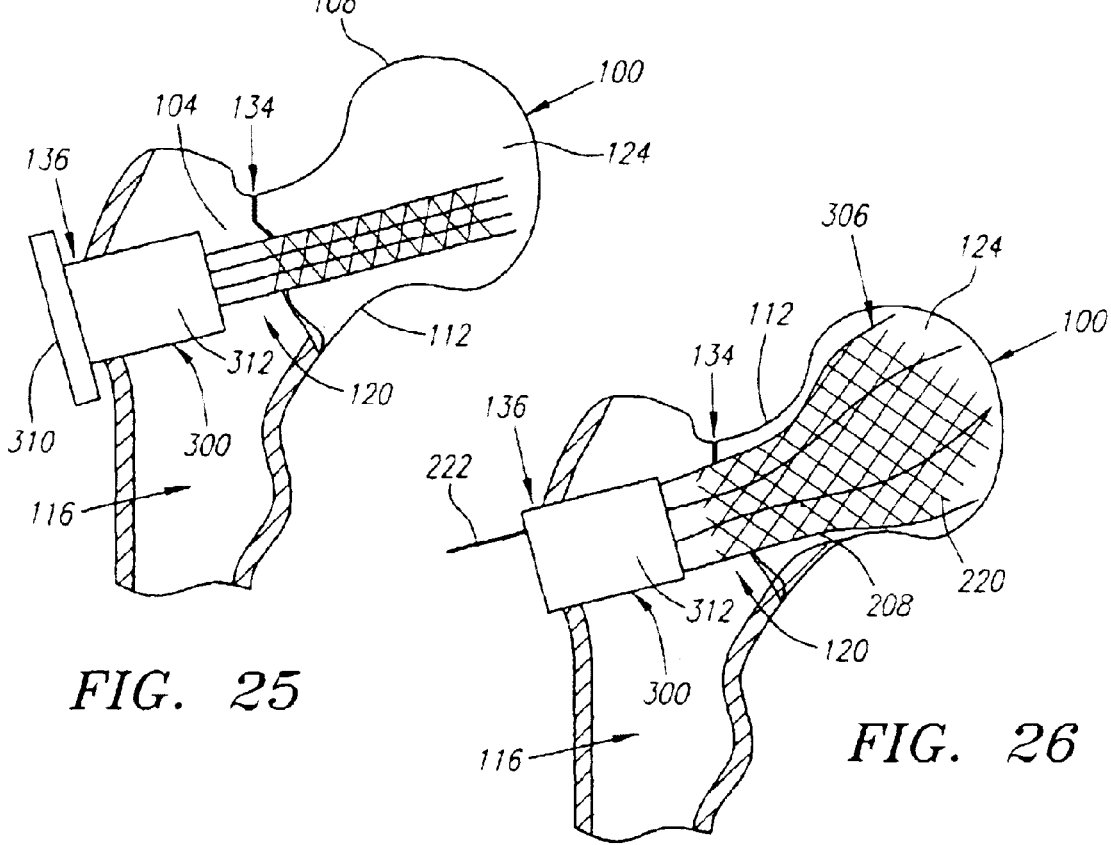
FIG. 25
FIG. 26

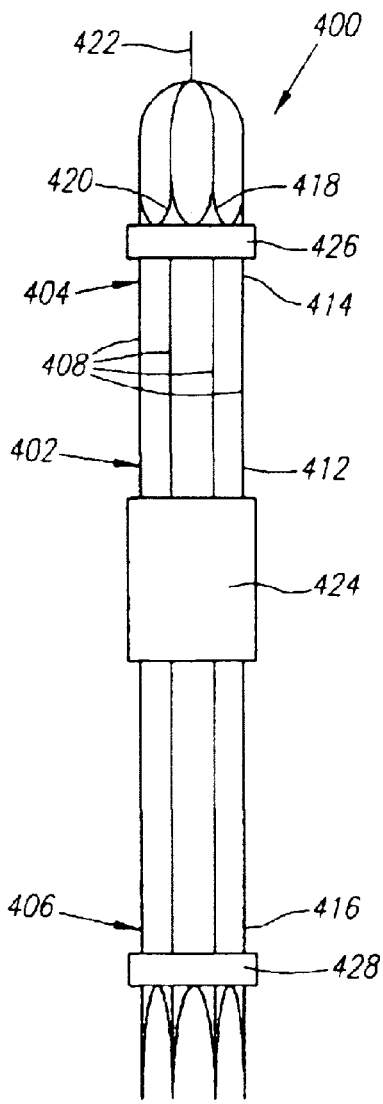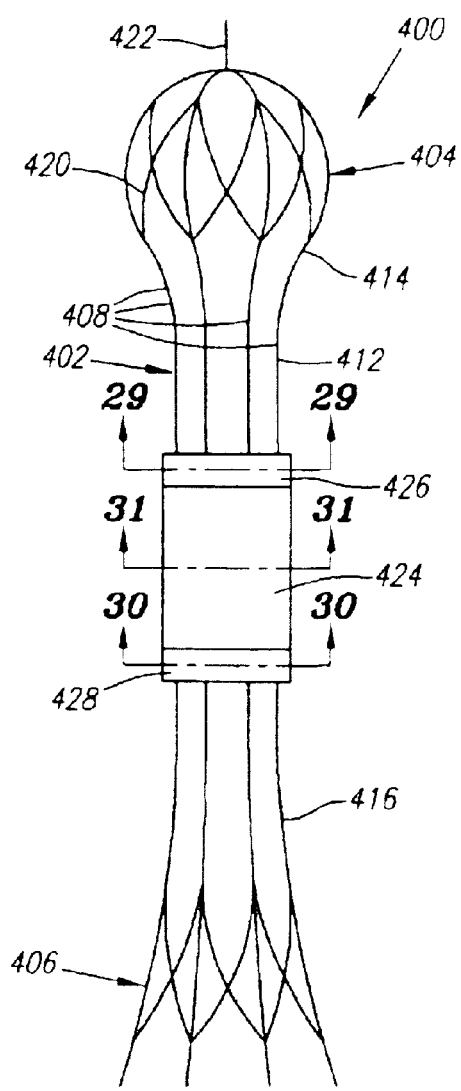
*FIG. 27*  *FIG. 28*
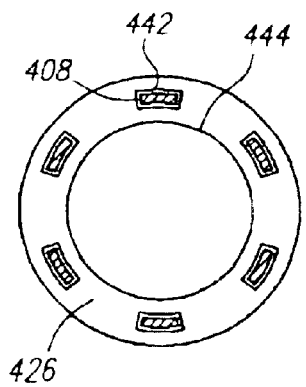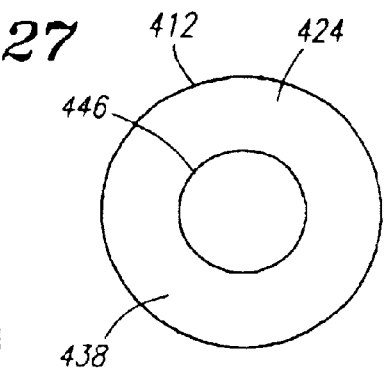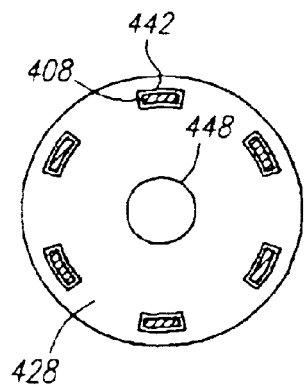
*FIG. 29*  *FIG. 31*  *FIG. 30*

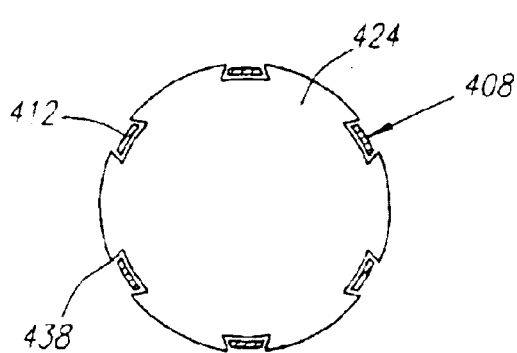
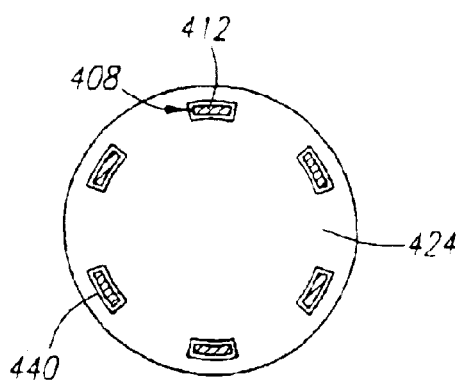
FIG. 32    FIG. 33
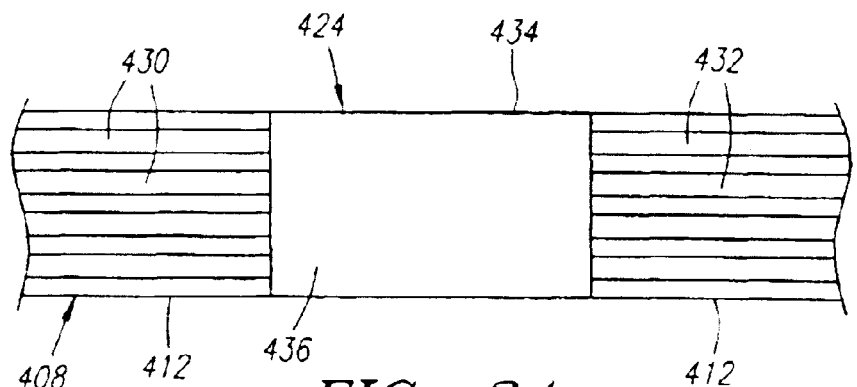
FIG. 34
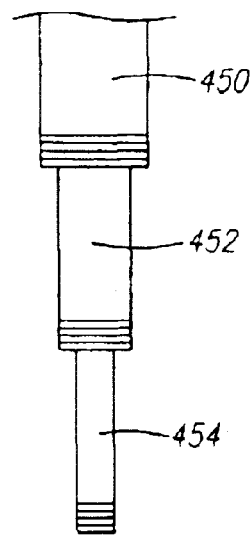
FIG. 35

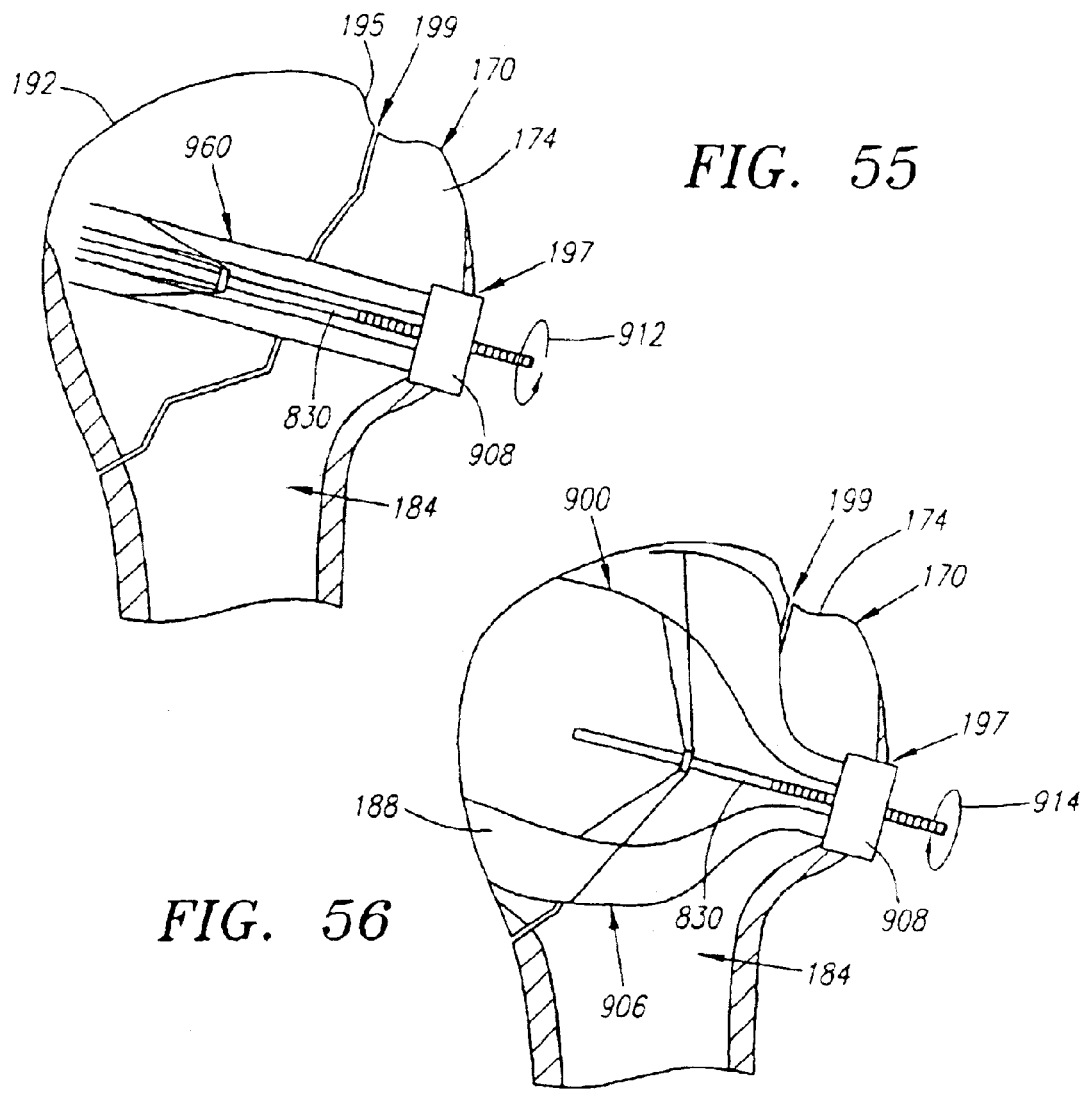
FIG. 55
FIG. 56
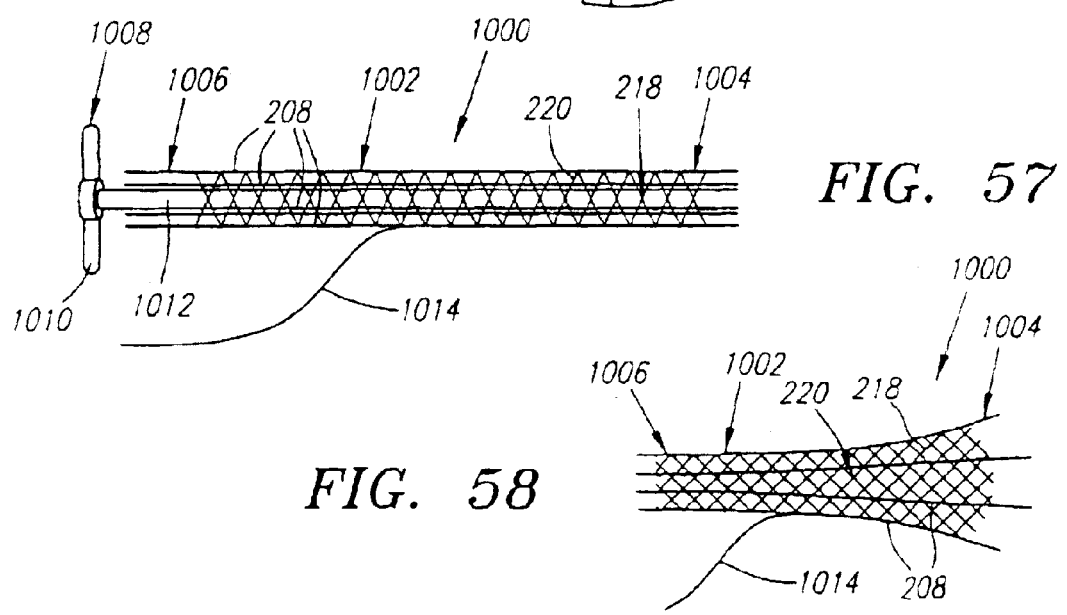
FIG. 57
FIG. 58

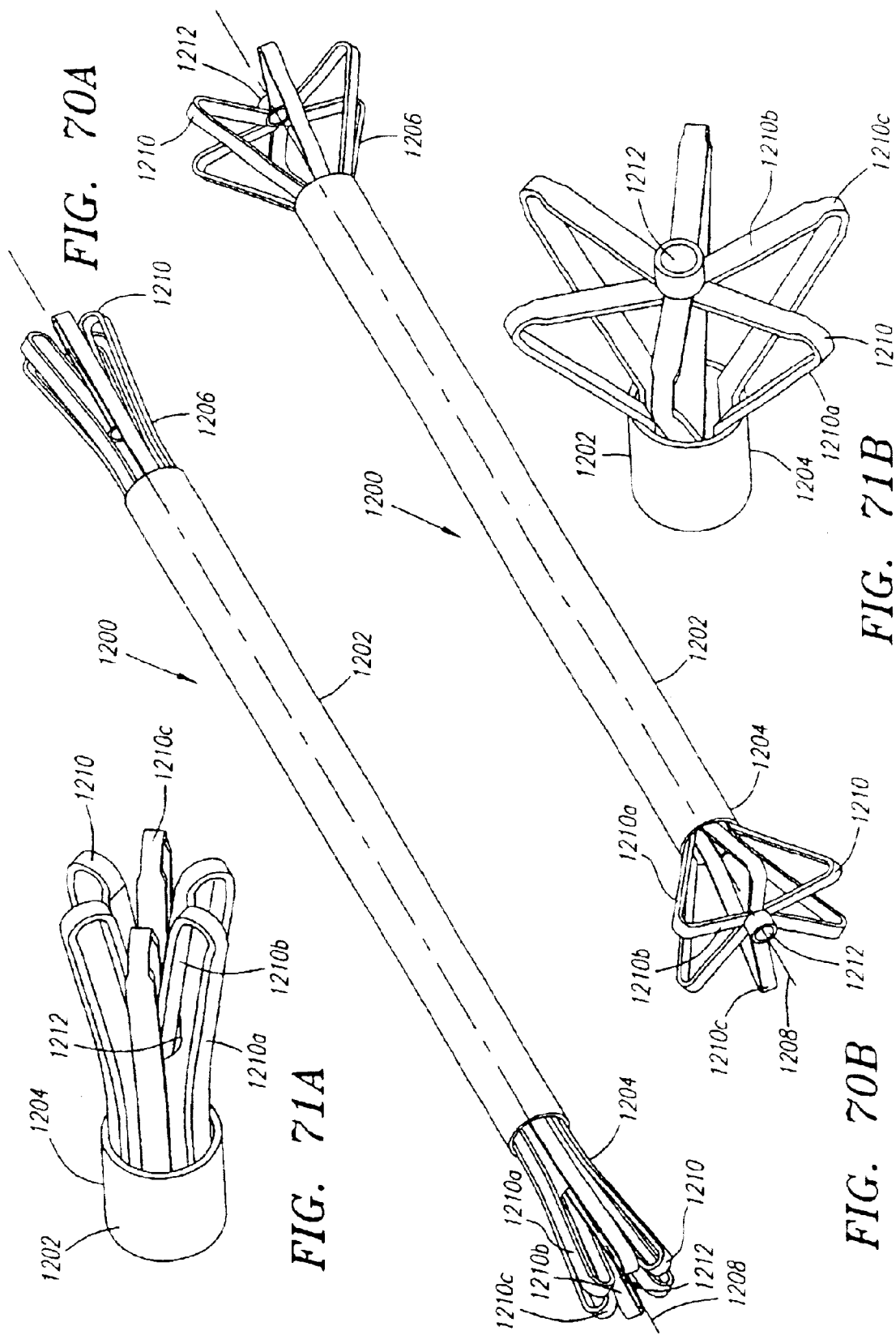

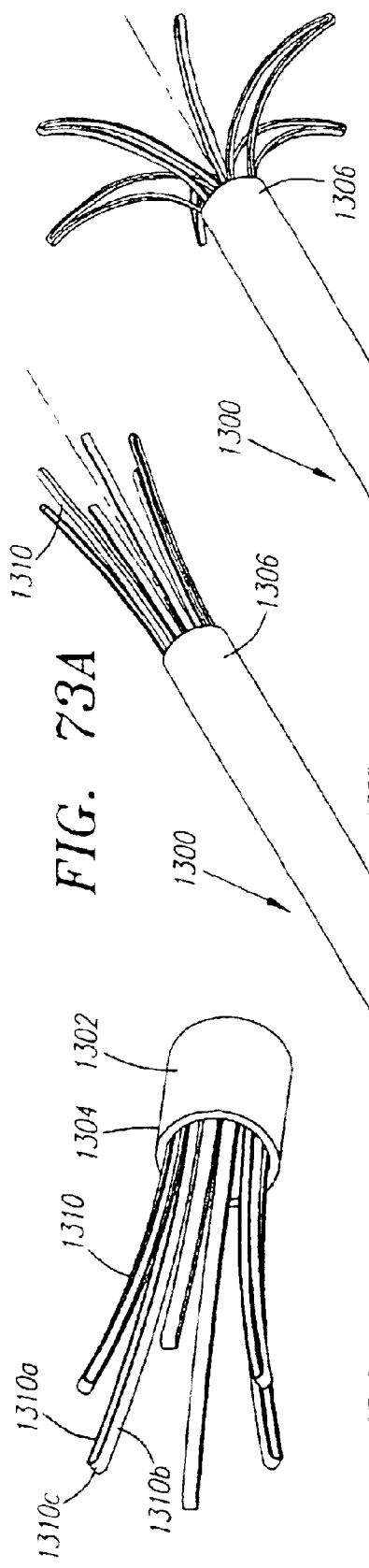
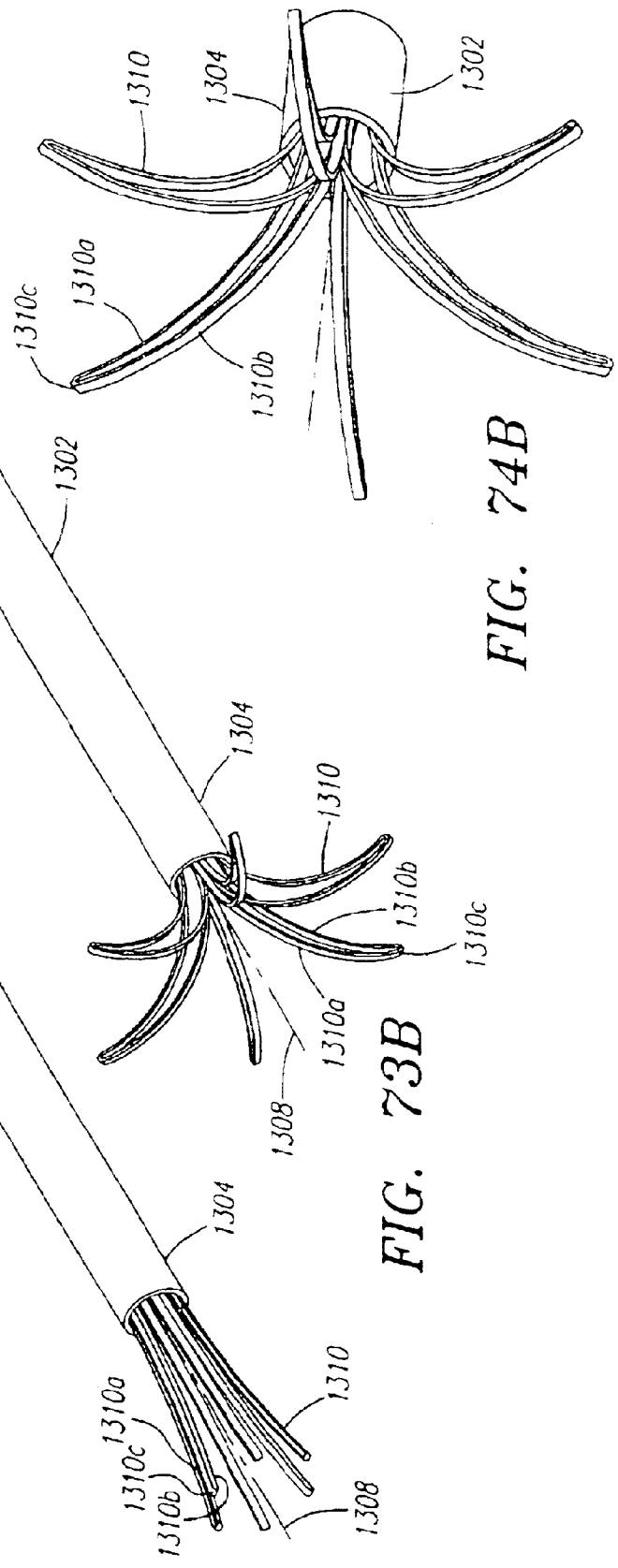

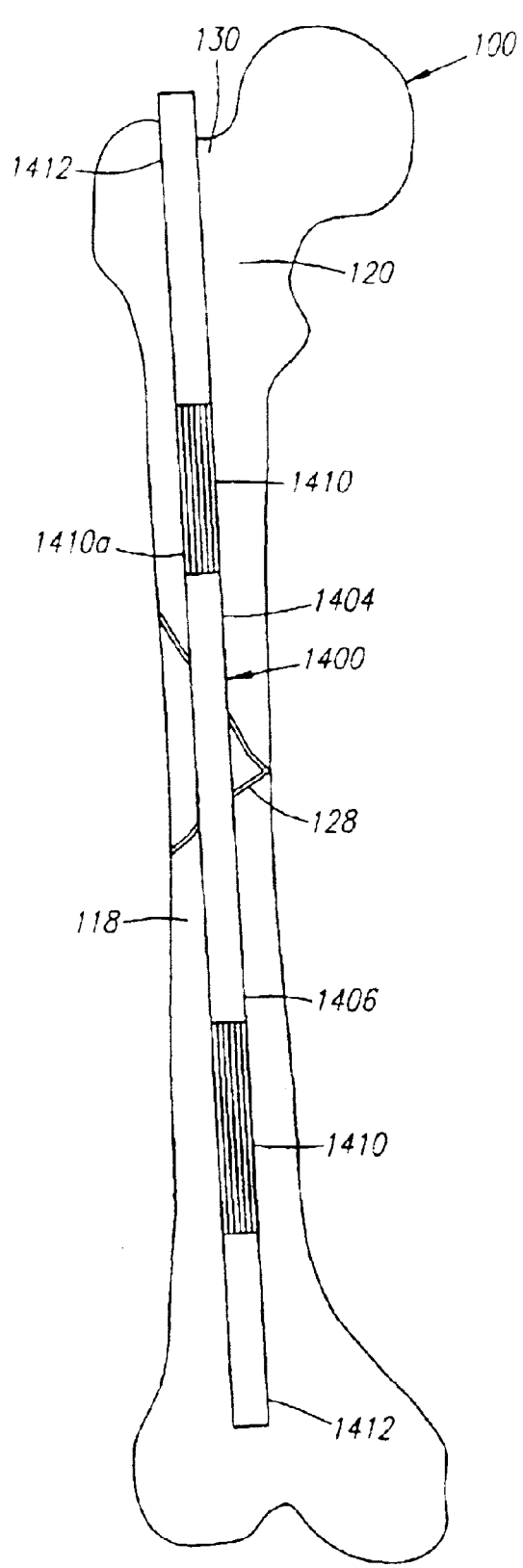
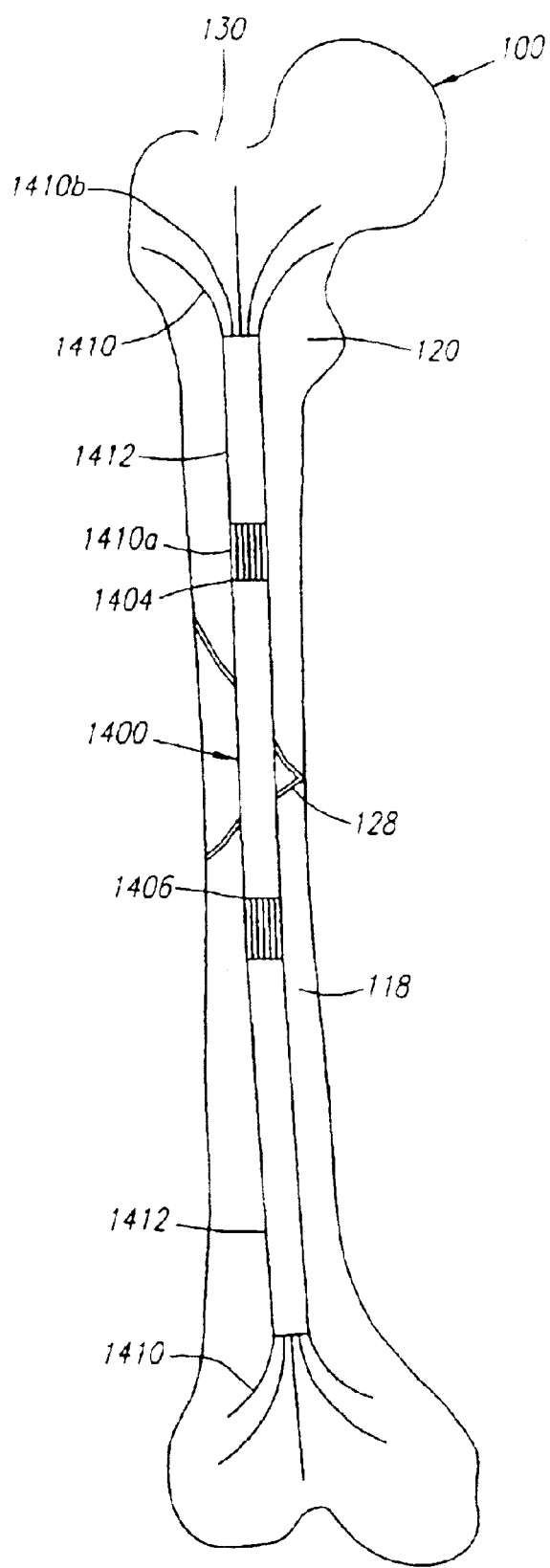
FIG. 75A
FIG. 75B

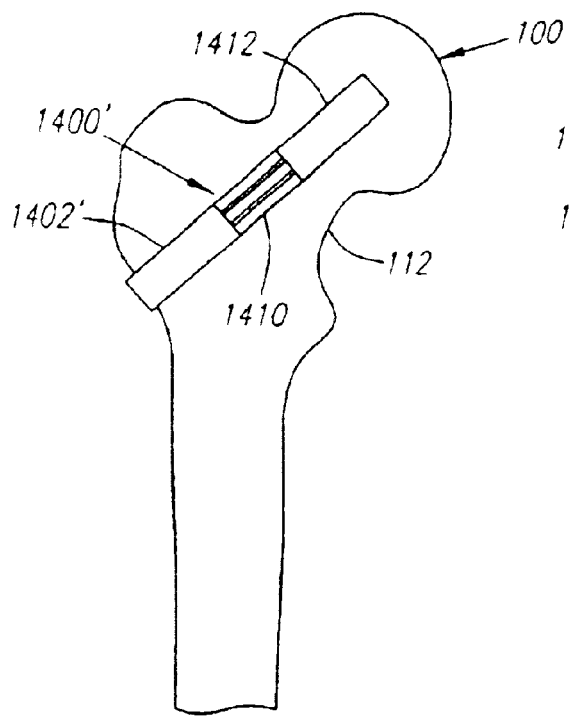
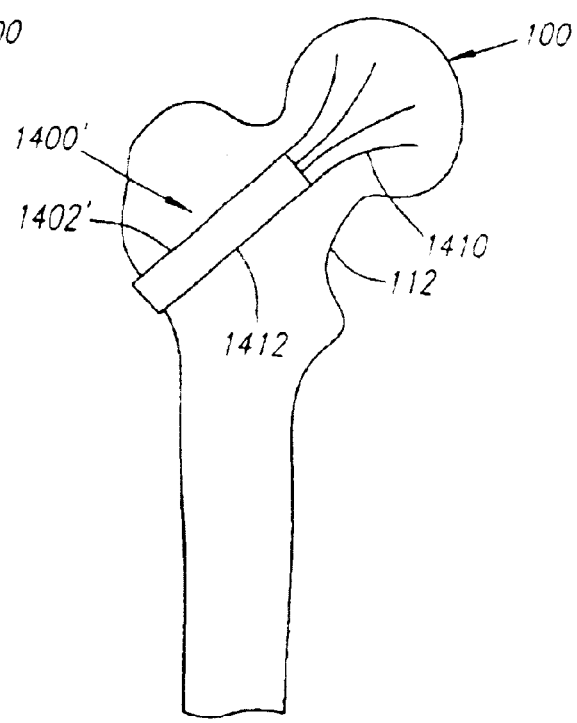
FIG. 76A
FIG. 76B
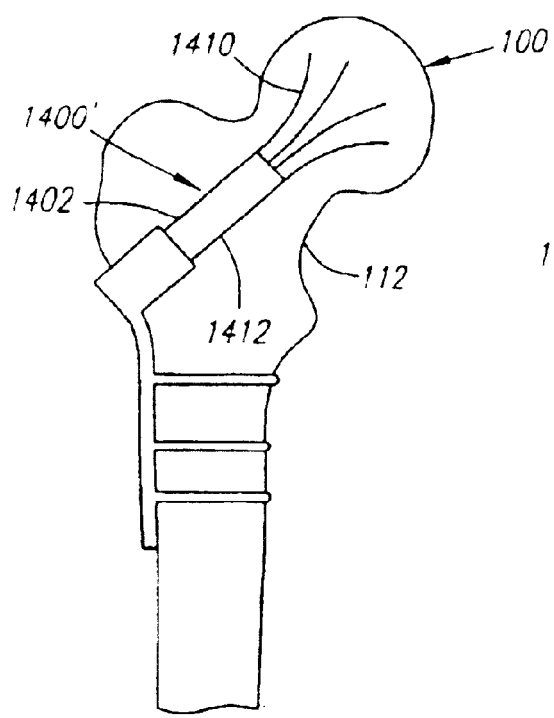
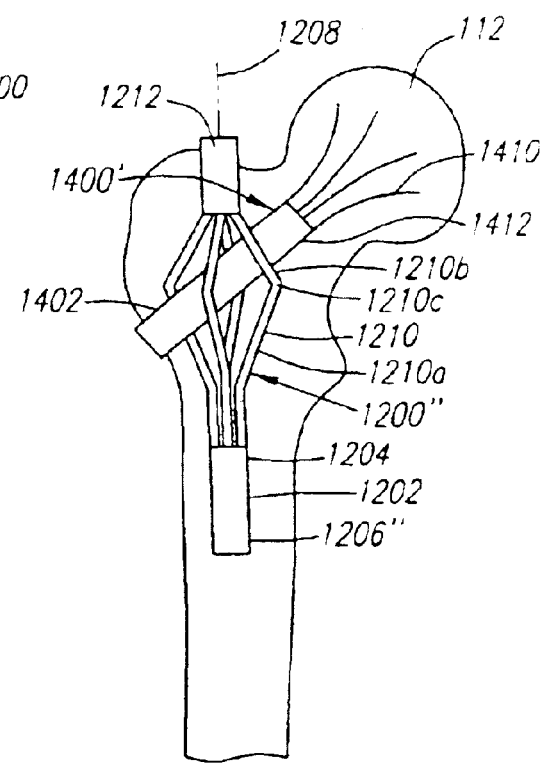
FIG. 77A
FIG. 77B

EXPANDABLE ORTHOPEDIC DEVICE

FIELD OF THE INVENTION

The present invention relates to orthopedic devices for surgical treatment of bone fractures and for the prophylactic treatment of pathological bones.

BACKGROUND OF THE INVENTION

Fractures of limb bones have been treated with internal fixation devices, such as plates lying on the surface of the bone, nails running inside the medullary canal of the fractured bone, or screws affixing both ends of a fractured bone together. Certain criteria should be satisfied when treating such bone fractures. These criteria include providing reasonable structural rigidity to the fractured bone, without compromising some of the strain desired to stimulate bone cells. This stability should be ensured along the longitudinal, transversal and rotational planes of the fractured bone. The device that provides the stability to the fractured bone should minimize disruption of blood supply within the bone, periosteally and intramedullarly. Ideally, the device should be as least invasive as possible to prevent the fracture site from opening. The device should also allow the use of the affected area as soon as possible, without compromising fracture stability. Potentially, the device should also allow for the use of drugs or hardware to locally treat or enhance the union process of the fracture site.

An intramedullary fixation method is a preferred traditional method of treatment for long bone fractures, since it adequately effects affixation of the bone fracture with the use of intramedullary nails, without disturbing the periosteum of the bone. The intramedullary fixation method can be accomplished in a closed manner, and the fractured bone can be functionally used (including weight bearing) during healing. The surgical approach for insertion of intramedullary nails varies slightly for each bone and is well described in the orthopedic literature. A detailed description is offered for the femur, tibia, humerus, radius and ulna in the Campbell textbook of Orthopedic Surgery. Also the Synthes Group, in its book, offers a well-illustrated description. The Nancy nail brochure offers an illustrative description of the elastic intramedullary nails currently recommended for fracture fixation in children.

There are problems associated with many of the intramedullary fixation methods, including the lack of rotation stability, collapse of the fracture site in some fracture types, and the undesired backup of nails. Furthermore, although the actual shape of the bone typically includes some degree of curvature, the intramedullary nails used to mend the fractured bone are typically straight. Still further, the intramedullary fixation method introduces interlocking screws across the nail, creating some disadvantages. Specifically, conventional intramedullary fixation nails for long bones include a rigid structure (hollow or full), that can be locked at their extremes by the addition of screws transversally applied through the bone walls and the nail itself. This additional step makes the operation longer and sometimes cumbersome, and may require necessary additional skin incisions and significant longer use of an image intensifier (X-ray). Furthermore, undesired gaps between the bone ends can originate from the screws, which are permanent unless removed in a new operation. Also, the resultant structure in certain situations is too stiff and lacks the required elasticity. In contaminated fractures, the intramedullary nails, which are metallic, may propagate the contamination through the entire canal, despite attempts at cleaning the fracture site. This may lead to and propagate bone infection.

Recent developments in the intramedullary fixation approach have attempted to address some of these problems. For example, International Patent No. WO 98/38918 to Beyar suggests three structural designs: (1) a solid metal sheet that expands in the medullary canal; (2) a meshwork structure consisting of ribs circumferentially connected at the tips; and (3) a balloon structure that is inflated once inserted into the medullary canal. The first two structures, however, are unable to provide firm support within the metaphysis of the bone. Specifically, these structures are unable to expand at their ends, because the total expansion of the structures is limited by the circumference of the diaphyseal segment of the medullary canal. The balloon structure also has limited utility because, when inflated, it disrupts the blood supply of the bone and avoids its regeneration or recovery, and is unable to adjust to changes in the shape of the medullary canal, because it has a set volume once inserted and inflated.

U.S. Pat. No. 5,281,225 to Vicenzi discloses a structure that includes a multitude of elastically deformable stems connected together by a stub. When inserted in the medullary canal of a fractured bone, the distal tips of the stems expand outward into the end of the medullary canal to anchor the Vicenzi structure within the bone. The stem, however, is affixed to the fractured bone via a transverse screw. Additionally, the Vicenzi structure is not expanded within the medullary canal and, thus, does not provide multiple points of contact with the wall of the medullary canal. As a result, the Vicenzi structure might not ensure structural stability along the transversal and rotational planes of the fractured bone.

Thus, it would be desirable to provide intramedullary devices that provide and ensure stability to a fractured bone, without hindering the normal biological processes within the fractured bone.

SUMMARY OF THE INVENTION

The present inventions are directed to intramedullary devices that provide and ensure stability to a fractured bone, without hindering the normal biological processes within the fractured bone.

In a first aspect of the present inventions, an intramedullary device employs a porous interconnection structure to facilitate expansion of the device. The intramedullary device includes a plurality of resilient spine elements longitudinally arranged to form a resultant structure. The resultant structure has a structural shaft, a first structural end, and a second structural end. One or both of the first and second structural ends are expandable and, when expanded, has a circumference greater than that of the structural shaft. In this manner, the expanded structural end or ends can firmly engage the walls of relatively large bone cavities, such as the metaphyseal or epiphyseal areas. The expanded structural end can be conveniently formed into various shapes, such as a bulbous- or trumpet-like shape. Additionally, the structural shaft can be made expandable, such that the expanded structural shaft can firmly engage the walls of long, relatively uniform cavities, such as the medullary canal.

The porous interconnection structure interconnects the plurality of spine elements at one or both of the expandable structural ends. If the structural shaft expands, the interconnection structure can interconnect the plurality of spine elements at the structural shaft. The interconnection structure can be advantageously used to provide further support to the spine elements, aid in the shaping of the resultant structure, when expanded, and/or actuate the expansion of the resultant structure, while minimizing any interruption of the biological processes within the fractured bone. The interconnection structure can be formed of a suitable structure, such as a mesh or struts, and can be variously connected to the spine elements. By way of non-limiting example, the interconnection structure can be disposed between the spine elements.

If the intramedullary device expands only at the first structural end, the spine elements can be affixed to a connector at the second structural end to ensure structural integrity of the intramedullary device, as well as to provide a convenient means of mounting. If the intramedullary device expands at both the first and second structural ends, the spine elements can be affixed to a connector at the structural shaft to ensure structural integrity of the intramedullary device. The length of the connector can be selected to provide more or less structure or column strength to the intramedullary device.

Any combination of the first structural end, second structural end, and structural shaft can be made to expand by pre-shaping either or both of the spine elements and interconnection structure. By way of nonlimiting example, the spine elements and/or interconnection structure can be pre-shaped, such that one or both of the structural ends, or all of the resultant structure, expands in the absence of an external restraining force. Or the spine elements and/or interconnection structure can be pre-shaped and be composed of a shape memory material, such as a shape memory alloy or polymer, having a shape transitional temperature, such that one or both of the structural ends, or all of the resultant structure, expands when heated to a temperature above the shape transitional temperature.

Optionally, either or both of the spine elements and interconnection structure can be further composed of a bioabsorbable material, such that none or only a portion of the intramedullary device need be extracted from the bone, when healed. If a second operation is needed, one of the spine elements can be advantageously made longer than the others to facilitate precise location of the intramedullary device after the entry portal through which the intramedullary device is inserted has healed over.

In a second aspect of the present inventions, an intramedullary device expands at opposite ends. The intramedullary device includes a plurality of pre-shaped spine elements longitudinally arranged to form a resultant structure. The resultant structure has a structural shaft, a first structural end, and a second structural end. Both of the first and second structural ends are expandable and, when expanded, have circumferences greater than that of the structural shaft. In this manner, the expanded structural end or ends can firmly engage the walls of relatively large bone cavities, such as the metaphyseal or epiphyseal areas. The expanded structural ends can be conveniently formed into various shapes, such as a bulbous or trumpet-like shape.

The intramedullary device further includes a connector that affixes the spine elements at the structural shaft to ensure structural integrity of the intramedullary device. The length of the connector can be selected to provide more or less structure or column strength to the intramedullary device. The connector and spine elements can be made of the same piece of material or, alternatively, can be made from separate pieces of material. The intramedullary device may optionally include a porous interconnection structure, which interconnects the plurality of spine elements at both of the expandable structural ends.

The first and second structural ends can be made to expand by pre-shaping the spine elements. For example, the spine elements can be pre-shaped, such that both of the structural ends expand in the absence of an external restraining force. Or the spine elements can be pre-shaped and be composed of a shape memory material, such as a shape memory alloy or polymer, having a shape transitional temperature, such that both of the structural ends expand when heated to a temperature above the shape transitional temperature.

Optionally, the spine elements can be further composed of a bioabsorbable material, such that none or only a portion of the intramedullary device need be extracted from the bone, when healed. If the intramedullary device includes an interconnection structure, this too can be pre-shaped, preferably, using the same material of which the spine elements are composed.

In a third aspect of the present inventions, one or both ends of an intramedullary device can be selectively expanded and collapsed using one or more slidable connectors. The intramedullary device includes a plurality of pre-shaped spine elements longitudinally arranged to form a resultant structure. The resultant structure has a structural shaft, a first structural end, and a second structural end. One or both of the first and second structural ends expand in the absence of an external restraining force and, when expanded, has a circumference greater than that of the structural shaft. In this manner, the expanded structural end or ends can firmly engage the walls of relatively large bone cavities, such as the metaphyseal or epiphyseal areas.

The intramedullary device further includes one or more slidable connectors disposed on the spine elements to selectively expand and collapse the resultant structure. By way of non-limiting example, if only one of the structural ends expands, a slidable connector can be configured to slide relative to the plurality of spine elements to apply or release an external restraining force to the expandable structural end and, thus, selectively collapse and expand that expandable structural end. If both of the structural ends expand, two slidable connectors can be configured to slide relative to the plurality of spine elements to apply or release an external restraining force to the expandable structural ends and, thus, selectively collapse and expand the structural ends, independently from one another.

If the intramedullary device expands only at the first structural end, the spine elements can be affixed to a connector at the second structural end to ensure structural integrity of the intramedullary device, as well as to provide a convenient means of mounting. If the intramedullary device expands at both the first and second structural ends, the spine elements can be affixed to a connector at the structural shaft to ensure structural integrity of the intramedullary device. The length of the connector can be selected to provide more or less structure or column strength to the intramedullary device. The intramedullary device may optionally include a porous interconnection structure, which interconnects the plurality of spine elements at both of the expandable structural ends.

In a fourth aspect of the present inventions, one or more ends and the center of an intramedullary device can be selectively expanded and collapsed using one or more slidable connectors. The intramedullary device includes a plurality of pre-shaped spine elements longitudinally arranged to form a resultant structure. The resultant structure has a structural shaft, a first structural end, and a second structural end. One or both of the first and second structural ends expand in the absence of an external restraining force and, when expanded, has a circumference greater than that of the structural shaft. In this manner, the expanded structural end or ends can firmly engage the walls of relatively large bone cavities, such as the metaphyseal or epiphyseal areas. Additionally, the structural shaft expands in the presence of a longitudinal compressive force.

The intramedullary device further includes one or more slidable connectors disposed on the spine elements to selectively expand and collapse the resultant structure. The slidable connector can be, for example, annular rings or sleeves. The annular rings or sleeves can have through-holes or slots circumferentially disposed on the annular rings or sleeves, through which the spine elements pass.

By way of non-limiting example, if only one of the structural ends expands, a slidable connector can be located between that structural end and the structural shaft. The slidable connector can be configured to slide relative to the plurality of spine elements to selectively collapse and expand that structural end and structural shaft. That is, when the slidable connector is slid towards the structural shaft, a compressive force is applied to the structural shaft, and an external restraining force is released from the structural end, thereby expanding the structural shaft and structural end. On the contrary, when the slidable connector is slid away from the structural shaft, the compressive force is released from the structural shaft, and the external restraining force is applied to the structural end, thereby collapsing the structural shaft and structural end.

If both of the structural ends expand, one slidable connector can be located between the structural shaft and one of the ends, and another slidable connector can be located between the structural shaft and the other of the ends. The slidable connectors can then be configured to slide relative to the spine elements to selectively collapse and expand the structural ends and structural shaft.

If the intramedullary device expands only at the first structural end, the spine elements can be affixed to a connector at the second structural end to ensure structural integrity of the intramedullary device, as well as to provide a convenient means of mounting. If the intramedullary device expands at both the first and second structural ends, the spine elements can be affixed to a connector at the structural shaft to ensure structural integrity of the intramedullary device. The length of the connector can be selected to provide more or less structure or column strength to the intramedullary device.

In a fifth aspect of the present inventions, one or both ends of an intramedullary device can be selectively expanded and collapsed using a mechanical actuator. The intramedullary device includes a plurality of resilient spine elements longitudinally arranged to form a resultant structure. The resultant structure has a structural shaft, a first structural end, and a second structural end. One or both of the first and second structural ends expand and, when expanded, have a circumference greater than that of the structural shaft. In this manner, the expanded structural end or ends can firmly engage the walls of relatively large bone cavities, such as the metaphyseal or epiphyseal areas. The expanded structural end can be conveniently formed into various shapes, such as a bulbous or trumpet-like shape.

The mechanical actuator is in communication with the spine elements to selectively urge the spine elements at the first structural end and/or second structural end inward and outward. By way of non-limiting example, the mechanical actuator can include a threaded hollow connector and a threaded rod, which is threaded within the hollow connector. If the intramedullary device expands only at the first structural end, the spine elements can be affixed to the threaded connector at the second structural end. If the intramedullary device, on the other hand, expands at both the first and second structural ends, the spine elements can be affixed to the threaded hollow connector at the structural shaft.

For each structural end that expands, the mechanical actuator includes a collar rotatably mounted to the respective end of the threaded rod, and a plurality of rigid arms hingedly mounted between the collar and the spine elements at the expandable structural end. In this manner, alternate rotation of the threaded rod in first and second directions provides umbrella-like movements to selectively expand and collapse one or both of the structural ends.

In a sixth aspect of the present inventions, an intramedullary device employs a flexible cable and a removable handle assembly to facilitate the proper positioning of the device with a fractured bone. The intramedullary device includes a plurality of resilient spine elements longitudinally arranged to form a resultant structure. The resultant structure has a structural shaft, a first structural end, and a second structural end. One or both of the first and second structural ends are expandable and, when expanded, has a circumference greater than that of the structural shaft. In this manner, the expanded structural end or ends can firmly engage the walls of relatively large bone cavities, such as the metaphyseal or epiphyseal areas. The expanded structural end can be conveniently formed into various shapes, such as a bulbous or trumpet-like shape. Additionally, the structural shaft can be made expandable, such that the expanded structural shaft can firmly engage the walls of long, relatively uniform cavities, such as the medullary canal.

The intramedullary device further includes a porous interconnection structure that interconnects the plurality of spine elements at one or both of the expandable structural ends. If the structural shaft expands, the interconnection structure can interconnect the plurality of spine elements at the structural shaft. The interconnection structure can be advantageously used to provide further support to the spine elements, aid in the shaping of the resultant structure, when expanded, and/or actuate the expansion of the resultant structure, while minimizing any interruption of the biological processes within the fractured bone. The interconnection structure can be formed of a suitable structure, such as a mesh or struts, and can be variously connected to the spine elements. By way of non-limiting example, the interconnection structure can be disposed between the spine elements.

The spine elements and/or interconnection structure are pre-shaped and composed of a shape memory material, such as a shape memory alloy or polymer, having a shape transitional temperature, such that one or both of the structural ends, or all of the resultant structure, expands when heated to a temperature above the shape transitional temperature. The flexible cable is mounted to the resultant structure, preferably, at the shaft of the resultant structure. Application of a tensile force on the flexible cable pulls the intramedullary device towards the origin of the tensile force. The removable handle assembly includes a handle and a flexible rod, which is removably disposed within the resultant structure. The removable handle assembly can be used to push the intramedullary device around tight corners, and can then be removed after the intramedullary device has been properly positioned within the fractured bone.

BRIEF DESCRIPTION OF DRAWINGS

The various objects, features and advantages of the present invention may be better understood by examining the Detailed Description of the Drawings below, together with the appended figures, wherein:

FIG. 1 is a sectional side view of a femur;

FIG. 2 is a sectional side view of a tibia;

FIG. 3 is a sectional side view of a humerus;

FIG. 4 is a side view of a double-ended heat-activated intramedullary device in a collapsed state;

FIG. 5 is a side view of an alternative double-ended heating activated intramedullary device in a collapsed state;

FIG. 6 is a side view of another alternative double-ended heating activated intramedullary device in a collapsed state;

FIG. 9 is a side view of the FIG. 4 device collapsed within a femur with a fractured shaft;

FIG. 10 is a top view of the FIG. 4 device collapsed within the fractured femur, and particularly showing an indicator element of the FIG. 4 device disposed outside of an entry portal of the fractured femur;

FIG. 11 is a side view of the FIG. 4 device deployed within the fractured femur;

FIG. 23 is a side view of a single-ended heat-activated device in a collapsed state;

FIG. 24 is a side view of the FIG. 23 device in an expanded state;

FIG. 25 is a side view of the FIG. 23 device collapsed within a femur with a fractured neck;

FIG. 26 is a side view of the FIG. 23 device deployed within the fractured femur;

FIG. 27 is a side view of a double-ended self-expanding device in a collapsed state;

FIG. 28 is a side view of the FIG. 27 device in an expanded state;

FIG. 29 is a cross-sectional view of a proximal slidable connector employed in the FIG. 27 device;

FIG. 30 is a cross-sectional view of a distal slidable connector employed in the FIG. 27 device;

FIG. 31 is a cross-sectional view of a fixed connector employed in the FIG. 27 device;

FIG. 32 is a cross-sectional view of an alternative fixed connector employed in the FIG. 27 device;

FIG. 33 is a cross-sectional view of another alternative fixed connector employed in the FIG. 27 device;

FIG. 34 is a cut-away side view of the fixed connector of FIG. 31 and spine elements employed in the FIG. 27 device;

FIG. 35 is a cut-away side view of the three threaded rods employed to manipulate the proximal and distal slidable connectors and fixed connector;

FIG. 55 is a side view of the FIG. 53 device collapsed within a humerus with a fractured head;

FIG. 56 is a side view of the FIG. 53 device deployed within the fractured humerus;

FIG. 57 is a manipulatable single-end heat-activated intramedullary device in a collapsed state;

FIG. 58 is a side view of the FIG. 57 device in an expanded state;

FIGS. 70A and 70B are perspective views of another embodiment of an intramedullary device with splines in collapsed and expanded states, respectively;

FIGS. 71A and 71B are perspective views of one end of the device of FIGS. 70A and 70B, showing splines on the end in collapsed and expanded states, respectively;

FIGS. 73A and 73B are perspective views of yet another embodiment of an intramedullary device with splines in collapsed and expanded states, respectively;

FIGS. 74A and 74B are perspective views of one end of the device of FIGS. 73A and 73B, showing splines on the end in collapsed and expanded states, respectively;

FIGS. 75A and 75B are cross-sectional views of a femur including a fracture being stabilized by another intramedullary device, in accordance with another aspect of the present inventions; and FIGS. 76A, 76B, 77A, and 77B are cross-sectional views of a femur including a fracture being stabilized by alternative embodiments of intramedullary devices, in accordance with the present invention.

DETAILED DESCRIPTION OF THE DRAWINGS

Figure 7:
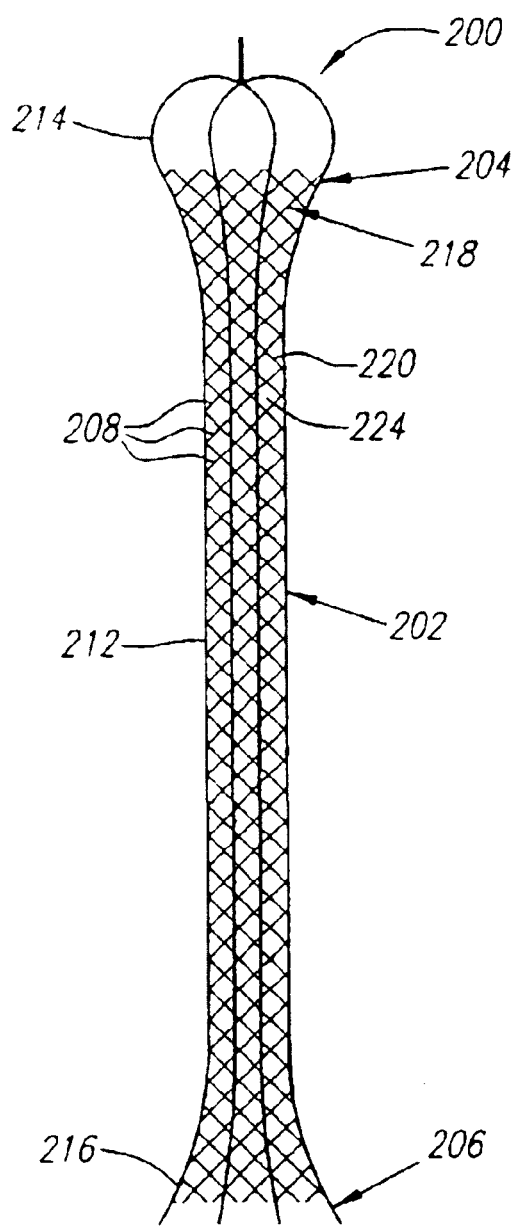
FIG. 7 is a side view of the FIG. 4 device in an expanded state.

The present inventions can be employed to mend a variety of fractured bones, such as the femur, tibia, or humerus. By way of background the pertinent features of these bones will be described with reference to FIGS. 1–3. Referring specifically to FIG. 1, a femur 100 can be divided into six anatomical regions: a diaphysis or midshaft 102, proximal metaphysis 104, distal metaphysis 106, proximal epiphysis or head 108, distal epiphysis 110, and femoral neck 112. The femur 100 is composed of a hard cortex 114 and a medullary cavity 116. For the purposes of this invention, the medullary cavity 116, includes a medullary canal 118, which runs through the center of the shaft 102, as well as proximal and distal metaphyseal areas 120 and 122, and proximal and distal epiphyseal areas 124 and 126.

Referring specifically to FIG. 2, a tibia 140 can be divided into five anatomical regions: a diaphysis or midshaft 142, a proximal metaphysis 144, distal metaphysis 146, proximal epiphysis 148, and distal epiphysis 150. Like the femur 100, the tibia 140 is composed of a hard cortex 152 and a medullary cavity 154. For the purposes of this specification, a medullary cavity 154 includes a medullary canal 156, which runs through the center of the shaft 142, as well as proximal and distal metaphyseal areas 158 and 160, and proximal and distal epiphyseal areas 162 and 164.

Referring to FIG. 3, a humerus 170, like the tibia 140, can be divided into five anatomical regions: a diaphysis or midshaft 172, proximal metaphysis or neck 174, distal metaphysis 176, proximal epiphysis or head 178, and distal epiphysis 180. Like the femur 100 and tibia 140, the humerus 170 is composed of a hard cortex 182 and a medullary cavity 184. For the purposes of this specification, a medullary cavity 184 includes a medullary canal 186, which runs through the center of the shaft 172, as well as proximal and distal metaphyseal areas 188 and 190, and proximal and distal epiphyseal areas 192 and 194.

It should be emphasized that the femur 100, tibia 140, and humerus 170 represent exemplary bones in which the present inventions can be employed. The present inventions can be used to mend fractured bones, other than the femur 100, tibia 140, and humerus 170, without straying outside the scope of the present inventions.

Although the medullary canals of the femur 100, tibia 140 and humerus 170 have a generally uniform circumference along the shafts of these bones, the medullary canals are in communication with larger metaphyseal and epiphyseal areas. Thus, the medullary cavities of the femur 100, tibia 140, and humerus 170, as a whole, have a differential circumference, with the circumference at the ends being greater than the circumference at the middle of these medullary cavities. The intramedullary devices of the present inventions are able to reversibly expand and adopt a preformatted shape, fitting the internal shape of the medullary cavity. Use of the medullary devices rotationally locks the bone segments of a fractured bone, while at the same time providing sufficient stability in the other planes without the necessity of screws. If screws are needed, they may be used in conjunction with the intramedullary devices. These devices are minimally invasive, almost completely percutaneous, and implanted through only one incision, the entry portal. Different lengths and types of the intramedullary devices may be necessary, depending upon the bone to be fixed. The intramedullary devices may accommodate a variety of bone circumferences.

The intramedullary devices are deployed using methods similar to those that use conventional intramedullary nails for bones, such as the femur, tibia and humerus, while minimizing the X-rays needed after the close reduction of the fracture and control of insertion. The intramedullary devices can also be deployed in the radius and ulna through the standard approaches used for the insertion of Rush-type nails. For immature bones (with open physis), the intramedullary devices can be inserted through entry portals below the proximal physis and above the distal physis, without including them in the area of fixation. A long intramedullary device may be used, for instance, in knee fusion cases including the femur and tibia. A short intramedullary device could be used, for instance, with metatarsal and metacarpal bone fractures.

This intramedullary approach, along with the minimally invasive nature of the intramedullary devices, generally leaves the periosteum of the fractured bone untouched. In addition, the intramedullary devices are lighter without compromising the stability, allow better visualization on follow up X-rays due to less metal, and are compatible with the use of other types of externally biomechanic stimuli that could be potentially used as union enhancement treatment. Using certain alloys, the material in which the intramedullary devices are constructed from could remain non-magnetic, avoiding interference with most modern imaging techniques such as MRI (magnetic resonance imaging).

A double-ended heat-activated intramedullary device 200 constructed in accordance with the present inventions, is described with reference to FIGS. 4–8. Referring specifically to FIGS. 4 and 7, the device 200 is shown in a collapsed state and an expanded state, respectively. The device 200 has a shaft 202, a proximal end 204, and a distal end 206. The device 200 is composed of an array of resilient spine elements 208, which are arranged in a longitudinal fashion. Each of the spine elements 208 includes a spine shaft 212, a proximal spine end 214, and a distal spine end 216. In the illustrated embodiment, the spine elements 208 have a rectangular cross-section, thereby providing the structure of the device 200 with more strength. The cross-section of the spine elements 208, however, can be any suitable geometry without straying outside the scope of the present invention.

The device 200 further includes a porous interconnecting structure 218, which interconnects the spine elements 208. As will be described in further detail below, the porous interconnecting structure 218 provides structural integrity to the device 200, while allowing the lateral flow of liquid and semi-liquid material therethrough. The interconnecting structure 218 takes the form of a mesh 220, which is disposed circumferentially in relation to the spine elements 208. In the illustrated embodiment, the mesh 220 is disposed between the spine elements 208. The mesh, however, can alternatively be disposed about or within the spine elements 208.

The mesh 220 extends almost the entire length of the spine elements 208. In alternative embodiments, the interconnecting structure 218 takes the form of a mesh that extends only a portion of the entire length of the spine elements 208. For example, FIG. 5 illustrates a heat-activated intramedullary device 240 with a mesh 220 that interconnects the spine elements 208 at the proximal and distal ends 214 and 216 thereof. The interconnecting structure 218 can also be formed of a structure other than mesh. For example, FIG. 6 illustrates a heat-activated intramedullary device 250 with long struts 252 that interconnect the spine elements 208 at the proximal and distal ends 214 and 216 thereof.

The device 200 further includes an indicator element 222, which is formed by the proximal end 214 of an additionally lengthy spine element 208. As will be described in further detail below, the indicator element 222 can be used to conveniently locate the device 200 immediately prior to extraction of the device 200 from a mended bone. As will also be described in further detail below, the indicator element 222 also facilitates in the deployment of the device 200.

As illustrated in FIG. 7, the device 200, when expanded, generally takes the form of an hourglass-like shape. That is, the device 200 has a differential circumference along its longitudinal axis, with the circumference at the proximal and distal ends 204 and 206 being greater than the circumference at the shaft 202 of the device 200. It should be noted that the cross-section of the expanded device 200 need not have a circular geometry, but may be have any suitable geometry, such as elliptical. As illustrated, the proximal end 204 of the device 200 is formed into a bulbous shape, caused by connecting the tips of the proximal spine ends 214 together. The bulbous-shaped proximal end 204 of the device 200 can be advantageously used to facilitate matching of bulbous-shaped bone cavities, such as the proximal metaphyseal area 158 of the tibia 140 (shown in FIG. 2). In contrast, the tips of the distal spine ends 216 are not connected together, effecting a trumpet shape at the distal end 206 of the device 200. The trumpet-shaped distal end 206 of the device 200 can be advantageously used to facilitate matching of trumpet-shaped bone cavities, such as the distal metaphyseal area 160 of the tibia 140 (shown in FIG. 2). Of course, both the proximal and distal ends 204 and 206 can be formed into either a bulbous shape or a trumpet shape. As will be described later, the final shape of the device 200 will be determined by the particular anatomical features of the medullary cavity in which the device 200 is deployed.

As shown in FIG. 7, the mesh 220 has spaces 224, the size of which differentially vary along the length of the device 200. Specifically, the size of the spaces 224 increase as the spaces 224 near the proximal and distal ends 204 and 206 of the device 200. In this manner, expansion of the proximal spine ends 214 and distal spine ends 216 are increased in relation to the spine shafts 212. As will be described in further detail below, this feature is advantageous in that the size of the medullary cavity at the ends is typically greater than at the shaft.

The structure of the device 200 is predisposed to expand. Specifically, the spine elements 208 and mesh 220 are composed of a shape memory alloy, such as NITINOL™, which exhibits a shape memory effect. That is, the shape memory alloy, after being deformed, remembers its original shape and returns to it when heated above a shape transitional temperature. In this manner, the spine elements 208 take the form of a predetermined shape during deployment of the device 200 when exposed to the shape transitional temperature of the shape memory alloy. In alternative embodiments, either one or the other of the spine elements 208 and mesh 220 is formed of a shape memory alloy. Alternatively, the spine elements 208 and mesh are composed of a shape memory polymer.

Figure 8:
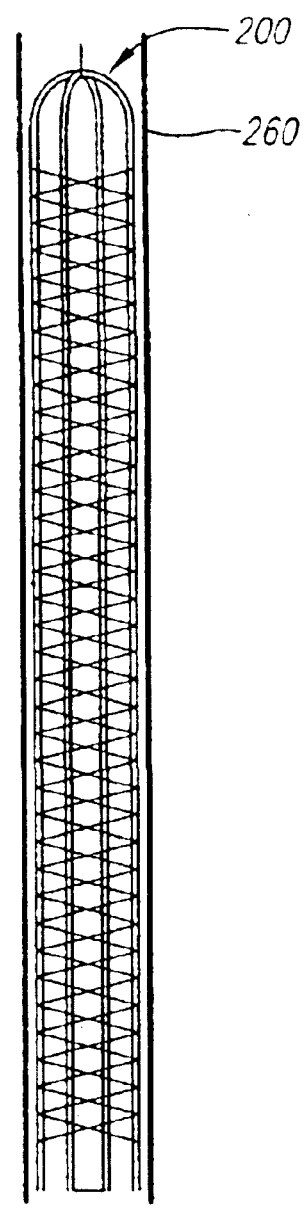
FIG. 8 is a side view of the FIG. 4 device disposed in an insertion sleeve.

The device 200 is constructed such that the shape of the device 200 matches the medullary cavity, and specifically the medullary canal and metaphyseal areas, of the fractured bone in which the device 200 is deployed, with variability in length and diameter, according to anatomical charts of standard individuals. The device 200 can be custom-made with a non-standard shape, based on X-rays of the fractured bone to be mended. During manufacture of the device 200, the spine elements 208 and mesh 220 are constructed on a mandrel at a temperature well above the shape transitional temperature of the shape memory alloy, i.e., when the crystalline structure of the shape memory alloy is entirely in the parent phase (austenite crystal configuration). Preferably, the shape transitional temperature of the particular shape memory material used to manufacture the device 200 is selected to be within a range of around normal body temperature. A wider range of shape transitional temperatures, however, may be used without straying outside the scope of the present invention. As shown in FIG. 8, the collapsed device 200 can then be stored inside a thin rigid insulated sleeve 260, which will be described in further detail below, that can be used to insert the device 200 inside a fractured bone.

The spine elements 208 are configured to outwardly bend in a curve and the mesh 220 is configured to expand outward when exposed to a temperature greater than the shape transitional temperature of the shape memory alloy. Thus, when the device 200 is exposed to a temperature above the shape transitional temperature of the shape memory alloy, the device 200 is placed into the expanded state, as shown in FIG. 7. On the contrary, when the device is exposed to a temperature below the shape transitional temperature of the shape memory alloy, the device 200 is placed into the collapsed state, as shown in FIG. 4. In this regard, the device 200 is then collapsed by cooling the device 200 to a temperature below the shape transitional temperature (e.g., room temperature), such that the martensite crystal structure replaces the austenite crystal structure of the shape memory alloy.

The intramedullary device 200 can be advantageously used to mend bones with fractured shafts. With reference to FIGS. 9–14, a preferred method of deploying the intramedullary device 200 within the medullary cavity 116 of a fractured femur 100 is described. The femur 100 is shown with a point of fracture 128 on the shaft 102. It should be noted that the device 200 can be deployed in bones other than the femur 100, such as the tibia, fibula, humerus, ulna or radius, without straying outside the scope of the present invention.

Referring specifically to FIGS. 9 and 10, prior to insertion of the device 200 within the medullary cavity 116 of the femur 100, an opening is made through the top of the proximal metaphysis 104 to create an entry portal 130 therein, providing access to the medullary cavity 116. A solid thin metallic guide (not shown) is inserted through the entry portal 130, through the medullary canal 118 until the distal tip of the guide makes contact with the wall of the distal epiphyseal area 126. If reaming is desired (which is generally not necessary with the device 200), the inner surface of the cortex 114 can be reamed, using methods well known in the prior art. The device 200 with the insertion sleeve 260 is then introduced into the femur 100 through the entry portal 130 and properly positioned within the medullary cavity 116 of the femur 100. The device 200 is positioned, such that the indicator element 222 is disposed outside the entry portal 130, thereby facilitating location of the device 200 when it is desired to extract the device 200 from the mended femur 100, as will be described in further detail below.

Once the device 200 is in position, and the rotational orientation of the fractured femur 100 is confirmed with an image intensifier, the device 200 is deployed within the medullary cavity 116 of the femur 100, as illustrated in FIG. 11. In particular, the insertion sleeve 260 is removed and the spine elements 208 and mesh 220 are heated to a temperature above the shape transitional temperature of the shape memory alloy, transforming the crystal structure of the shape memory alloy from martensite to austenite. In the illustrated embodiment, the device 200 is heated by transmitting electrical energy to the spine elements 208 and mesh 220 via the indicator element 222. Any conventional method capable of heating the device, however, may be used. For example, the methods of heating may use sophisticated radio frequency induction heaters or simple saline (physiological) solution warmed up to the required temperature. The radio frequency inductor should avoid high frequencies (microwave range) to avoid heating the surrounding soft tissues.

During expansion of the device 200, the shape of the device 200 will adopt the inner shape of the medullary cavity 116 of the femur 100. As illustrated in FIG. 11, the proximal and distal metaphyseal areas 120 and 122 have a greater circumference than the generally uniform circumference of the medullary canal 118. As can be seen, however, the bulbous-shaped proximal end 204 and trumpet-shaped distal end 206 of the expanded device 200 adapt to the proximal and distal metaphyseal areas 120 and 122, while the shaft 202 of the expanded device 200 adapts to the medullary canal 118. Thus, the larger expanded proximal and distal ends 204 and 206 firmly engage the walls of the respective proximal and distal metaphyseal areas 120 and 122, while the smaller expanded shaft 202 firmly engages the walls of the medullary canal 118.

Additionally, the expanded device 200 adapts itself to the minute variations within the medullary cavity 116, facilitated by the shape variation of each spine element 108 and mesh 220. As can be seen, the device 200 is entirely deployed within the medullary cavity 116 of the femur 100, and, with the exception of the indicator element 222, is not connected to, influenced or constrained by the entry portal 130. As a result, tendencies of changes in reduction or alignment of the femur 100 are avoided, decreasing malunion and non-union rates. Optionally, additional screws or wires may be used, according to the particular surgeon's criteria, as long as any exposed metal components used are composed of the same material. The guide (not shown) is then removed from the medullary cavity 116 out through the entry portal 130. Alternatively, the guide 262 can be removed prior to expansion of the device 200.

Figure 12:
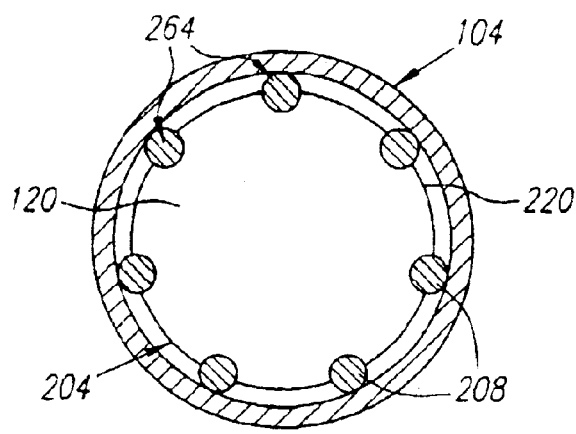
FIG. 12 is a cross-sectional view of the proximal end of the FIG. 4 device deployed within the fractured femur.
Figure 13:
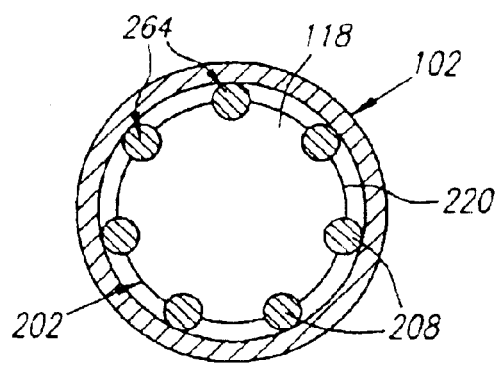
FIG. 13 is a cross-sectional view of the shaft of the FIG. 4 device deployed within the fractured femur.
Figure 14:
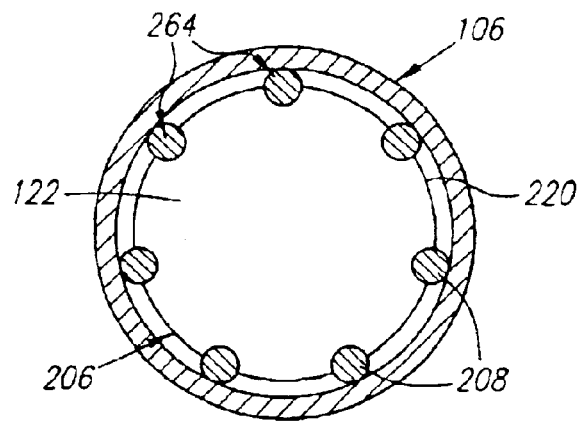
FIG. 14 is a cross-sectional view of the distal end of the FIG. 4 device deployed within the fractured femur.

With reference to FIG. 12, the proximal end 204 of the expanded device 200 firmly engages the walls of the proximal metaphyseal area 120 at a number of contact points 264 along the spine elements 208. With reference to FIG. 13, the shaft 202 of the expanded device 200 firmly engages the walls of the medullary canal 118 at a number of contact points 264 along the spine elements 208. With reference to FIG. 14, the distal end 206 of the expanded device 200 firmly engages the walls of the distal metaphyseal area 122 at a number of contact points 264 along the spine elements 208.

Referring back to FIG. 11, the mesh 220 provides additional points of contact. In comparison to non-porous structures, however, the porous nature of the mesh 220 allows for faster recovery of the endosteal circulation, which promotes healing, and also permits the free circulation of potential factors or drugs that could be delivered for treatment. The mesh 220 further allows the transmission of desired micromovements to the fracture site. Also, when using the device 200 in contaminated fractures, the mesh 220 advantageously minimizes the spread of the contamination, due to the recovery of the endosteal circulation and the better diffusion of antibiotics (if given as a concomitant treatment).

Due to the elasticity of the spine elements 208 and mesh 220, the contact points formed between the device 200 and the wall of the medullary cavity 116 may move during treatment, as the medullary cavity 116 changes shape and, thus, allow the device 200 to maintain firm engagement with the walls of the intramedullary cavity 116. Thus, it can be seen that the structure of the device 200 provides multiple, random, points of contact along the longitudinal axis of the device 200, allowing the device 200 to adapt to the shape of the medullary cavity 116 of the femur 100. The device 200, therefore, not only provides structural support to the fractured femur 100, but maintains that structural support until the femur 100 is mended.

Figure 15:
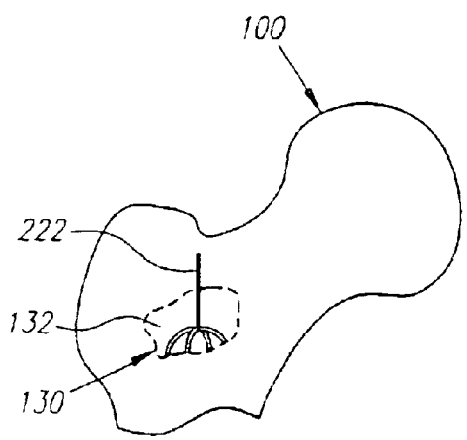
FIG. 15 is a top view of the FIG. 4 device deployed within the fractured femur, and particularly showing new bone growth covering the indicator element of the device.
Figure 16:
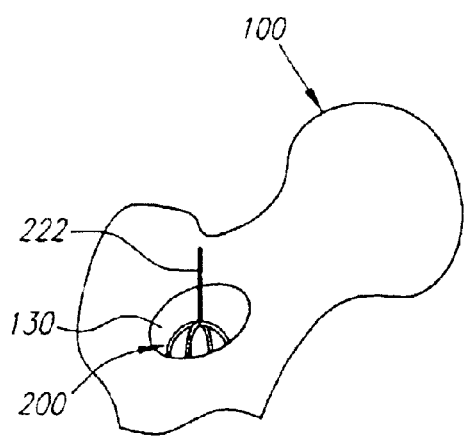
FIG. 16 is a top view of the FIG. 4 device deployed within the fractured femur, and particularly showing the new bone growth removed.
Figure 17:
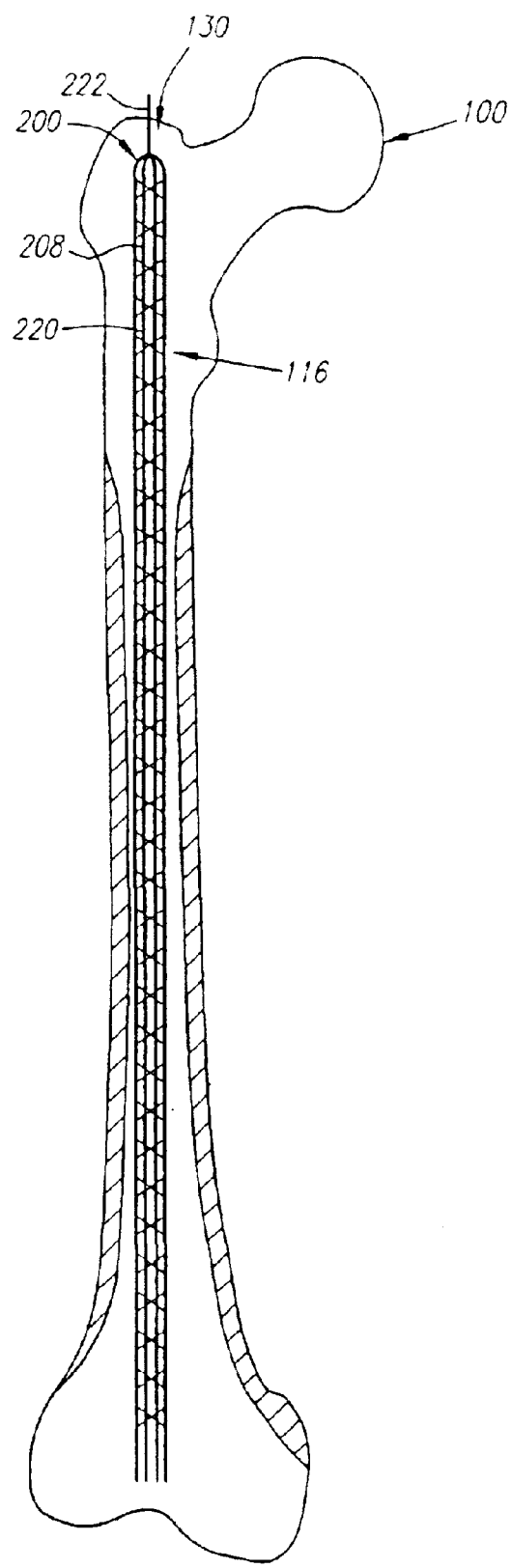
FIG. 17 is a side view of the FIG. 4 device collapsed within the fractured femur prior to extraction.

When definitive removal of the device 200 is required, preferably when the femur 100 is completely healed, as confirmed by radiography, a second operation is needed. With reference to FIGS. 15–17, a preferred method of extracting the device 200 from the femur 100 is described. The entry portal 130, which at this point is typically covered by new bone growth 132, is exposed through one small skin incision (FIG. 15). The indicator element 222, which may either be protruding from or buried under the surface of the new both growth 132, is then identified to locate the device 200. Specifically, the new bone growth 132 is removed around the indicator element 222 to expose the entry portal 130 (FIG. 16). Once located, the device 200 is collapsed by cooling the spine elements 208 and mesh 220 (FIG. 17). Specifically, heat energy can be transmitted away from the spine elements 208 and mesh 220 by cooling the indicator element 222. Alternatively, or in conjunction with cooling the indicator element 222, a cooled mesh 220 guide (not shown) can be introduced through the center of the device 200 to cool the spine elements 208 and mesh 220. As will be described in farther detail below, the device 200 is extracted from the femur 100. Optionally, to facilitate extraction of the device 200 from the femur 100, a retrievable sleeve (not shown) is inserted over the device 200 to separate the spine elements 208 and mesh 220 from the walls of the medullary cavity 116.

It should be noted that the device 200 may optionally be made completely of, or partially of, a bioabsorbable material, so that, in some instances, a second operation to retrieve the device 200 would not be necessary, or only a portion of the device 200 would have to be retrieved. In this invention, either or both of the spine elements 208 and mesh 220 can be made of the bioabsorbable material.

Figure 18:
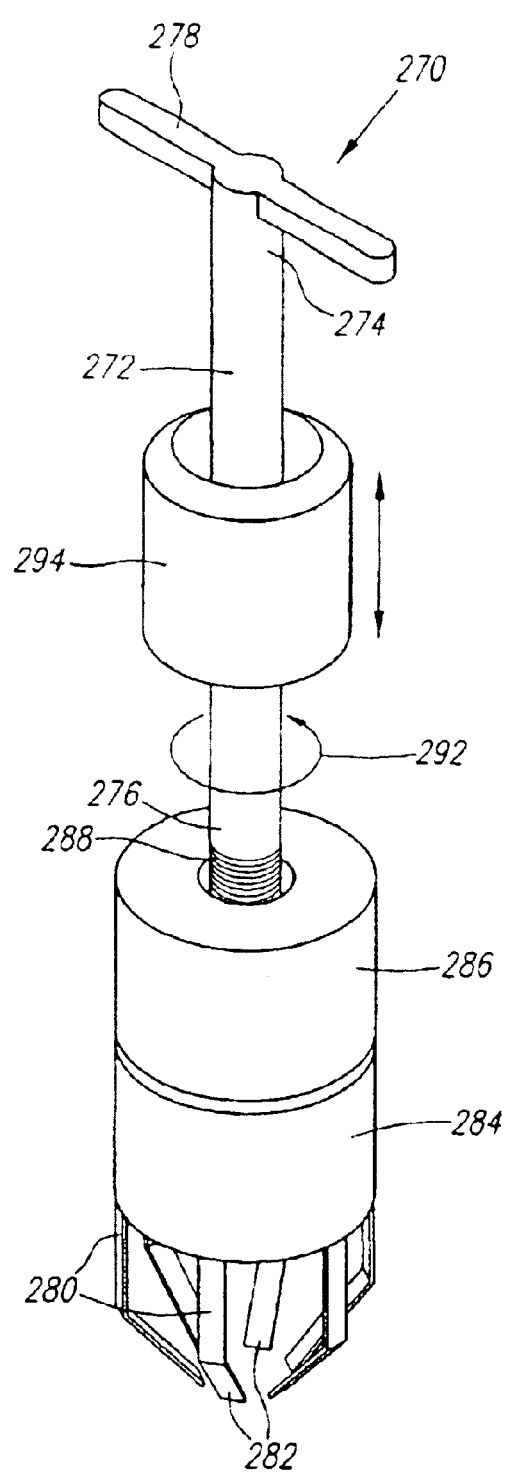
FIG. 18 is a perspective view of an extraction device in an open state.
Figure 19:
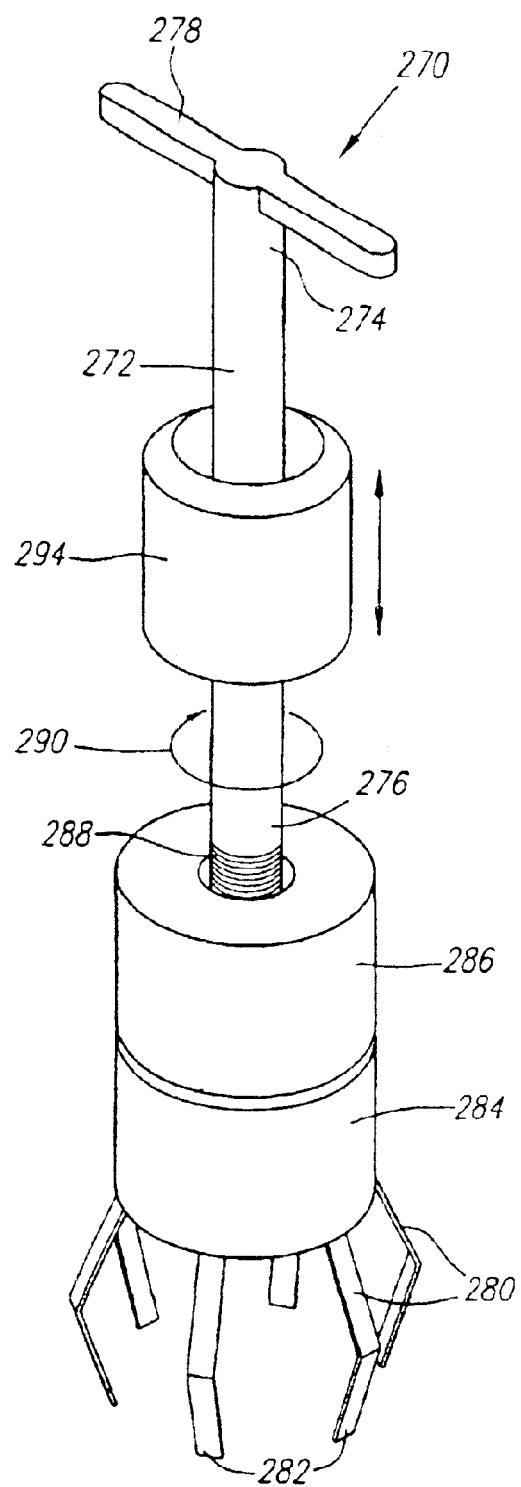
FIG. 19 is a perspective view of the FIG. 18 extraction device in a closed state.

With reference to FIGS. 18 and 19, an extraction tool 270, which can be used to extract the intramedullary device 200, is described. The extraction tool 270 includes a shaft 272 having a proximal end 274 and a distal end 276. A flat T-shaped head 278 is formed at the proximal end 274 of the shaft 272, and a multitude of extraction legs 280 are formed at the distal end 276 of the shaft 272. As will be described in further detail below, the extraction legs 280 have distal ends 282, which are bent inward to facilitate engagement with the spine elements 208 of the intramedullary device 200. The extraction tool 270 further includes a collar 284, which is slidably disposed on the shaft 272 proximal to the extraction legs 280. Distal movement of the collar 284 forces the extraction legs 280, which are pre-shaped to pivot outward, to pivot inward, thereby closing the extraction tool 270 (FIG. 19). Proximal movement of the collar 284 allows the extraction legs 280 to pivot outward, thereby opening the extraction tool 270 (FIG. 18).

To provide controlled movement of the collar 284, the extraction tool 270 further includes a threaded collar 286, which is in engagement with a threaded portion 288 of the shaft 272 proximal the collar 284. Rotation of the threaded collar 286 in a first direction 290 (FIG. 19) moves the threaded collar 286 distally, causing the collar 284 to controllably move distally to close the extraction tool 270. Rotation of the threaded collar 286 in a second opposite direction 292 (FIG. 18) moves the threaded collar 286 proximally, allowing the collar 284 to controllably move proximally to open the extraction tool 270. The extraction tool 270 further includes a collared hammer 294, which is slidably disposed on the shaft 272 between the threaded collar 286 and the T-shaped head 278. As will be described in further detail below, the collared hammer 294 can be abruptly slid proximally until the proximal surface of the collared hammer 294 strikes the bottom surface of the T-shaped head 278. In this manner, impulsive forces can be applied to the extraction tool 270 to facilitate removal of the intramedullary device 200 from the medullary cavity 116, out through the entry portal 130 of the femur 100.

Figures 20, 21, 22:
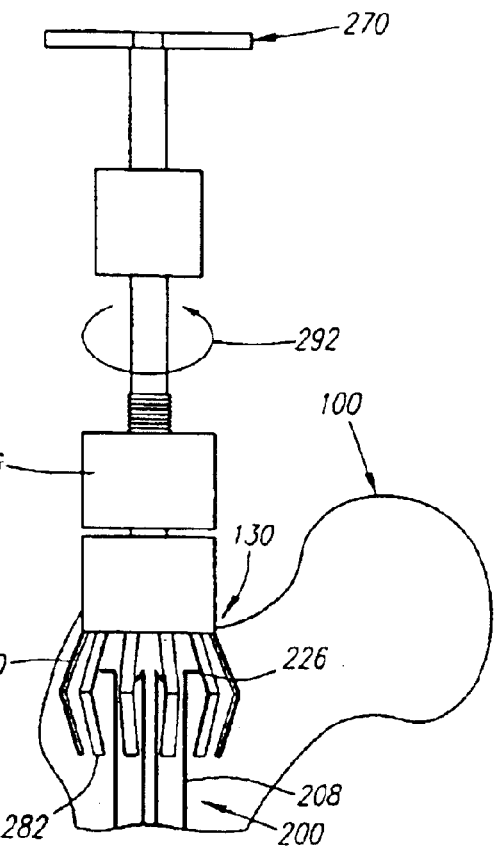
FIG. 20 is a side view of the FIG. 18 closed extraction device within the fracture femur.
FIG. 21 is a side view of the FIG. 18 open extraction device within the fractured femur, wherein the extraction device is advanced over the spine elements of the FIG. 4 device.
FIG. 22 is a side view of the FIG. 18 closed extraction device within the fractured femur, wherein the extraction device is engaged with the spine elements of the FIG. 4 device.

Referring to FIGS. 20–22, a preferred method of extracting the collapsed medullary device 200 from the femur 100 is described. First, the extraction legs 280 of the extraction tool 270 are introduced through the entry portal 130 of the femur 100, while the extraction tool 270 is in the closed position (FIG. 20). As can be seen, spine elements 208 include proximal tips 226, which are bent outward to facilitate the engagement between the extraction legs 280 of the extraction tool 270 and the spine elements 208. The extraction tool 270 is then opened (by rotating the threaded collar 286 in the second direction 292) and advanced distally, such that the distal ends 282 of the extraction legs 280 are disposed around the proximal tips 226 of the spine elements 208 (FIG. 21). The extraction tool 270 is then closed (by rotating the threaded collar 286 in the first direction 290), such that the distal ends 282 of the extraction legs 280 engage the proximal tips 226 of the spine elements 208 (FIG. 22). The intramedullary device 200 is then extracted out the entry portal 130 by repeatedly striking the T-shaped head 278 with the collared hammer 294.

A single-ended heat-activated intramedullary device 300 constructed in accordance with the present inventions, is described with reference to FIGS. 23 and 24. To the extent that the features of the device 300 are similar to those hereinbefore described, identical reference numbers have been assigned. The single-ended heat-activated intramedullary device 300, like the double-ended heat-activated intramedullary device 200, expands when subjected to a temperature above the shape transitional temperature. Unlike the device 200, which expands at both ends, the device 300 expands only at one end.

Specifically, and with reference to FIGS. 23 and 24, the device 300 is shown in a collapsed state and an expanded state, respectively. The device 300 includes a shaft 302, a proximal end 304 with a handle assembly 308, and a distal end 306. The porous interconnection structure 218 which, in this embodiment, is formed by the mesh 220, interconnects the spine elements 208. Again, the interconnection structure 218 can take the form of a structure other than the mesh 220 and need not extend the entire length of the spine elements 208. The handle assembly 308 includes a handle 310 and a fixed connector 312, which are removably attached to each other by threads or other means, such as snapping. In the illustrated embodiment, the fixed connector 312 is a hollow tubular member. The proximal spine ends 214 are mounted to the connector 312 via slots (not shown) made in the connector 312, while the distal spine ends 216 are disconnected from each other. The indicator element 222 is disposed through and extends proximal to the fixed connector 312.

As illustrated in FIG. 24, the device 300, when expanded, takes the form of a trumpet shape. It should be noted, however, that the expanded device 300 can take the form of a bulbous shape when the tips of the distal spine ends 216 are connected together. As shown in FIG. 24, the spaces 224 of the mesh 220, the size of which vary differentially along the length of the device 300. Specifically, the size of the spaces 224 increase as the spaces 224 near the distal end 306 of the device 300. In this manner, expansion of the distal spine ends 216 are increased in relation to the spine shafts 212. The spine elements 208 and mesh 220 are formed of a shape memory alloy or polymer to actuate expansion of the device 300. The spine elements 208 are configured to outwardly bend in a curve and the mesh 220 is configured to expand outward when exposed to a temperature greater than the shape transitional temperature of the shape memory alloy, thereby effecting the shape of the expanded device 300, as shown in FIG. 24. In alternative embodiments, either one or the other of the spine elements 208 and mesh 120 is formed of a shape memory alloy.

The device 300 can be advantageously used to mend bones with fractured necks. With reference to FIGS. 25 and 26, a preferred method of deploying the intramedullary device 300 within the medullary cavity 116 of a fractured femur 100 is described. The femur 100 is shown with a point of fracture 134 on the neck 112. It should be noted, however, that the device 300 can be deployed in bones other than the femur 100, such as the head of the humerus, the olecranon, and other similar sites, without straying outside the scope of the present invention.

Referring specifically to FIG. 25, prior to insertion of the device 300 within the medullary cavity 116 of the femur 100, an opening is made through the side of or below the proximal metaphysis 104 to create an entry portal 136 therein, providing access to the medullary cavity 116. The device 300, with an insertion sleeve (not shown), is then introduced over a guide (not shown) into the femur 100 through the entry portal 136, and properly positioned within the neck 112 and head 124 of the femur 100. The handle 310 can be used to facilitate insertion of the device 300. The connector 312 is firmly located within the entry portal 136.

Once the device 300 is in position, and the rotational orientation of the fractured femur 100 is confirmed with an image intensifier, the device 300 is deployed within the medullary cavity 116 of the femur 100, as illustrated in FIG. 26. Deployment of the device 300 is accomplished much like deployment of the device 200, described above, that is, the insertion sleeve (not shown) is removed and the spine elements 208 and mesh 220 are heated to a temperature above the shape transitional temperature of the shape memory alloy. The handle 310 can then be unscrewed, or otherwise removed, from the connector 312, leaving the connector 312 disposed within the entry portal 136.

As illustrated in FIG. 26, the proximal epiphyseal area 124 has a greater circumference than the circumference of the proximal metaphyseal area 120 within the femoral neck 112. As can be seen, however, the trumpet-shaped distal end 306 of the expanded device 300 adapts to the proximal epiphyseal area 124. Thus, the larger expanded distal end 306 firmly engages the walls of the proximal epiphyseal area 124 at a multitude of contact points, while adapting to minute variations within the medullary cavity 116. The firm disposition of the connector 312 within the entry portal 136 provides further stability to the fractured femur 100. The device 300, therefore, not only provides structural support to the fractured femur 100, but maintains that structural support until the femur 100 is mended.

Once the femur 100 is mended, the device 300 can be extracted from the femur 100 in a manner much like that described with respect to the device 200 (FIGS. 15–17, 20–22). Of course, if the device 300 is made completely of, or partially of, a bioabsorbable material, it may not be necessary to extract the device 300, or only a portion of the device 300 would have to be retrieved.

A double-ended self-expanding intramedullary device 400 constructed in accordance with the present inventions, is described with reference to FIGS. 27–34. Referring specifically to FIGS. 27 and 28, the device 400 is shown in a collapsed state and an expanded state, respectively. The device 400 has a shaft 402, a proximal end 404, and a distal end 406. The device 400 is composed of a multitude of resilient spine elements 408, which are arranged in a longitudinal fashion. Each of the spine elements 408 includes a spine shaft 412, a proximal spine end 414, and a distal spine end 416. In the illustrated embodiment, the spine elements 408 have a rectangular cross-section, thereby providing the structure of the device 400 with more strength. The cross-section of the spine elements 408, however, can be any suitable geometry without straying outside the scope of the present invention.

The device 400 further includes a porous interconnecting structure 418, which interconnects the spine elements 408. The porous interconnecting structure 418, like the interconnecting structure 218 described above with respect to the device 200, provides structural integrity to the device 400, while allowing the lateral flow of liquid and semi-liquid material therethrough. In the illustrated embodiment, the interconnecting structure 418 takes the form of long struts 420, which interconnect the spine elements 408 at the proximal and distal ends 414 and 416 thereof. The device 400 further includes an indicator element 422, which is formed at the end of an additionally lengthy spine element 408.

The device 400 includes a fixed connector 424 and, in particular, a sleeve, on which the spine shafts 412 are mounted. The sleeve 424 provides structural support to the device 400, and can be made longer or shorter depending on the column strength required by the device 400 during insertion thereof into a fractured bone. Optionally, additional column strength can be provided to the device 400 through the use of an outer sleeve (not shown), which extends the entire length of the device 400. In the illustrated embodiment, the spine elements 408 and sleeve 424 are formed from the same piece of material. Specifically, as shown in FIG. 34, proximal slots 430 and distal slots 432 can be cut from an elongate tubular member 434, wherein the slots 430 and 432 form regions offset from a center 436 of the tubular member 434 through the respective tips of the tubular member 434. The unslotted center region 436 of the tubular member 434 forms the sleeve 424, and the material between the proximal and distal slots 430 and 432 forms the spine elements 408.

Alternatively, the sleeve 424 can be made separately from the spine elements 408, in which case, the spine shafts 412 are suitably mounted to the sleeve 424. For example, the exterior surface of the sleeve 424 can be fluted, in which case, the spine shafts 412 are fixably disposed within slots 438, as shown in FIG. 32. Or longitudinal holes 440 can be formed in the sleeve 424, in which case, the spine shafts 412 are fixably disposed through the holes 440, as shown in FIG. 33. For the purposes of this specification, the spine element 408 can be represented by a single element, or can be represented by two collinear elements separated by the sleeve 424. For example, if the sleeve 424 and spine elements 408 are formed from the same piece of material, as illustrated in FIG. 34, a spine element 408 is formed by two collinear elements extending from the sleeve 424 in opposite directions. On the other hand, if the sleeve 424 and spine elements 408 are formed from separate pieces of material, as illustrated in FIGS. 32 and 33, the spine element 408 can be formed by a single element extending through the entire length of the sleeve 424.

As illustrated in FIG. 28, the device 400, when expanded, generally takes the form of an hourglass-like shape. As illustrated, the proximal end 404 of the device 400 is formed into a bulbous shape, caused by connecting the tips of the proximal spine ends 414 together. In contrast, the tips of the distal spine ends 416 are not connected together, effecting a trumpet shape at the distal end 406 of the device 400. Of course, both the proximal and distal ends 404 and 406 can be formed into either a bulbous shape or a trumpet shape.

The structure of the device 400 is predisposed to expand. Specifically, similar to the other embodiments disclosed herein, the spine elements 408 may be composed of resilient material, such as stainless steel, titanium-vanadium, titanium-aluminum-vanadium, nickel-titanium, or other titanium alloy, or other suitable biocompatible material. The resilient material, after being deformed by an external restraining force, returns to its original shape when the restraining force is removed. In this manner, the spine elements 408 and struts 420 take the form of a predetermined shape during deployment of the device 400 absent an external restraining force. In alternative embodiments, either one or the other of the spine elements 408 and struts 220 is pre-shaped.

The device 400 is constructed, such that the shape of the device 400 matches the metaphyseal areas of the fractured bone in which the device 400 is deployed in a manner similar to that described with respect to the device 200. In accordance with this criteria, the proximal and distal spine ends 414 and 416 are configured to bend outward and/or the struts 420 are configured to bend in a tight curve, absent an exterior restraining force. Thus, when no exterior restraining force is applied to the proximal and distal ends 404 and 406 of the device 400, the device 400 is naturally placed into the expanded state, as shown in FIG. 28. On the contrary, when an external restraining force is applied to the proximal and distal ends 404 and 406 of the device 400, the device 400 is forced into a collapsed state, as shown in FIG. 27.

Referring back to FIGS. 27 and 28, the device 400 includes a proximal slidable connector 426 and a distal slidable connector 428, which, in the illustrated embodiment, take the form of annular rings. The proximal and distal slidable connectors 426 and 428 are both slidably disposed on the spine elements 408 to alternately apply and remove an external restraining force to and from the proximal and distal ends 404 and 406. In this manner, the device 400 can be alternately expanded and collapsed. In particular, the proximal annular ring 426 and distal annular ring 428 each includes circumferentially disposed holes 442 through which the spine elements 408 are disposed, as illustrated in FIGS. 29 and 30. The shape of the holes 442 will depend upon the cross-sectional shape of the spine elements 408. For example, in the illustrated embodiment, the cross-sectional shape of the spine elements 408 is rectangular. In this case, the shape of the holes 442 in the proximal and distal annular rings 426 and 428 is rectangular.

Referring back to FIGS. 27 and 28, the proximal annular ring 426 is located on the spine elements 408 proximal to the sleeve 424, and the distal annular ring 428 is located on the spine elements 408 distal to the fixed connector 426. Thus, as shown in FIG. 27, movement of the proximal annular ring 426 towards the proximal end 404 of the device 400, applies an external restraining force thereto, thereby collapsing the proximal end 404 of the device 400. Similarly, movement of the distal annular ring 428 towards the distal end 406 of the device 400, applies an external restraining force therefrom, thereby collapsing the distal end 406 of the device 400. On the contrary, movement of the proximal annular ring 426 away from the proximal end 404 of the device 400, removes the external restraining force therefrom, thereby allowing expansion of the proximal end 404 of the device 400. Similarly, movement of the distal annular ring 428 away from the distal end 406 of the device 400, removes the external restraining force therefrom, thereby allowing expansion of the distal end 406 of the device 400. It should be noted that movement of the respective proximal and distal annular rings 426 and 428 are independent from each other and, thus, either or both of the proximal end and distal ends 404 and 406 of the device 400 can be alternately collapsed and expanded.

In alternative embodiments, employment of the fixed connector 424 can be foregone. In this case, the proximal and distal slidable connectors 426 and 428 can be formed of sleeves, rather than annular rings, ensuring the structural integrity of the device 400.

Movement of the proximal and distal annular rings 426 and 428, as well as global placement of the device 400 can be accomplished through the use of threaded rods. With reference to FIG. 35, three threaded rods 450, 452, and 454 are shown. The threaded rods 450, 452, and 454 are designed to respectively engage the proximal annular ring 426, the sleeve 424, and the distal annular ring 428 (shown in FIGS. 29, 31, and 30). As can be seen, the three threaded rods 450, 452, and 454 have varying diameters, and the proximal annular ring 426, sleeve 424, and distal annular ring 428 have threaded holes 444, 446 and 448 with corresponding varying diameters. In this manner, a threaded rod can be introduced from the proximal end 404 of the device 400 to a selected one of the proximal annular ring 426, sleeve 424, and distal annular ring 428, without interference from the other two.

Specifically, the small diameter threaded rod 454 can be inserted through the larger diameter threaded holes 444 and 446 of the proximal annular ring 426 and sleeve 424, and engaged with the threaded hole 448 of the distal annular ring 428 to move the distal annular ring 428, and thus, alternately collapse and expand the distal end 406 of the device 400. The medium diameter threaded rod 452 can be inserted through the larger diameter threaded hole 444 of the proximal annular ring 426, and engaged with the threaded hole 446 of the sleeve 424 to move the sleeve 424, and thus, the entire device 400. The larger diameter threaded rod 450 can be engaged with the threaded hole 444 of the proximal annular ring 426 to move the proximal annular ring 426, and thus, alternately collapse and expand the proximal end 404 of the device 400. It should be noted that the threaded rods 450, 452, and 454 are shown in a telescoping configuration for ease in comparison. The threaded rods 450, 452, and 454, however, are used independently of each other when manipulating the proximal annular ring 426, sleeve 424, and distal annular ring 428.

Figure 36:
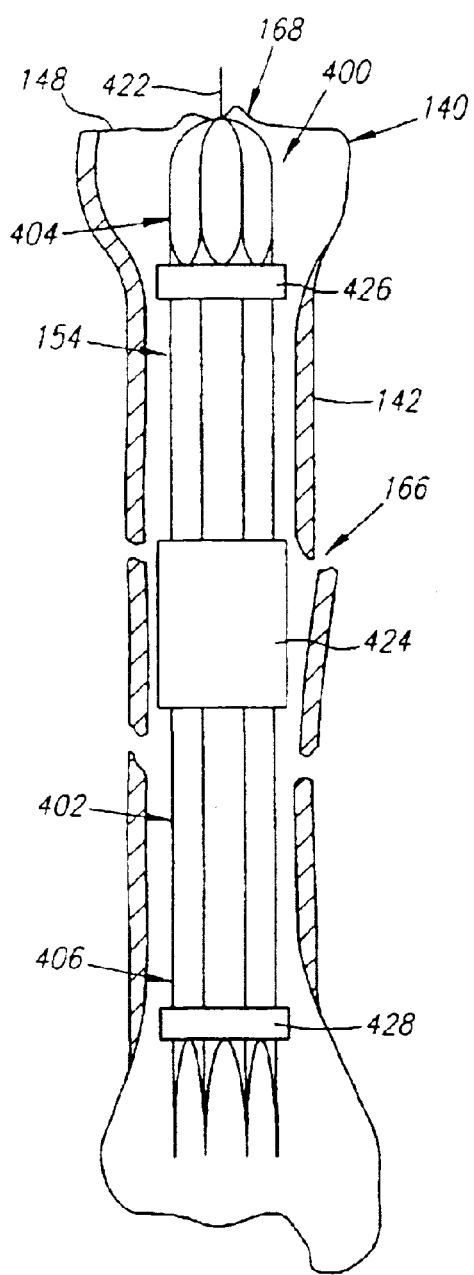
FIG. 36 is a side view of the FIG. 27 device collapsed within a tibia with a fractured shaft.
Figure 37:
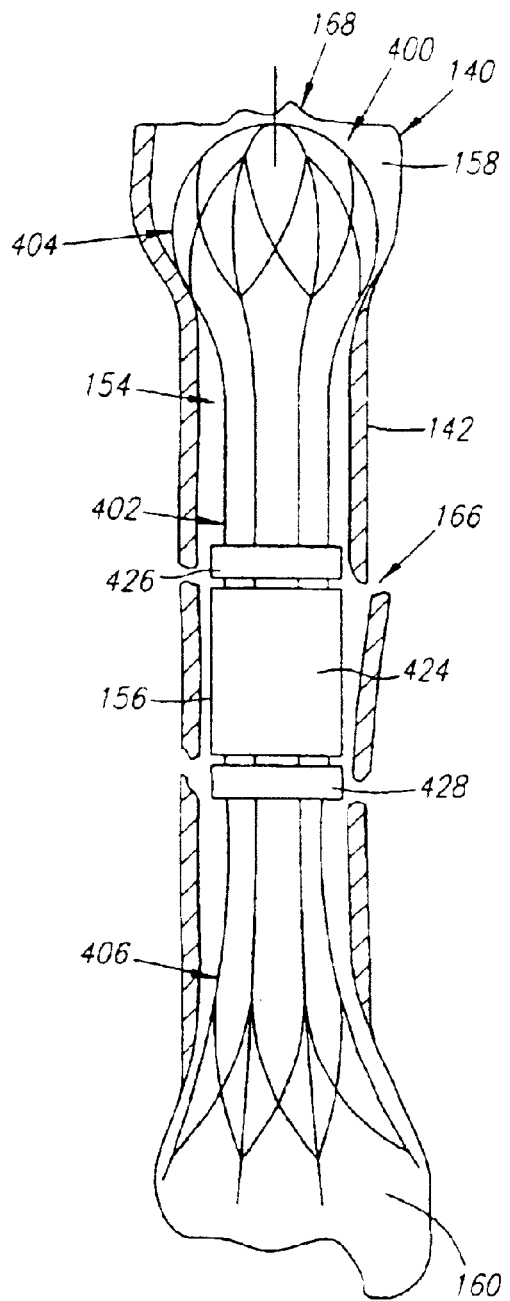
FIG. 37 is a side view of the FIG. 27 device deployed within the fractured tibia.

Like the double-ended heat-activated intramedullary device 200 described above, the double-ended self-expanding intramedullary device 400 can be advantageously used to mend bones with fractured shafts. With reference to FIGS. 36 and 37, a preferred method of deploying the device 400 within the medullary cavity 154 of a fractured tibia 140 is described. As shown, the tibia 140 has a point of fracture 166 on the shaft 142. It should be noted that the device 400 can be deployed in bones other than the tibia 140, such as the femur, fibula, humerus, ulna or radius, without straying outside the scope of the present invention.

Referring specifically to FIG. 36, prior to insertion of the device 400 within the medullary cavity 154 of the tibia 140, an opening is made through the top of the proximal epiphysis 148 to create an entry portal 168 the rein, providing access to the medullary cavity 154. The device 400 is inserted into the medullary cavity 154 of the tibia 140 in a manner similar to that described with respect to inserting the device 200 into the medullary cavity 116 of the femur 100 (FIGS. 9 and 10). That is, the device 400 can be fully collapsed within an outer sleeve (not shown) and introduced over a guide (not shown) previously inserted within the medullary cavity 154 of the tibia 140.

As shown in FIG. 36, the proximal and distal annular rings 426 and 428 are located at the respective proximal and distal ends 404 and 406 of the device 400, thereby actuating the collapsing of the device 400. The device 400 can be properly positioned within the fractured tibia 140 by engaging the sleeve 424 of the device 400 with the threaded rod 452 (shown in FIG. 35). The device 400 is positioned, such that the indicator element 422 is disposed outside the entry portal 168, thereby facilitating location of the device 400 when it is desired to extract the device 400 from the mended tibia 140.

Once the device 400 is in position, and the rotational orientation of the fractured tibia 140 is confirmed with an image intensifier, the device 400 is deployed within the medullary cavity 154 of the tibia 140. Specifically, expansion of the device 400 is actuated by moving the proximal and distal annular rings 426 and 428 towards the sleeve 424, as illustrated in FIG. 37. During expansion of the device 400, the shape of the device 400 will adopt the inner shape of the medullary cavity 154 of the tibia 140.

As illustrated in FIG. 37, the proximal and distal metaphyseal areas 158 and 160 have a greater circumference than the generally uniform circumference of the medullary canal 156. As can be seen, however, the bulbous-shaped proximal end 404 and trumpet-shaped distal end 406 of the expanded device 400 adapt to the proximal and distal metaphyseal areas 158 and 160. Thus, the larger expanded proximal and distal ends 404 and 406 firmly engage the walls of the respective proximal and distal metaphyseal areas 158 and 160 at a multitude of points, adapting to minute variations within the medullary cavity 154. The device 400, therefore, not only provides structural support to the fractured femur 100, but maintains that structural support until the femur 100 is mended.

When definitive removal of the device 400 is required, preferably when the tibia 140 is completely healed, as confirmed by radiography, a second operation is needed. The device 400 is extracted from the tibia 140 in much the same manner as that described with respect to the device 200 (FIGS. 15–17, 20–22), with the exception that collapsing of the device 400 is effected by moving the proximal and distal annular rings 426 and 428 towards the proximal and distal ends 404 and 406 of the device 400, respectively. Of course, if the device 400 is made completely of, or partially of, a bioabsorbable material, it may not be necessary to extract the device 400, or only a portion of the device 400 would have to be retrieved.

Figure 38:
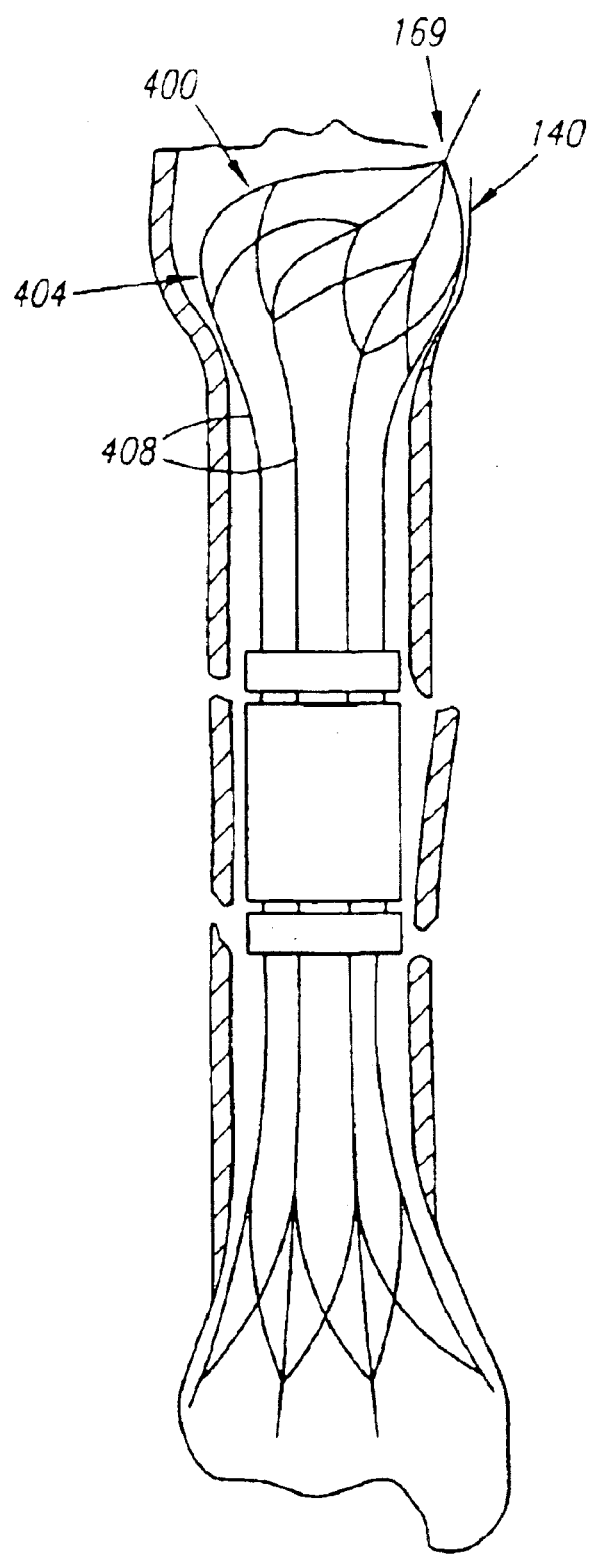
FIG. 38 is a side view of the FIG. 27 device deployed within the fractured tibia, wherein the entry portal is oblique to the longitudinal axis of the fractured tibia.

As shown in FIG. 36, the entry portal 168 is generally centered on the proximal epiphysis 148 of the tibia 140. In this case, the proximal end 404 of the expanded device 400 will be symmetrical around the longitudinal axis of the device 400 to facilitate subsequent extraction of the device 400 from the healed tibia 140. The entry portal 168 may not always be optimally centered, and in some circumstances, it may be desired to obliquely orient the entry portal 169 with respect to the proximal epiphysis 148 of the tibia 140, as shown in FIG. 38. In this case, the spine elements 408 will be configured such that the proximal end 404 of the device 400 is skewed to one side, and thus projecting towards the oblique entry portal 169. In this manner, the device 400 can be more easily extracted from the tibia 140, when healed.

A single-ended self-expanding intramedullary device 500 constructed in accordance with the present inventions, is described with reference to FIGS. 39 and 40. To the extent that the features of the device 500 are similar to those hereinbefore described, identical reference numbers have been assigned. The single-ended self-expanding intramedullary device 500, like the double-ended self-expanding intramedullary device 400, expands absent an external restraining force. Unlike the device 400, which expands at both ends, the device 500 expands only at one end.

Figure 39:
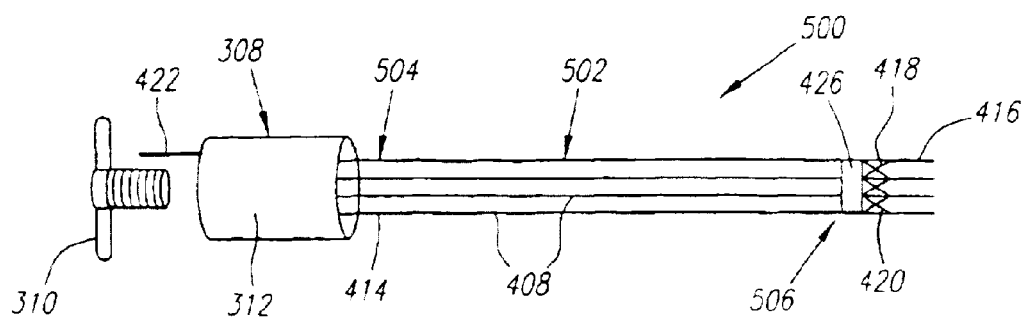
FIG. 39 is a side view of a single-ended self-expanding device in a collapsed state.
Figure 40:
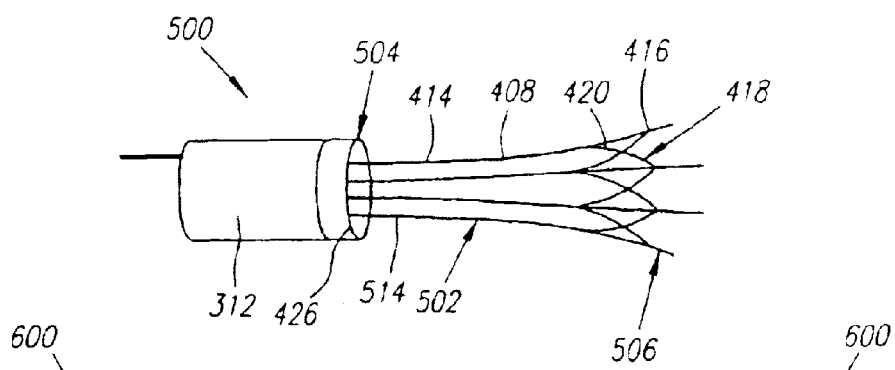
FIG. 40 is a side view of the FIG. 39 device in an expanded state.

Specifically, and with reference to FIGS. 39 and 40, the device 500 is shown in a collapsed state and an expanded state, respectively. The device 500 includes a shaft 502, a proximal end 504, and a distal end 506. The porous interconnection structure 418 which, in this embodiment, is formed by the struts 420, interconnects the spine elements 408 at the distal ends 416 thereof. The handle assembly 308, which includes the handle 310 and fixed connector 312, is formed at the proximal end 504 of the device 500. The proximal spine ends 414 are mounted to the fixed connector 312 via slots (not shown) made in the fixed connector 312, while the distal spine ends 416 are disconnected from each other. The indicator element 422 is disposed through and extends proximal to the fixed connector 312.

As illustrated in FIG. 40, the device 500, when expanded, takes the form of a trumpet shape. It should be noted, however, that the expanded device 500 can take the form of a bulbous shape when the tips of the distal spine ends 416 are connected together. Like the device 400, the spine elements 408 and struts 420 are composed of a resilient material and is configured to outwardly bend in a curve in the absence of an external restraining force, as shown in FIG. 40. In alternative embodiments, either one or the other of the spine elements 208 and struts 420 is configured to outward bend in a curve in the absence of an external restraining force.

Alternate collapse and expansion of the device 500 is actuated through movement of the slidable distal connector and, specifically, the distal annular ring 426, along the spine elements 408. As shown in FIG. 39, movement of the distal annular ring 426 towards the distal end 506 of the device 500, applies an external restraining force thereto, thereby collapsing the distal end 506 of the device 500. On the contrary, movement of the distal annular ring 426 away from the distal end 506 of the device 500, removes the external restraining force therefrom, thereby allowing expansion of the distal end 506 of the device 500. Movement of the distal annular ring 426 can be accomplished through the use of a threaded rod in a manner similar to that described above with respect to the device 400. Like the single-ended heat-activated intramedullary device 300, the single-ended self-expanding intramedullary device 500 can be advantageously used to mend bones with fractured necks, such as the neck of the femur, the head of the humerus, the olecranon, and other similar sites.

Another double-ended self-expanding intramedullary device 600 constructed in accordance with the present inventions, is described with reference to FIGS. 41 and 42. To the extent that the features of the device 600 are similar to features hereinbefore described, identical reference numbers have been assigned. This double-ended self-expanding device 600, like the double-ended self-expanding device 400 described above, expands at both ends in the absence of an external restraining force. Unlike the device 400, the shaft of which does not expand, the shaft of the device 600 does expand.

Figure 41:
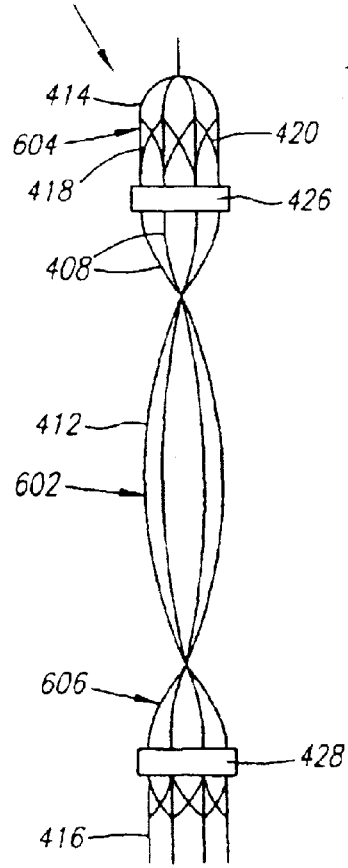
FIG. 41 is a side view of another double-ended self-expanding device in a collapsed state.
Figure 42:
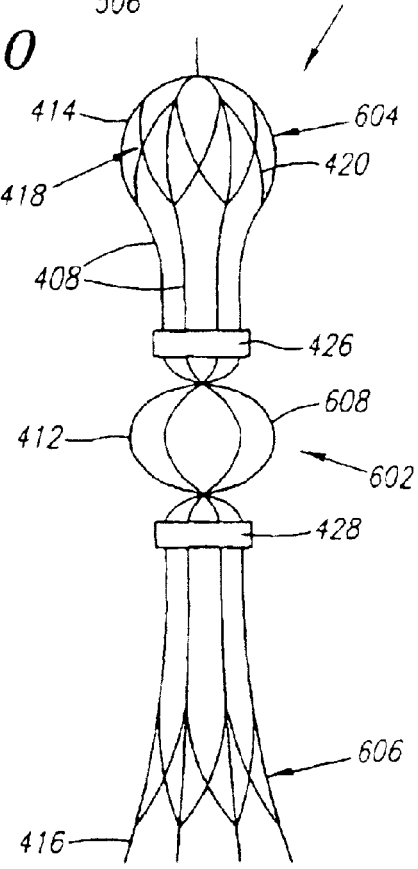
FIG. 42 is a side view of the FIG. 41 device in an expanded state.

Specifically, and with reference to FIGS. 41 and 42, the device 600 is shown in a collapsed state and an expanded state, respectively. The device 600 includes a shaft 602, a proximal end 604 and a distal end 606. The porous interconnecting structure 418 and, in particular, the struts 420, interconnect the spine elements 408 at the proximal and distal ends 414 and 416 thereof. In alternative embodiments, use of the struts 420 is foregone. As can be seen, the centers of the spine shafts 412 are not mounted to a fixed connector, and are thus free to expand.

As illustrated in FIG. 42, the device 600, when expanded, generally takes the form of an hourglass-like shape. As illustrated, the proximal end 604 of the device 600 is formed into a bulbous shape, caused by connecting the tips of the proximal spine ends 414 together. In contrast, the tips of the distal spine ends 416 are not connected together, effecting a trumpet shape at the distal end 606 of the device 600. Of course, both the proximal and distal ends 604 and 606 can be formed into either a bulbous shape or a trumpet shape. The shaft 602 of the device 600 has a sausage shape. The shapes of the expanded shaft 602, proximal end 604, and distal end 606 of the device 600 is accomplished by configuring the spine elements 408 to form a parabolic shape in the absence of an external restraining force, with an apex 608 being located at the center of the spine shafts 412. In this manner, compression of the spine shafts 412 causes the spine shafts 412 to bow outward, and removal of any external force previously applied to the proximal and distal spine ends 414 and 416 causes the proximal and distal spine ends 414 and 416 to bow outward.

Like the device 400, movement of the proximal and distal annular rings 426 and 428 actuates alternate collapse and expansion of the device 600. Specifically, movement of the proximal and distal annular rings 426 and 428 towards the respective proximal and distal ends 604 and 606 of the device 600, applies an external restraining force thereto, while removing the compressive force from the shaft 602 of the device 600. As a result, the proximal and distal ends 604 and 606, as well as the shaft 602, of the device 600 collapse. On the contrary, movement of the proximal and distal annular rings 426 and 428 away from the respective proximal and distal ends 604 and 606 of the device 600, removes the external restraining force therefrom, while applying a compressive force to the shaft 602 of the device 600. As a result, the proximal and distal ends 604 and 606, as well as the shaft 602, of the device 600 expand.

Figure 43:
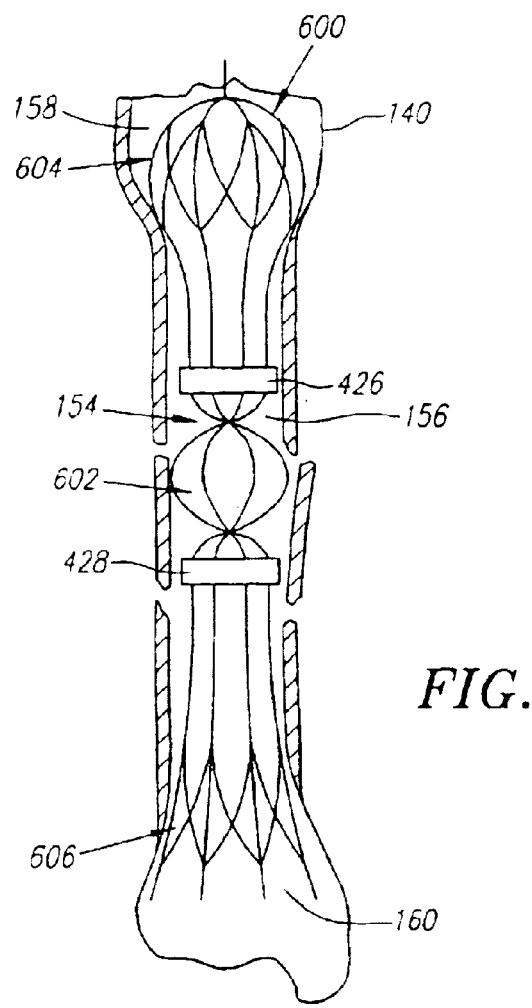
FIG. 43 is a side view of the FIG. 41 device deployed within a tibia with a fractured shaft.

Like the device 400 described above, the device 600 can be advantageously used to mend bones with fractured shafts. The device 600 is inserted into and deployed within the medullary cavity of a fractured bone in a manner similar to that described with respect to the device 400 (FIGS. 36 and 37). With reference to FIG. 43, the device 600 is shown deployed in the medullary cavity 154 of a fractured tibia 140. It should be noted, however, that the device 600 can be deployed in bones other than the tibia 140, such as the femur, fibula, humerus, ulna, or radius, without straying outside the scope of the present invention. As illustrated, the proximal and distal annular rings 426 and 428 are moved away from the respective proximal and distal ends 604 and 606 of the device 600, thereby actuating expansion of the device 600.

During expansion of the device 600, the shape of the device 600 will adopt the inner shape of the medullary cavity 154 of the tibia 140. As illustrated in FIG. 43, the proximal and distal metaphyseal areas 158 and 160 have a greater circumference than the generally uniform circumference of the medullary canal 156. As can be seen, however, the bulbous-shaped proximal end 604 and trumpet-shaped distal end 606 of the expanded device 600 adapt to the proximal and distal metaphyseal areas 158 and 160, while the sausage-shaped shaft 602 of the expanded device 600 adapts to the medullary canal 156. Thus, the larger expanded proximal and distal ends 604 and 606 firmly engage the walls of the respective proximal and distal metaphyseal areas 158 and 160, while the smaller expanded shaft 602 firmly engages the wall of the medullary canal 156, at a multitude of points, adapting to minute variations within the medullary cavity 154. The device 600, therefore, not only provides structural support to the fractured tibia 140, but maintains that structural support until the tibia 140 is mended.

Once the tibia 140 is mended, the device 600 can be extracted from the tibia 140 in a manner much like that described with respect to the device 200 (FIGS. 15–17, 20–22), with the exception that collapsing of the device 600 is effected by moving the distal annular ring 428 towards the distal end 606 of the device 600. Of course, if the device 600 is made completely of, or partially of, a bioabsorbable material, it may not be necessary to extract the device 600, or only a portion of the device 600 would have to be retrieved.

Another single-ended self-expanding intramedullary device 700 constructed in accordance with the present inventions, is described with reference to FIGS. 44 and 45. To the extent that the features of the device 700 are similar to those hereinbefore described, identical reference numbers have been assigned. The single-ended self-expanding intramedullary device 700, like the double-ended self-expanding intramedullary device 600, expands absent an external restraining force. Unlike the device 600, which expands at both ends, the device 700 expands only at one end.

Figure 44:
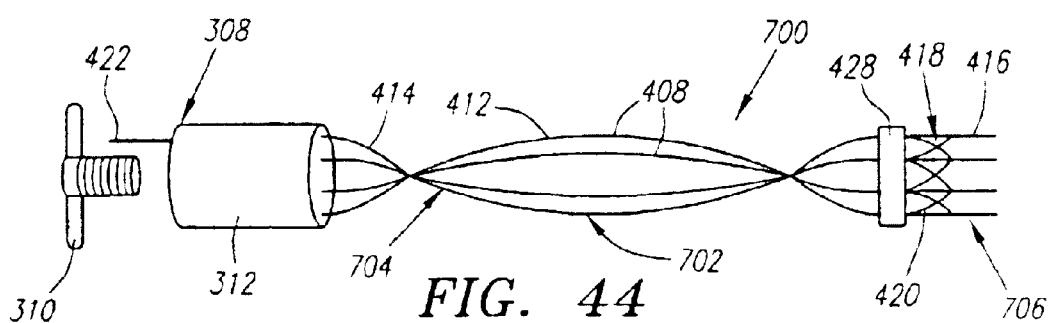
FIG. 44 is a side view of another single-ended self-expanding device in a collapsed state.
Figure 45:
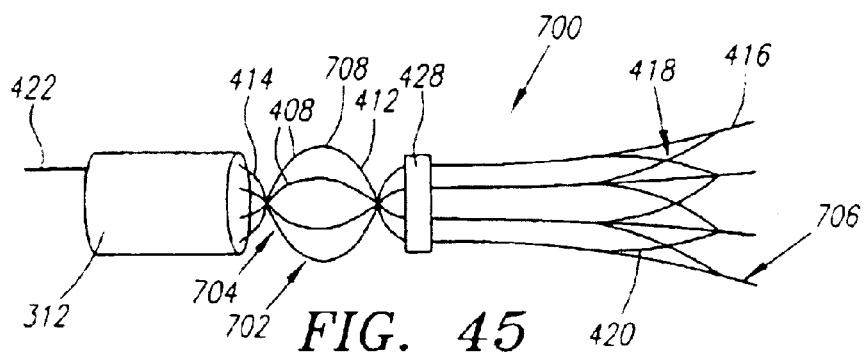
FIG. 45 is a side view of the FIG. 44 device in an expanded state.

Specifically, and with reference to FIGS. 44 and 45, the device 700 is shown in a collapsed state and an expanded state, respectively. The device 700 includes a shaft 702, a proximal end 704, and a distal end 706. The porous interconnection structure 418 which, in this embodiment, is formed by the struts 420, interconnects the spine elements 408 at the distal ends 416 thereof. The handle assembly 308, which includes the handle 310 and fixed connector 312, is formed at the proximal end 704 of the device 700. The proximal spine ends 414 are mounted to the fixed connector 312 via slots (not shown) made in the fixed connector 312, while the distal spine ends 416 are disconnected from each other. The indicator element 422 is disposed through and extends proximal to the fixed connector 312.

As illustrated in FIG. 45, the device 700, when expanded, takes the form of a trumpet shape. It should be noted, however, that the expanded device 700 can take the form of a bulbous shape when the tips of the distal spine ends 416 are connected together. The shaft 702 of the device 700 has a sausage shape. The shapes of the expanded shaft 702 and distal end 706 of the device 700 is accomplished by configuring the spine elements 408 to form a parabolic shape in the absence of an external restraining force, with an apex 708 being located at the center of the spine shaft 412. In this manner, compression of the spine shafts 412 causes the spine shafts 412 to bow outward, and removal of any external force previously applied to the distal spine ends 416 causes the distal spine end 416 to bow outward.

Alternate collapse and expansion of the device 700 is actuated through movement of the slidable distal connector and, specifically, the distal annular ring 428, along the spine elements 408. Specifically, movement of the distal annular ring 428 towards the distal ends 706 of the device 700 applies an external restraining force thereto, while removing the compressive force from the shaft 702 of the device 700. As a result, the distal end 706, as well as the shaft 702, of the device 700 collapse. On the contrary, movement of the distal annular ring 428 away from the distal end 706 of the device 700 removes the external restraining force therefrom, while applying a compressive force to the shaft 702 of the device 700. As a result, the distal end 706, as well as the shaft 702, of the device 700 expand.

Figure 46:
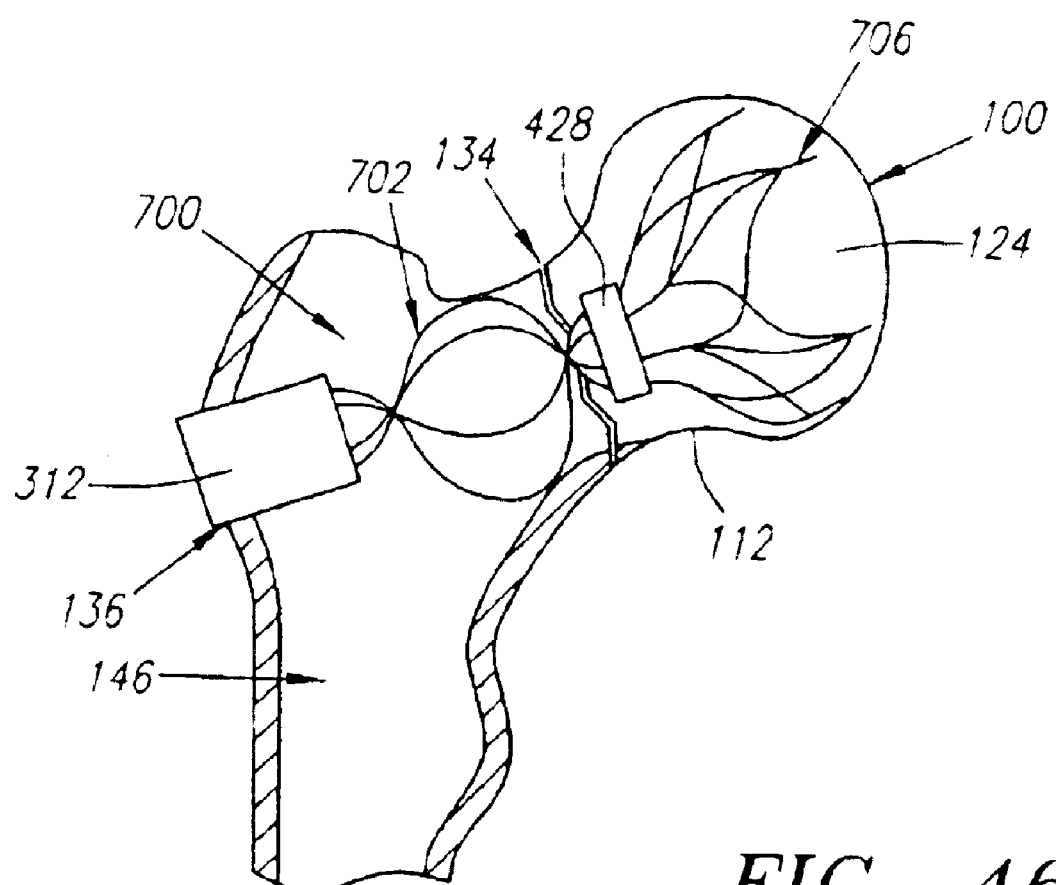
FIG. 46 is a side view of the FIG. 44 device deployed within a femur with a fractured neck.

Like the single-ended heat-activated intramedullary device 300 and single-ended self-expanding intramedullary device 500, the single-ended self-expanding intramedullary device 700 can be advantageously used to mend bones with fractures at or adjacent to their necks, such as the neck of the femur, the humerus, the olecranon, and other similar sites. With reference to FIG. 46, the device 700 is shown deployed in the medullary cavity 116 of a femur 100, after insertion thereof through the entry portal 136. The femur 100 has a point of fracture 134 on the neck 112. As illustrated, the distal annular ring 428 is moved away from the distal end 706 of the device 700, thereby actuating expansion of the device 700.

As illustrated in FIG. 46, the proximal epiphyseal area 124 has a greater circumference than the cavity within the neck 112. As can be seen, however, the trumpet-shaped distal end 706 of the expanded device 700 adapts to the distal epiphyseal area 124, while the sausage-shaped shaft 702 adapts to the cavity within the neck 112. Thus, the larger expanded distal end 706 firmly engages the walls of the proximal epiphyseal area 124, while the smaller expanded shaft 702 adapts to the walls of the neck 112, at a multitude of contact points, adapting to the minute variations within the medullary cavity 116. The firm disposition of the connector 312 within the entry portal 136 provides further stability to the fractured femur 100. The device 700, therefore, not only provides structural support to the fractured femur 100, but maintains that structural support until the femur 100 is mended.

Once the femur 100 is mended, the device 700 can be extracted from the femur 100 in a manner much like that described with respect to the device 200 (FIGS. 15–17, 20–22), with the exception that collapse of the device 700 is effected by moving the distal annular ring 428 towards the distal end 706 of the device 700. Of course, if the device 700 is made completely of, or partially of, a bioabsorbable material, it may not be necessary to extract the device 700, or only a portion of the device 700 would have to be retrieved.

Figure 47:
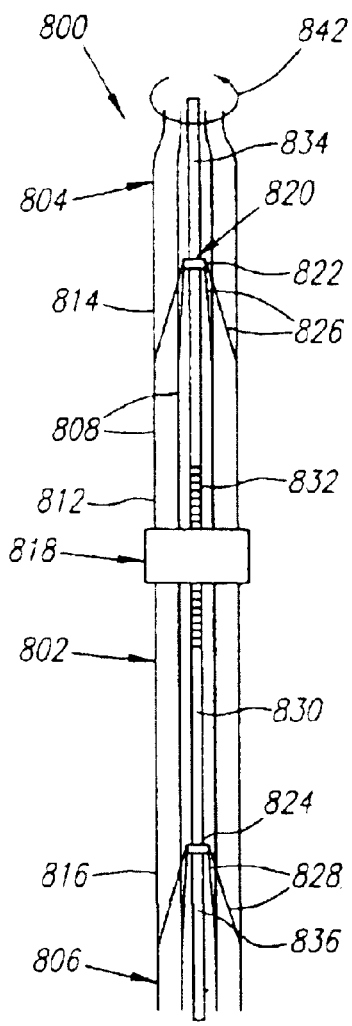
FIG. 47 is a side view of a double-ended mechanically actuated device in a collapsed state.
Figure 48:
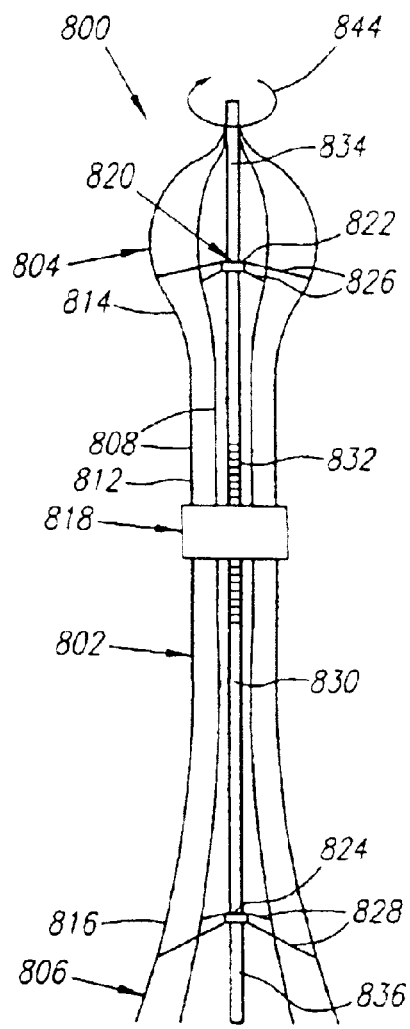
FIG. 48 is a side view of the FIG. 47 device in an expanded state.

A double-ended mechanically actuated intramedullary device 800 constructed in accordance with the present inventions, is described with reference to FIGS. 47–50. Referring specifically to FIGS. 47 and 48, the device 800 is shown in a collapsed state and an expanded state, respectively. The device 800 has a shaft 802, a proximal end 804, and a distal end 806. The device 800 is composed of a multitude of resilient spine elements 808, which are arranged in a longitudinal fashion. Each of the spine elements 808 includes a spine shaft 812, a proximal spine end 814, and a distal spine end 816. In the illustrated embodiment, the spine elements 808 have a rectangular cross-section, thereby providing the structure of the device 800 with more strength. The cross-section of the spine elements 808, however, can be any suitable geometry without straying outside the scope of the present invention.

The device 800 includes a fixed connector 818 and, in particular, a threaded sleeve, on which the spine shafts 812 are mounted. The sleeve 818 provides structural support to the device 800, and can be made longer or shorter, depending on the column strength required by the device 800 during insertion thereof into a fractured bone. In the illustrated embodiment, the spine elements 808 and sleeve 818 are formed from the same piece of material, much like the spine elements 408 and sleeve 424 described above (FIG. 34). Alternatively, the sleeve 818 can be made separately from the spine elements 808, in which case, the spine shafts 812 are suitably mounted to the sleeve 818, much like the spine elements 408 and sleeve 424 describe above (FIGS. 32 and 33). For the purposes of this specification, the spine element 808 can be represented by a single element, or can be represented by two elements separated by the fixed connector 818.

The device 800 further includes a mechanical actuator 820 for alternately collapsing and expanding the device 800. The mechanical actuator 820 is in communication with the spine elements 808 to selectively urge the proximal and distal spine ends 814 and 816 inward and outward.

Specifically, the mechanical actuator 820 includes a proximal collar 822, a distal collar 824, a multitude of proximal rigid arms 826, a multitude of distal rigid arms 828, and a threaded rod 830. The threaded rod 830 can be curved, depending on the shape of the fractured bone in which the device 800 is to be inserted. The threaded rod 830 is preferably cannulated to allow the disposition of a guide (not shown) therethrough, thereby facilitating insertion of the device 800 in the fractured bone.

The multitude of proximal rigid arms 826 are suitably mounted between the proximal collar 822 and the proximal spine ends 814. Likewise, the multitude of distal rigid arms 828 are suitably mounted between the distal collar 824 and the distal spine ends 816. Specifically, the proximal and distal rigid arms 826 and 828 and spine elements 808 are formed from the same piece of material, thereby providing an integral connection between the proximal rigid arms 826 and the proximal spine ends 814, and between the distal rigid arms 828 and the distal spine ends 816. The ends of the proximal and distal rigid arms 826 and 828 can then be attached to the respective proximal and distal collars 822 and 824 via holes (not shown) arranged circumferentially around the respective proximal and distal collars 822 and 824. In this manner, the proximal rigid arms 826 are hingedly mounted between the proximal collar 822 and the proximal spine ends 814, and the distal rigid arms 828 are hingedly mounted between the distal collar 824 and the distal spine ends 816. As will be described in further detail below, such an arrangement provides an umbrella-like effect to the proximal and distal ends 804 and 806 of the device 800.

Figure 49:
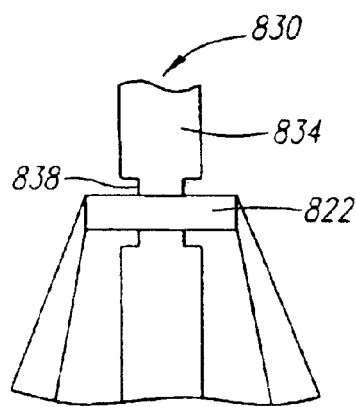
FIG. 49 is a detailed side view of a collar rotatably mounted to a threaded rod employed in the FIG. 47 device, wherein threaded rod includes a circular slot.
Figure 50:
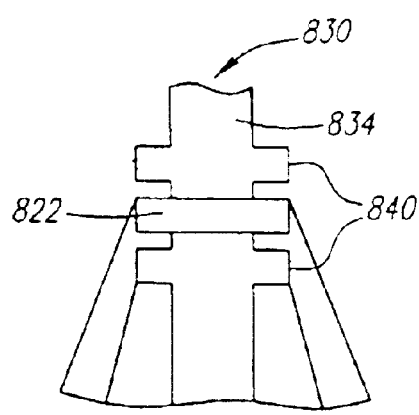
FIG. 50 is a detailed side view of a collar rotatably mounted to a threaded rod employed in the FIG. 47 device, wherein threaded rod includes a circular slot.

The threaded rod 830 includes a threaded shaft 832, which is threaded through the threaded sleeve 818. The threaded rod 830 further includes proximal and distal ends 834 and 836 on which the proximal and distal collars 822 and 824 are rotatably mounted, respectively. That is, the proximal and distal collars 822 and 824 can rotate about the threaded rod 830, but cannot be longitudinally translated relative to the threaded rod 830. FIGS. 49 and 50 illustrate two exemplary mechanical arrangements for rotatably mounting a collar to a rod.

Specifically referring to FIG. 49, the proximal end 834 of the threaded rod 830 includes a circular slot 838 in which the proximal collar 822 is mounted. Thus, the proximal collar 822 is free to rotate about the proximal end 834 of the threaded rod 830 within the circular slot 838, yet is prevented from longitudinally translating with respect to the proximal end 834 of the threaded rod 830 by the circular slot 838. Referring to FIG. 50, the proximal end 834 of the threaded rods 830 includes two opposing circular flanges 840 between which the proximal collar 822 is mounted. Thus, the proximal collar 822 is free to rotate about the proximal end 834 of the threaded rod 830 between the opposing circular flanges 840, yet is prevented from longitudinally translating with respect to the proximal end 834 of the threaded rod 830 by the opposing circular flanges 840.

Referring to FIG. 47, rotation of the threaded rod 830 in a first direction 842 longitudinally translates the threaded rod 830, and thus the proximal collar 822, proximally in relation to the spine elements 808, which are fixed in placed by the threaded sleeve 818. Proximal movement of the proximal collar 822 exerts a tensile force on the proximal rigid arms 828, which in turn pulls the proximal end 814 of the spine elements 808 inward, collapsing the proximal end 804 of the device 800. As the angle between the proximal arms 826 and the proximal ends 814 of the spine elements 808 decreases with proximal movement of the proximal collar 822, the proximal end 804 of the device 800 further collapses.

Rotation of the threaded rod 830 in the first direction 842 also longitudinally translates the distal collar 824 proximally in relation to the spine elements 808. Proximal movement of the distal collar 824 exerts a tensile force on the proximal rigid arms 828, which in turn pulls the distal end 816 of the spine elements 808 inward, collapsing the distal end 806 of the device 800. As the angle between the distal arms 828 and the distal ends 816 of the spine elements 808 decreases with proximal movement of the distal collar 824, the distal end 806 of the device 800 further collapses.

Referring to FIG. 48, rotation of the threaded rod 830 in a second opposite direction 844 longitudinally translates the threaded rod 830, and thus the proximal collar 822, distally in relation to the spine elements 808. Distal movement of the proximal collar 822 exerts a compressive force on the proximal rigid arms 828, which in turn pushes the proximal end 814 of the spine elements 808 outward, expanding the proximal end 804 of the device 800. As the angle between the proximal arms 826 and the proximal ends 814 of the spine elements 808 increases with distal movement of the proximal collar 822, the proximal end 804 of the device 800 further expands.

Rotation of the threaded rod 830 in the second direction 844 also longitudinally translates the distal collar 824 distally in relation to the spine elements 808. Distal movement of the distal collar 824 exerts a compressive force on the proximal rigid arms 828, which in turn, pushes the distal end 816 of the spine elements 808 outward, expanding the distal end 806 of the device 800. As the angle between the distal arms 828 and the distal ends 816 of the spine elements 808 increases with distal movement of the distal collar 824, the distal end 806 of the device 800 further expands.

As illustrated in FIG. 48, the device 800, when expanded, generally takes the form of an hourglass-like shape. As illustrated, the proximal end 804 of the device 800 is formed into a bulbous shape, caused by pre-shaping the proximal spine ends 814 in a slightly outwardly bowed shape. In contrast, the distal end 806 of the device 800 is formed into a trumpet shape. Of course, both the proximal and distal ends 804 and 806 can be formed into either a bulbous shape or a trumpet shape.

Figure 51:
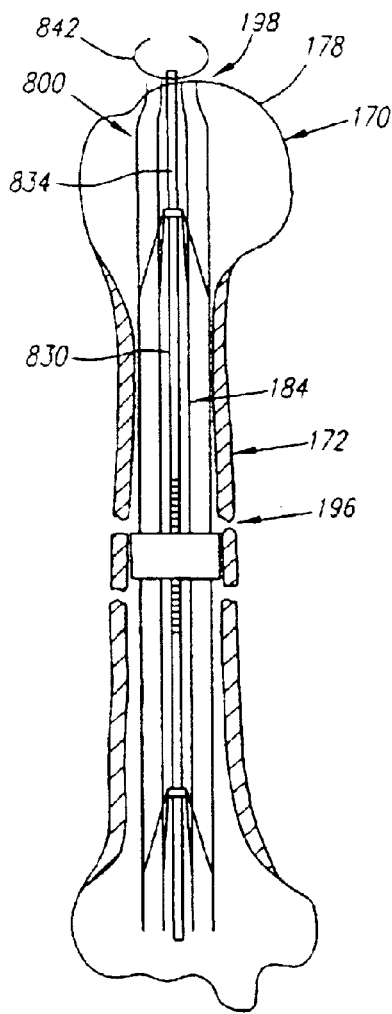
FIG. 51 is a side view of the FIG. 47 device collapsed within a humerus with a fractured shaft.
Figure 52:
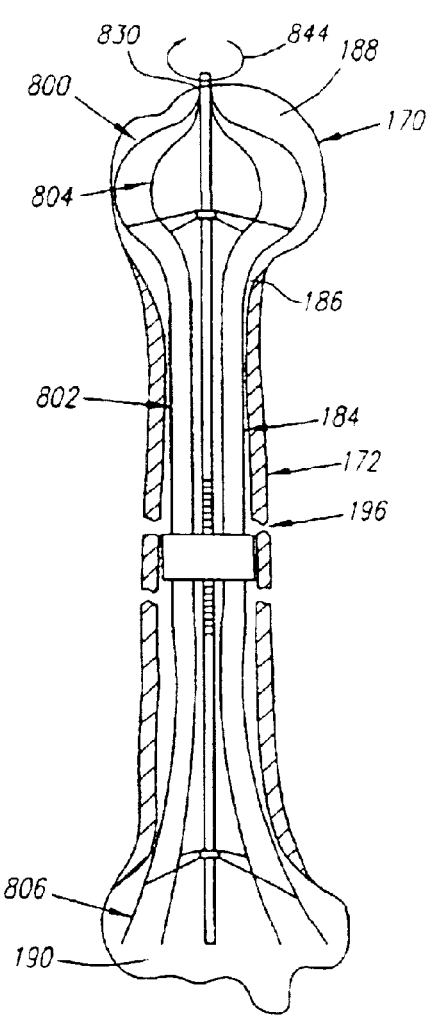
FIG. 52 is a side view of the FIG. 47 device deployed within the fractured humerus.

Like the double-ended heat-activated intramedullary device 200 and the double-ended self-expanding intramedullary devices 400 and 600 described above, the double-ended mechanically actuated intramedullary device 800 can be advantageously used to mend bones with fractured shafts. With reference to FIGS. 51 and 52, a preferred method of deploying the device 800 within the medullary cavity 184 of a fractured humerus 170 is described. As shown, the humerus 170 has a point of fracture 196 on the shaft 172. It should be noted that the device 800 can be deployed in bones other than the humerus 170, such as the femur, fibula, tibia, ulna, or radius, without straying outside the scope of the present invention.

Referring specifically to FIG. 51, prior to insertion of the device 800 within the medullary cavity 184 of the tibia 170, an opening is made through the top of the proximal epiphysis 178 to create an entry portal 198 therein, providing access to the medullary cavity 184. The device 800 is inserted into the medullary cavity 184 of the tibia 170 in a manner similar to that described with respect to inserting the device 200 into the medullary cavity 116 of the femur 100 (FIGS. 9 and 10) or the device 400 into the medullary cavity 154 of the tibia 140 (FIGS. 36 and 37). That is, the device 400 can be fully collapsed within an outer sleeve (not shown) and introduced over a guide (not shown) previously inserted within the medullary cavity 184 of the tibia 170.

As shown in FIG. 51, the threaded rod 830 is rotated in the first direction 842, thereby actuating the collapse of the device 800. The device 800 can be properly positioned within the humerus 170 by manipulating the proximal end of the threaded rod 830. The device 800 is positioned, such that the proximal end of the threaded rod 830, which also acts as an indicator element, is disposed outside the entry portal 198, thereby facilitating location of the device 800 when it is desired to extract the device 800 from the mended humerus 170. It should be noted that a portion of the threaded rod 830 or indicator rod, can be cutoff if the indicator rod extends too far out the entry portal 198, in which case a rounded nut can then be placed over the end of the indicator rod.

Once the device 800 is in position, and the rotational orientation of the fractured humerus 170 is confirmed with an image intensifier, the device 800 is deployed within the medullary cavity 184 of the humerus 170. Specifically, expansion of the device 800 is actuated by rotating the threaded rod 830 in the second direction 844, as illustrated in FIG. 52. During expansion of the device 800, the shape of the device 800 will adopt the inner shape of the medullary cavity 184 of the humerus 170.

As illustrated in FIG. 52, the proximal and distal metaphyseal areas 188 and 190 have a greater circumference than the generally uniform circumference of the medullary canal 186. As can be seen, however, the bulbous-shaped proximal end 804 and trumpet-shaped distal end 806 of the expanded device 800 adapt to the proximal and distal metaphyseal areas 188 and 190. Thus, the larger expanded proximal and distal ends 804 and 806 firmly engage the walls of the respective proximal and distal metaphyseal areas 188 and 190 at a multitude of points, adapting to minute variations within the medullary cavity 184. The device 800, therefore, not only provides structural support to the fractured humerus 170, but maintains that structural support until the humerus 170 is mended.

When definitive removal of the device 800 is required, preferably when the humerus 170 is completely healed, as confirmed by radiography, a second operation is needed. The device 800 is extracted from the humerus 170 in much the same manner as that described with respect to the device 200 (FIGS. 15–17, 20–22), with the exception that collapse of the device 800 is effected by rotating the threaded rod 830 in the first direction 842. Of course, if the device 800 is made completely of, or partially of, a bioabsorbable material, it may not be necessary to extract the device 800, or only a portion of the device 800 would have to be retrieved.

A single-ended mechanically actuated intramedullary device 900 constructed in accordance with the present inventions, is described with reference to FIGS. 53 and 54. To the extent that the features of the device 900 are similar to those hereinbefore described, identical reference numbers have been assigned. The single-ended mechanically actuated intramedullary device 900, like the double-ended mechanically actuated intramedullary device 800, expands when used with a mechanical actuator. Unlike the device 800, which expands at both ends, the device 900 expands only at one end.

Figure 53:
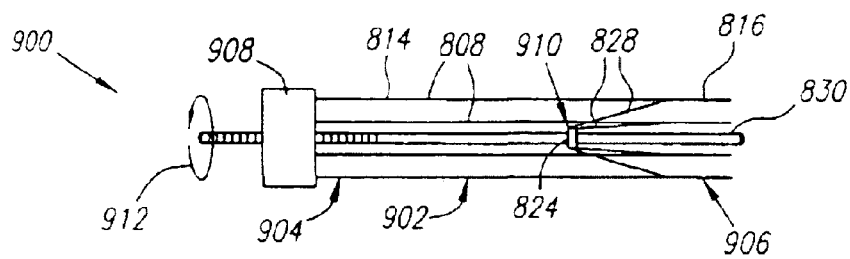
FIG. 53 is a side view of a single-ended mechanically actuated device in a collapsed state.
Figure 54:
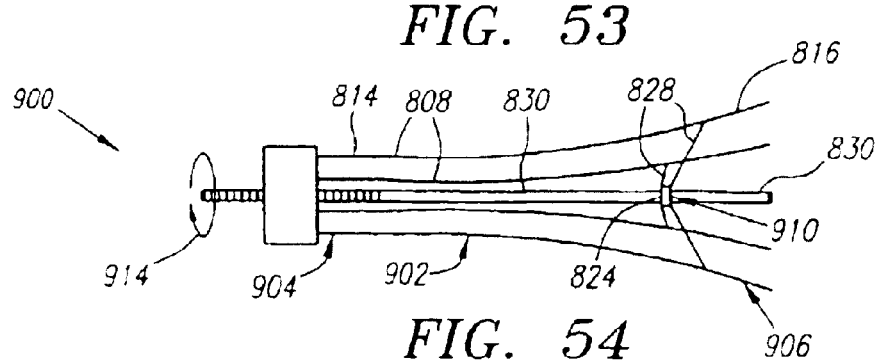
FIG. 54 is a side view of the FIG. 53 device in an expanded state.
Figure 59:
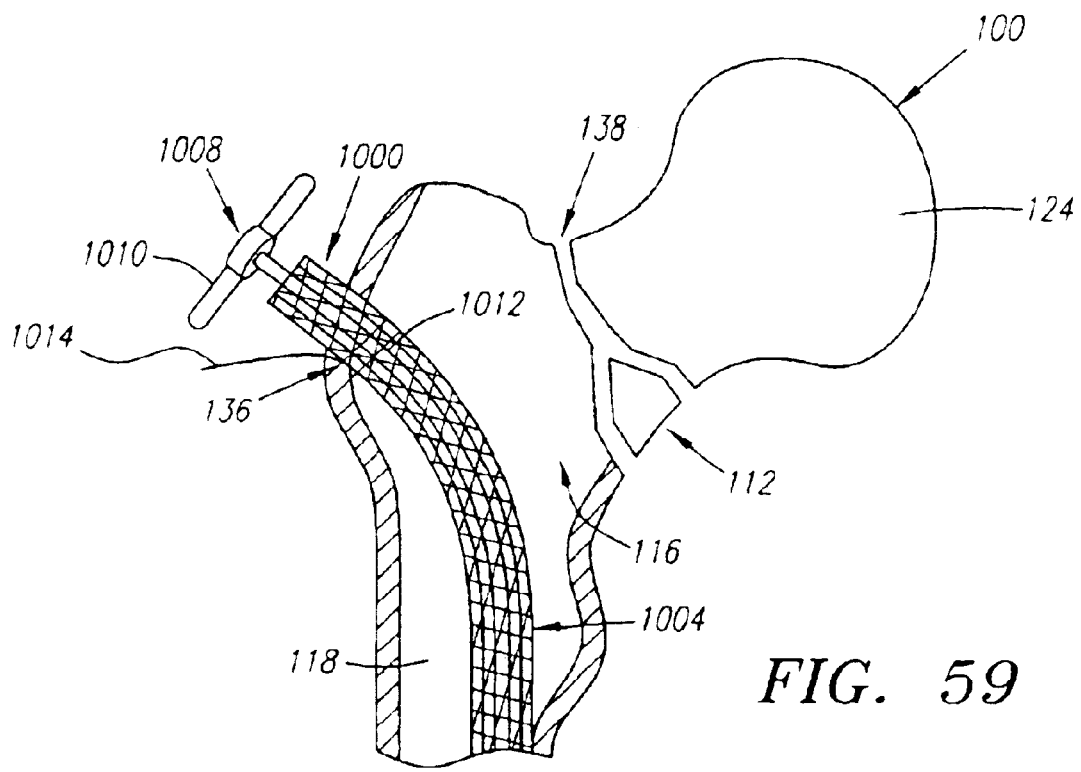
FIG. 59 is a side view of the FIG. 57 device collapsed within a femur with a fractured neck, wherein the device is shown partially inserted in the medullary canal during manipulation with a removable handle assembly.

FIGS. 53 and 54 illustrate the device 900 in a collapsed state and an expanded state, respectively. The device 900 includes a shaft 902, a proximal end 904, and a distal end 906. The device 900 further includes a fixed connector and, in particular, a threaded sleeve 908. The proximal spine ends 814 are mounted to the threaded sleeve 908 via slots (not shown) made in the threaded sleeve 908. The device 900 further includes a mechanical actuator 910 for alternately collapsing and expanding the device 900. The mechanical actuator 910 is in communication with the spine elements 808 to selectively urge the distal spine ends 814 inward and outward. Specifically, the device 900 includes the distal collar 824, the multitude of distal arms 828, and the threaded rod 830. The multitude of distal rigid arms 828 are hingedly mounted between the distal collar 824 and the distal spine ends 816, thereby providing an umbrella-like effect to the distal end 906 of the device 900, as will be described in further detail below. The threaded rod 830 is threaded through the threaded sleeve 908 and distal collar 824.

As illustrated in FIG. 53, rotation of the threaded rod 830 in a first direction 912 longitudinally translates the threaded rod 830, and thus the distal collar 824, proximally in relation to the spine elements 808. Proximal movement of the distal collar 824 exerts a tensile force on the proximal rigid arms 828, which in turn pulls the distal end 816 of the spine elements 808 inward, collapsing the distal end 906 of the device 900. As the angle between the distal arms 828 and the distal ends 816 of the spine elements 808 decreases with proximal movement of the distal collar 824, the distal end 906 of the device 900 further collapses.

As illustrated in FIG. 54, rotation of the threaded rod 830 in a second opposite direction 914 longitudinally translates the threaded rod 830, and thus the distal collar 824, distally in relation to the spine elements 808. Distal movement of the distal collar 824 exerts a compressive force on the proximal rigid arms 828 which in turn, pushes the distal end 816 of the spine elements 808 outward, expanding the distal end 906 of the device 900. As the angle between the distal arms 828 and the distal ends 816 of the spine elements 808 increases with distal movement of the distal collar 824, the distal end 906 of the device 900 further expands.

As illustrated in FIG. 54, the device 900, when expanded, takes the form of a trumpet shape. It should be noted, however, that the expanded device 900 can take the form of a bulbous shape by pre-shaping the distal spine ends 816 in a slightly outwardly bowed shape.

Like the single-ended heat-activated intramedullary device 300, and single-ended self-expanding intramedullary devices 500 and 700, the single-ended mechanically actuated intramedullary device 900 can be advantageously used to mend bones with fractured necks, such as the neck of the femur, the neck of the humerus, the olecranon, and other similar sites.

With reference to FIGS. 55 and 56, a preferred method of deploying the intramedullary device 900 within the medullary cavity 184 of a fractured humerus 170 is described. The humerus 170 is shown with a point of fracture 199 on the neck 174. It should be noted, however, that the device 900 can be deployed in bones other than the humerus 170, such as the neck of the femur, the olecranon, and other similar sites, without straying outside the scope of the present invention.

Referring specifically to FIG. 55, prior to insertion of the device 900 within the medullary cavity 184 of the humerus 170, an opening is made through the side of or below the neck 174 to create an entry portal 197 therein, providing access to the medullary cavity 184. The device 900, with an insertion sleeve (not shown), is then introduced over a guide (not shown) into the humerus 170 through the entry portal 197. The sleeve 908 is firmly located within the entry portal 197. As shown, the threaded rod 830 is rotated in the first direction 912, thereby actuating the collapse of the device 900. The device 900 is properly positioned within the neck 195 and head 192 of the humerus 170, such that the proximal end of the threaded rod 830, which also acts as an indicator element, is disposed outside the entry portal 197, thereby facilitating location of the device 900 when it is desired to extract the device 900 from the mended humerus 170. It should be noted that a portion of the threaded rod 830 or indicator rod, can be cutoff if the indicator rod extends too far out the entry portal 197, in which case a rounded nut can then be placed over the end of the indicator rod.

Once the device 900 is in position, and the rotational orientation of the fractured humerus 170 is confirmed with an image intensifier, the device 900 is deployed within the medullary cavity 184 of the humerus 170, as illustrated in FIG. 56. Deployment of the device 900 is accomplished much like deployment of the device 800, described above. That is, the threaded rod 830 is rotated in the second direction 914.

As illustrated in FIG. 56, the trumpet-shaped distal end 906 of the expanded device 900 adapts to the proximal metaphyseal area 188. Thus, the expanded distal end 906 firmly engages the walls of the proximal metaphyseal area 188 at a multitude of contact points, while adapting to minute variations within the medullary cavity 184. The firm disposition of the connector 908 within the entry portal 197 provides further stability to the fractured humerus 170. The device 900, therefore, not only provides structural support to the fractured humerus 170, but maintains that structural support until the humerus 170 is mended.

Once the humerus 170 is mended, the device 900 is extracted from the humerus 170 in much the same manner as that described with respect to the device 200 (FIGS. 15–17, 20–22), with the exception that collapse of the device 900 is effected by rotating the threaded rod 830 in the first direction 912. Of course, if the device 900 is made completely of, or partially of, a bioabsorbable material, it may not be necessary to extract the device 900, or only a portion of the device 900 would have to be retrieved.

A manipulatable single-end heat-activated intramedullary device 1000 constructed in accordance with the present inventions, is described with reference to FIGS. 57 and 58. To the extent that the features of the device 1000 are similar to those hereinbefore described, identical reference numbers have been assigned. The single-ended heat-activated intramedullary device 1000, like the single-ended heat-activated intramedullary device 300, described above, expands at one end when subjected to a temperature above the shape transitional temperature. Unlike the device 300, the other end of the device 300 is not connected to a handle assembly.

Specifically, and with reference to FIGS. 57 and 58, the device 1000 is shown in a collapsed state and an expanded state, respectively. The device 1000 includes a shaft 1002, a proximal end 1004, and a distal end 1006. The porous interconnection structure 218 which, in this embodiment, is formed by the mesh 220, interconnects the spine elements 208. Again, the interconnection structure 218 can take the form of a structure other than the mesh 220 and need not extend the entire length of the spine elements 208.

The device 1000 further includes a removable handle assembly 1008, which includes a handle 1010 and a flexible rod 1012. The flexible rod 1012 is longitudinally disposed through the center of the device 1000, and is formed of a flexible material, such as elastic. The device 1000 further includes a flexible cable 1014, which is suitably mounted to the spine elements 208 and interconnection structure 208 at the shaft 1002 of the device 1000.

As illustrated in FIG. 58, the device 1000, when expanded, takes the form of a trumpet shape. The spine elements 208 and mesh 220 are formed of a shape memory alloy to actuate expansion of the device 1000. The spine elements 208 are configured to outwardly bend in a curve and the mesh 220 is configured to expand outward when exposed to a temperature greater than the shape transitional temperature of the shape memory alloy, thereby effecting the shape of the expanded device 1000, as shown in FIG. 58. In alternative embodiments, either one or the other of the spine elements 208 and mesh 220 is formed of a shape memory alloy.

The device 1000 can be advantageously used to mend bones with fractured necks. With reference to FIGS. 59–63, a preferred method of deploying the intramedullary device 1000 within the medullary cavity 116 of a fractured femur 100 is described. The femur 100 is shown with a compound fracture 138 on the neck 112. It should be noted, however, that the device 1000 can be deployed in bones other than the femur 100, such as the head of the humerus, the olecranon, and other similar sites, without straying outside the scope of the present invention.

Figure 60:
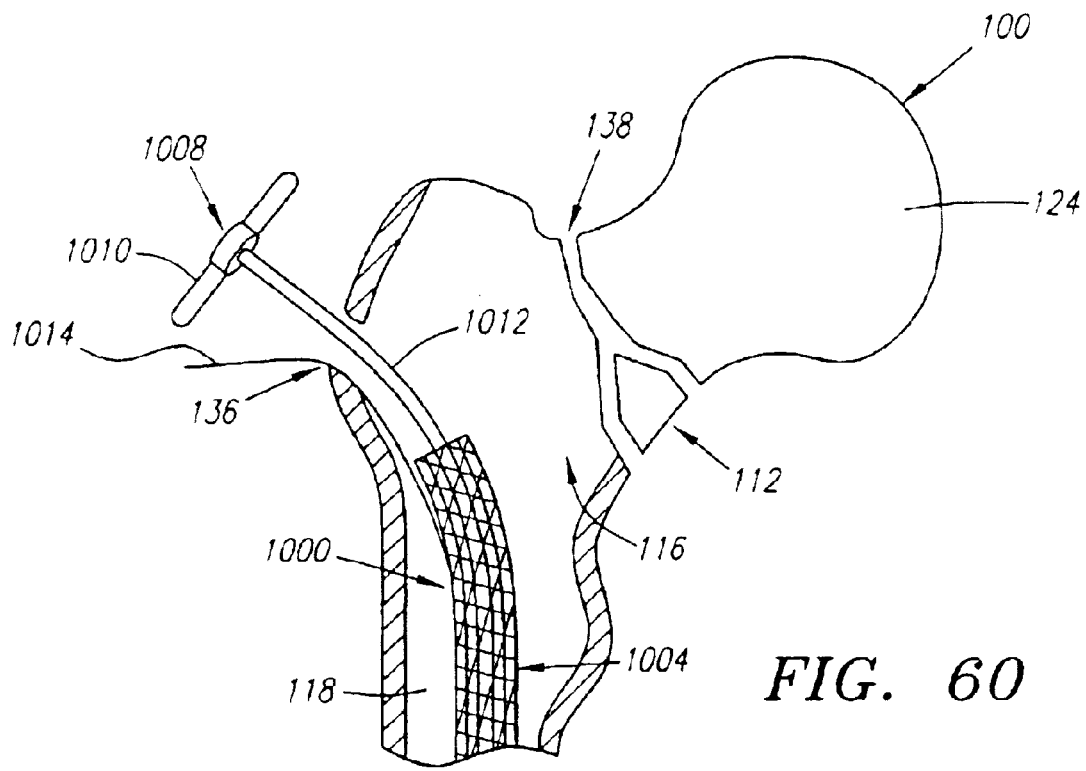
FIG. 60 is a side view of the FIG. 57 device collapsed within the fractured femur, wherein the device is fully inserted in the medullary canal after manipulation with the removable handle assembly.

First, the proximal end 1004 of the device 1000 is inserted through a previously formed entry portal 136 and distally into the medullary canal 118 (FIG. 59) until the device 1000 is completely inside the medullary canal 118, with the handle 1010 and end of the cable 1014 disposed outside the entry portal 136 (FIG. 60). As illustrated, the flexibility of the device 1000, including the rod 1012 of the handle assembly 1008, allows the device 1000 to be advanced through the medullary canal 118, despite the substantially transverse relationship between the longitudinal axis of the medullary canal 118 and the entry portal 136.

Figure 61:
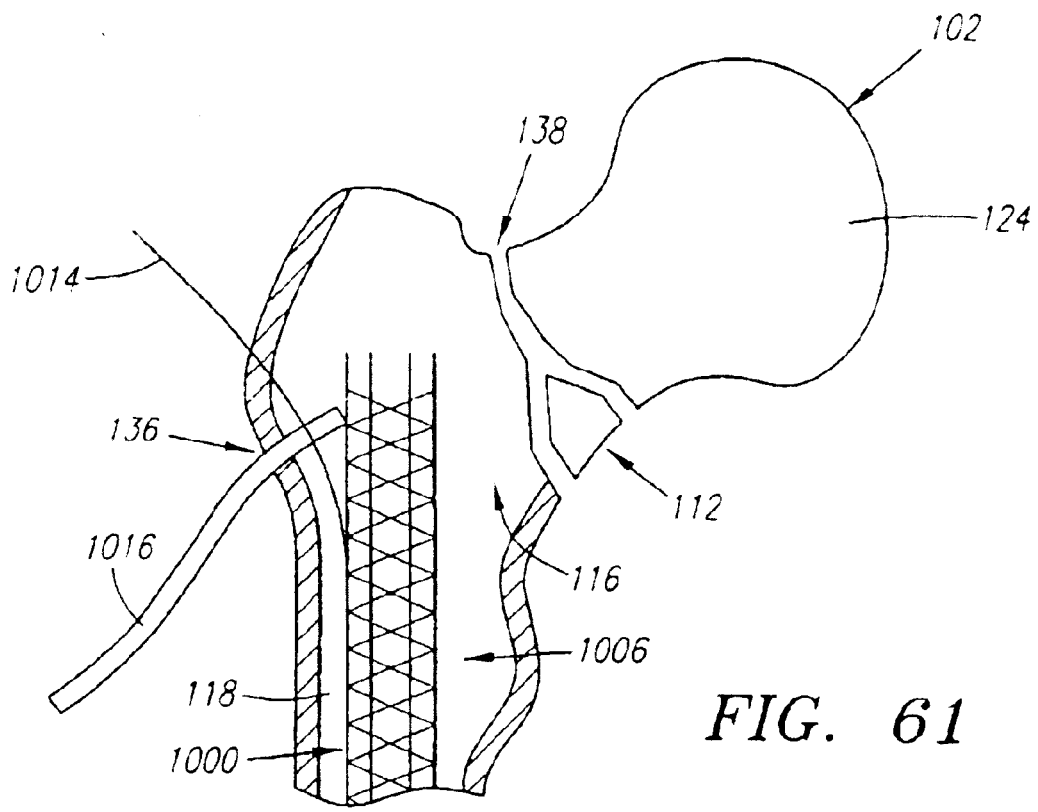
FIG. 61 is a side view of the FIG. 57 device collapsed within the fractured femur, wherein the handle assembly is removed and a tool is shown in contact with the distal end of the FIG. 57 device.
Figure 62:
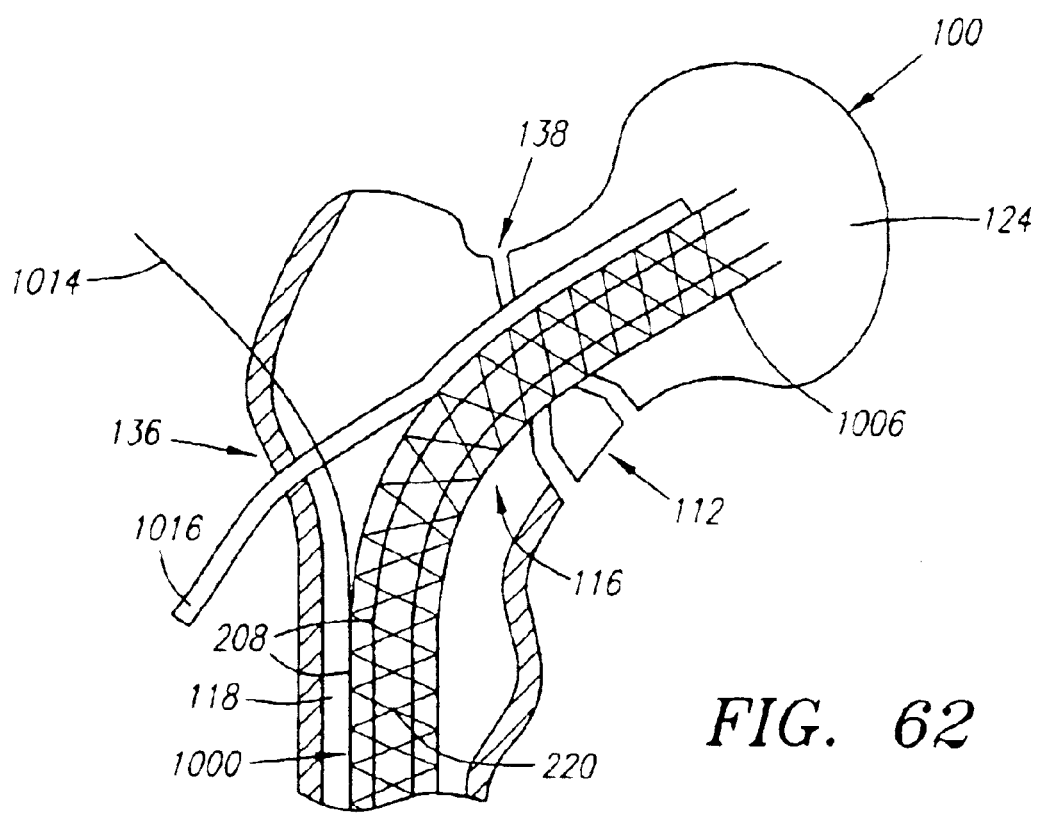
FIG. 62 is a side view of the FIG. 57 device collapsed within the fractured femur, wherein the shaft of the device is being pulled, while the distal end of the device is being directed towards the neck of the femur.

Once the device 1000 is fully inserted within the medullary canal 118, the handle assembly 1008 is removed, and an elongate tool, such as a rigid strip 1016 is then inserted through the entry portal 136 until the end of the strip 1016 rests against the distal end 1006 of the device 1000 (FIG. 61). Preferably, the rigid strip 1016 is curved and is relatively wide enough to effect intimate contact with the device 1000. The strip 1016 is then pushed to angle the distal end 1006 of the device 1000 towards the neck 112 of the femur 100, and the cable 1014 is pulled to advance the distal end 1006 of the device 1000 through the neck 112 and into the proximal epiphyseal area 124 (FIG. 62).

Figure 63:
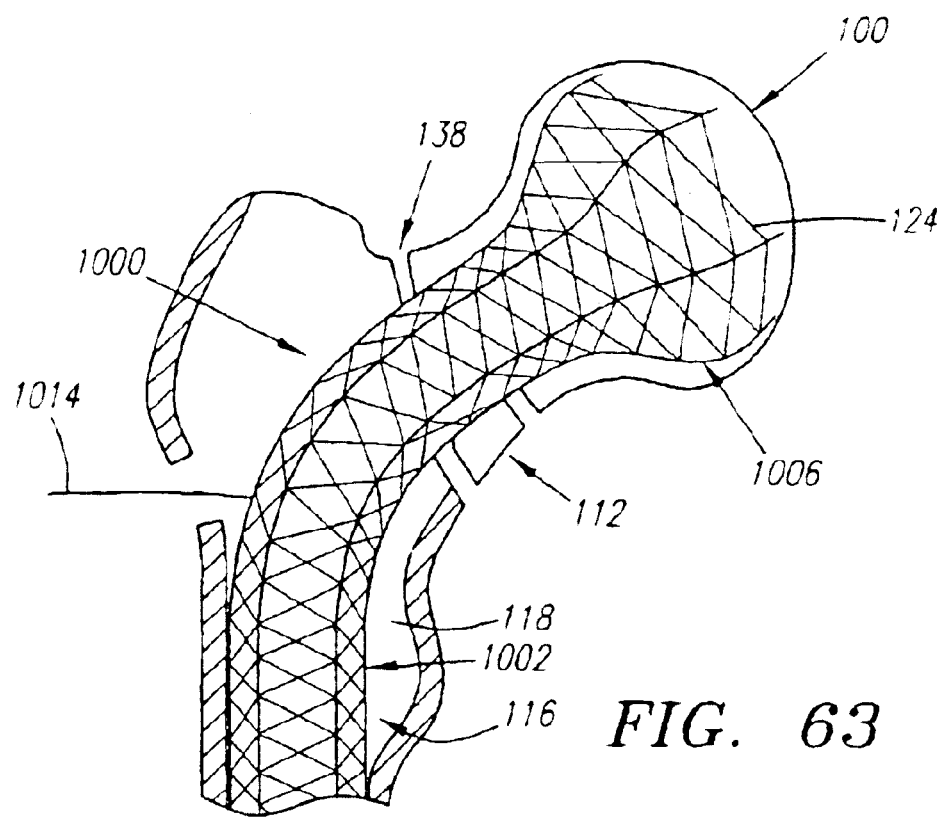
FIG. 63 is a side view of the FIG. 57 device deployed within the fractured femur.

Once the device 1000 is in position, and the rotational orientation of the fractured femur 100 is confirmed with an image intensifier, the device 1000 is deployed within the medullary cavity 116 of the femur 100 (FIG. 63). Deployment of the device 1000 can be accomplished by heating the spine elements 208 and mesh 220 to a temperature above the shape transitional temperature of the shape memory alloy. The cable 1014 can be conveniently used to conduct the heat to the device 1000. After deployment of the device 1000, the cable 1014 can then be removed.

As illustrated in FIG. 63, the trumpet-shaped distal end 1006 of the expanded device 1000 adapts to the proximal epiphyseal area 124. Thus, the larger expanded distal end 1006 firmly engages the walls of the proximal epiphyseal area 124 at a multitude of contact points, while adapting to minute variations within the medullary cavity 116. Additionally, the expanded shaft 1002 firmly engages the walls of the medullary canal 118, providing further stability to the fractured femur 100, which may necessitate maximum stability due to the compound fracture 138. The device 1000, therefore, not only provides structural support to the fractured femur 100, but maintains that structural support until the femur 100 is mended.

It should be noted that in situations in which the shaft 102, as well as the neck 112, of the femur 100 is fractured, the device 1000 can be made long enough, such that the proximal end 1002 extends past the shaft fracture, preferably into the distal metaphyseal area 126 of the femur 100.

A secondary heat-activated intramedullary device 1100 constructed in accordance with the present inventions, is described with reference to FIGS. 64 and 65. To the extent that the features of the device 1100 are similar to those hereinbefore described, identical reference numbers have been assigned. The heat-activated intramedullary device 1100, like the single-ended heat-activated intramedullary device 300 described above, expands when subjected to a temperature above the shape transitional temperature. Unlike the device 300, the other end of the device 300 is not connected to a handle assembly.

Figure 64:
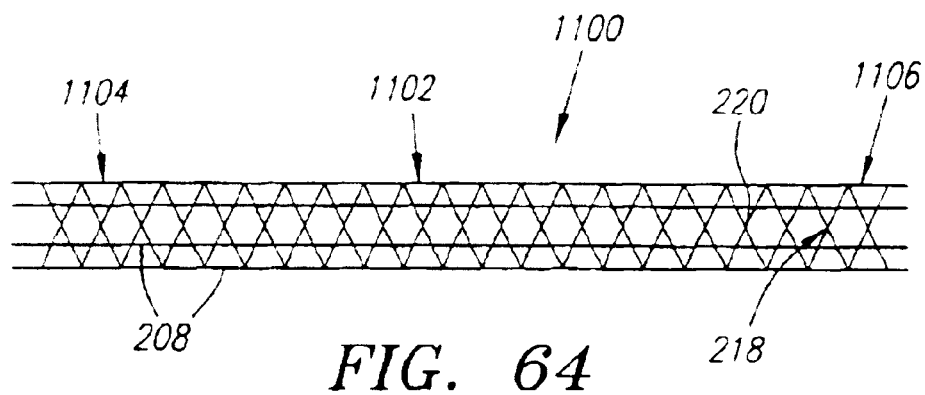
FIG. 64 is a side view of a secondary heat-activated intramedullary device in a collapsed state.
Figure 65:
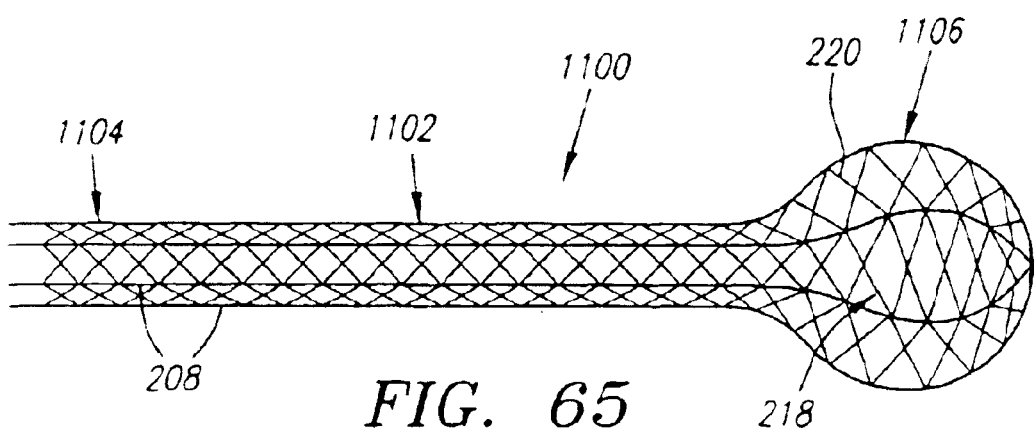
FIG. 65 is a side view of the FIG. 64 device in an expanded state.

Specifically, and with reference to FIGS. 64 and 65, the device 1100 is shown in a collapsed state and an expanded state, respectively. The device 1100 includes a shaft 1102, a proximal end 1104, and a distal end 1106. The porous interconnection structure 218 which, in this embodiment, is formed by the mesh 220, interconnects the spine elements 208. Again, the interconnection structure 218 can take the form of a structure other than the mesh 220 and need not extend the entire length of the spine elements 208.

As illustrated in FIG. 65, the device 1100, when expanded, takes the form of a bulbous shape. The spine elements 208 and mesh 220 are formed of a shape memory alloy to actuate expansion of the device 1100. The spine elements 208 are configured to outwardly bend in a curve and the mesh 220 is configured to expand outward when exposed to a temperature greater than the shape transitional temperature of the shape memory alloy, thereby effecting the shape of the expanded device 1100, as shown in FIG. 58. In alternative embodiments, either one or the other of the spine elements 208 and mesh 220 is formed of a shape memory alloy.

Alternatively, the device 1100, when expanded, takes the form of a cylindrical shape, in which case the spine elements 208 are configured to maintain a rectilinear configuration. More alternatively, the device 1100 can be expanded in a manner other than heat activation. For example, the device 1100 can be self-expanding or include a mechanical actuator, as previously described with other embodiments above.

The device 1100 can be advantageously used, in conjunction with a single-ended intramedullary device, such as the single-ended heat-activated intramedullary device 300, single-ended self-expanding intramedullary devices 500 and 700, or the single-ended mechanically actuated device 900, to mend bones with fractured necks. With reference to FIGS. 66–69, a preferred method of deploying the intramedullary device 1100, along with the single-ended heat-activated intramedullary device 300, within the medullary cavity 116 of a fractured femur 100 is described. The femur 100 is shown with a compound fracture 138 on the neck 112. It should be noted, however, that the devices 1100 and 300 can be deployed in bones other than the femur 100, such as the head of the humerus, the olecranon, and other similar sites, without straying outside the scope of the present invention.

Figure 66:
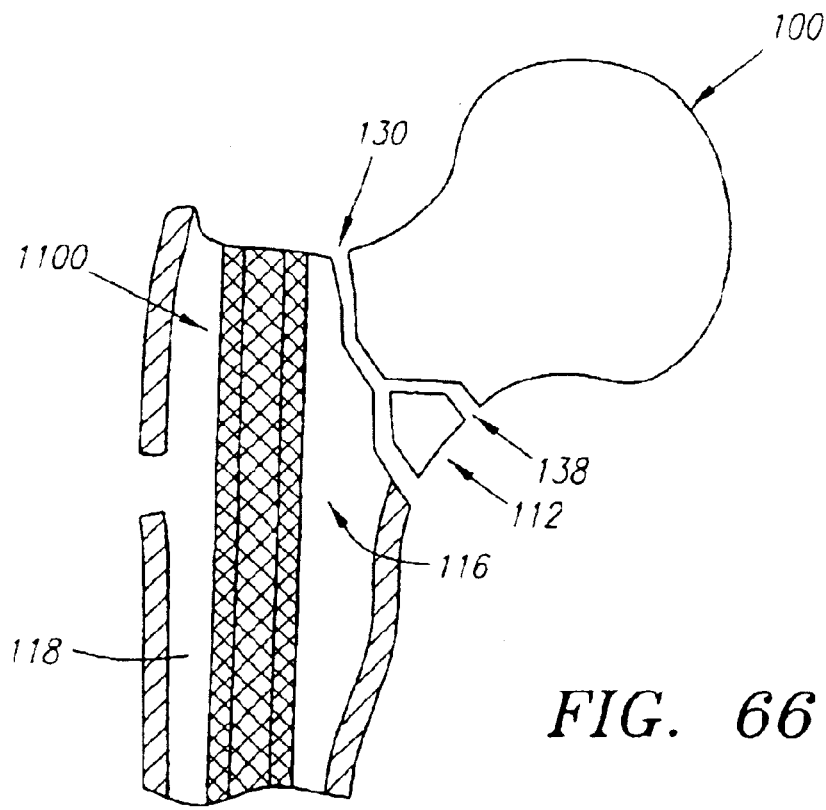
FIG. 66 is a side view of the FIG. 64 device collapsed within a femur having a fractured neck.
Figure 67:
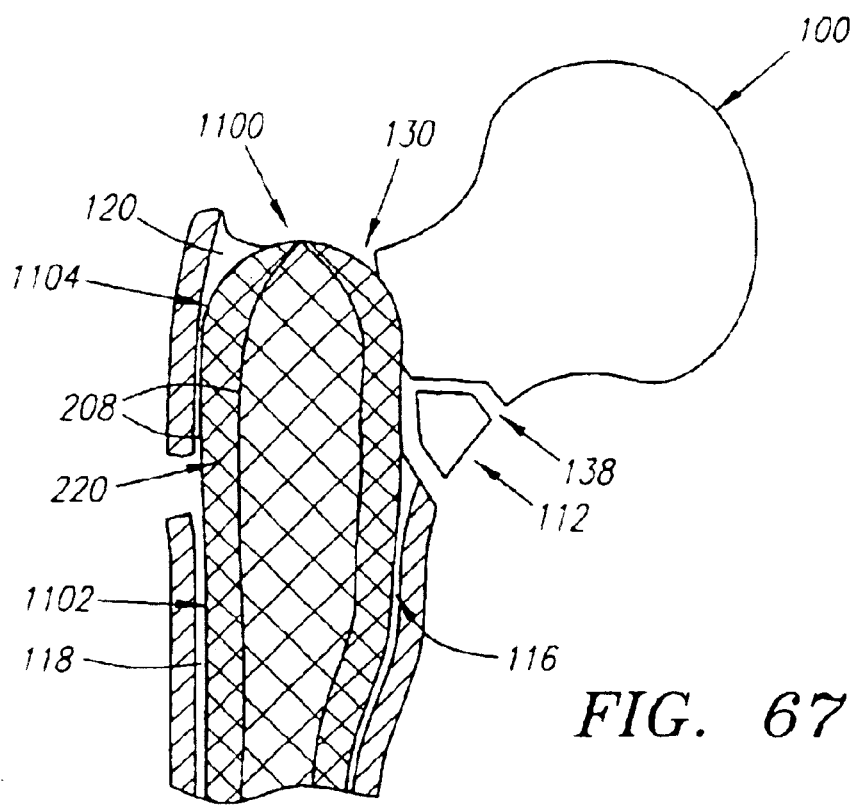
FIG. 67 is a side view of the FIG. 64 device deployed within the fractured femur.

First, the device 1100 is inserted through a previously formed entry portal 130 into the medullary canal 118 (FIG. 66). Once the device 1100 is fully inserted within the medullary canal 118 the device 1100 is deployed by heating the spine elements 208 and mesh 220 to a temperature above the shape transitional temperature of the shape memory alloy (FIG. 67). Of course, if the device 1100 employs means other than heat activation, the device 1100 will be accordingly expanded using these means. As illustrated, the bulbous-shaped proximal end 1104 of the expanded device 1100 adapts to the proximal metaphyseal area 120. Thus, the larger expanded proximal end 1104 firmly engages the walls of the proximal metaphyseal area 120 at a multitude of contact points, while adapting to minute variations within the medullary cavity 116. Additionally, the expanded shaft 1102 firmly engages the walls of the medullary canal 118. If the device 1100 is configured to form a cylindrical shape, the device 100 will, for the most part, firmly engage the walls of the medullary cavity 116 by virtue of the relationship between the shaft 1102 and the medullary canal 118.

Figure 68:
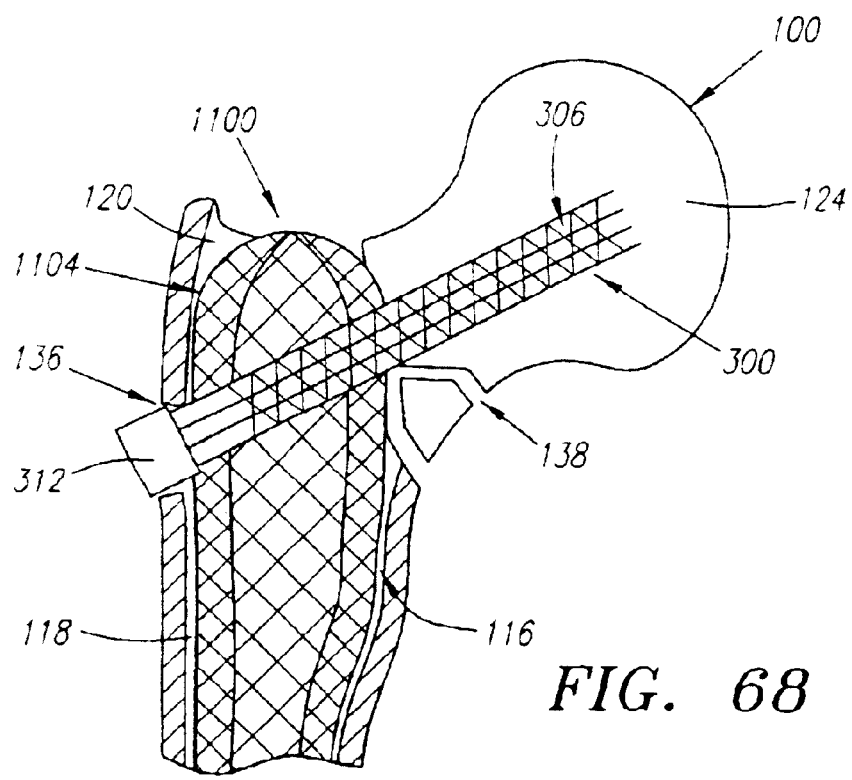
FIG. 68 is a side view of the FIG. 23 device collapsed within the fractured femur and disposed through the proximal end of the deployed FIG. 64 device.

Next, the distal end 306 of the device 300 is inserted through the entry portal 136, through the proximal end 1104 of the device 1100, and into the epiphyseal area 124 of the femur 100 (FIG. 68). The connector 312 is firmly located within the entry portal 136. To facilitate insertion of the device 300 through the device 1100, a channel (not shown) can be formed through the proximal end 1104 of the device 1100. This may not be necessary, however, if the device 1100 does not include an interconnection structure or if the pores of the interconnection structure are large enough for the distal end 306 of the device 300 to pass through.

Figure 69:
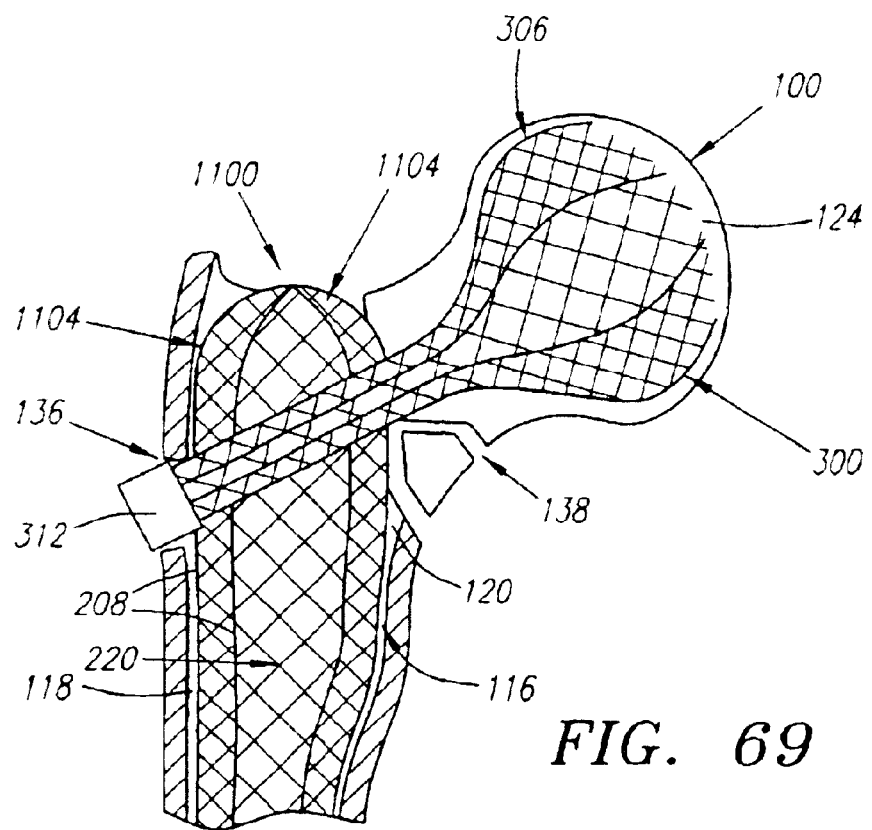
FIG. 69 is a side view of the FIG. 23 device deployed within the fractured femur, wherein the FIG. 23 device is stabilized, in part, by the FIG. 64 device.

Once the device 300 is in position, and the rotational orientation of the fractured femur 100 is confirmed with an image intensifier, the device 300 is deployed within the medullary cavity 116 of the femur 100 by heating the spine elements 208 and mesh 220 to a temperature above the shape transitional temperature of the shape memory alloy (FIG. 69). Of course, if either of the devices 500, 700 or 900 are used in place of the device 300, a different means of deployment will be used.

As illustrated, the trumpet-shaped distal end 306 of the expanded device 300 adapts to the proximal epiphyseal area 124. Thus, the larger expanded distal end 1106 firmly engages the walls of the proximal epiphyseal area 124 at a multitude of contact points, while adapting to minute variations within the medullary cavity 116. Additionally, the proximal end 1104 of the device 1100 firmly engages the shaft 302 of the device 300, thereby providing further stability to the fractured femur 100.

It should be noted that in situations in which the shaft 102, as well as the neck 112, of the femur 100 is fractured, the device 1100 can be made long enough, such that the proximal end 1002 extends past the shaft fracture, preferably into the distal metaphyseal area 126 of the femur 100.

Turning to FIGS. 70 and 71, yet another embodiment of an intramedullary device 1200 is shown that includes a tubular shaft 1202, and proximal and distal ends 1204, 1206 defining a longitudinal axis 1208 therebetween. The tubular shaft 1202 is a generally tubular body, e.g., having a circular or other cross-section. The tubular body may have a solid wall or may have a lattice or other pattern of holes (not shown) formed therein, e.g., for facilitating fluid flow therethrough, for minimizing weight, for providing a desired flexibility, and/or for allowing expansion of the tubular shaft 1202. In an alternative embodiment, the tubular shaft 1202 may include a plurality of axial spine elements interconnected by a mesh or other interconnecting structure, similar to the embodiments described above.

A plurality of splines 1210 extend from the proximal end 1204 and preferably from both the proximal and the distal ends 1204, 1206 of the tubular shaft 1202, as shown. The splines 1210 are expandable between a generally axial collapsed state (shown in FIGS. 70A and 71A) and a substantially transverse expanded state (shown in FIGS. 70B and 71B). The splines 1210 may be substantially flat bands, as shown, round wires, filaments, or other structures capable of assuming the collapsed and expanded states.

As best seen in FIGS. 71A and 71B, each of the splines 1210 includes a first end region 1210a coupled to the tubular shaft 1202 and a second end region 1210b coupled to a collar 1212. The end regions 1210a, 1210b of the splines 1210 may be connected to the tubular shaft 1202 and collar 1212, for example, by hinged joints (not shown). Alternatively, the end regions 1210a, 1210b may be integrally formed with the tubular shaft 1202 and/or collar 1212, and may be sufficiently flexible to bend as needed to accommodate movement between the collapsed and expanded states. Thus, for example, the tubular shaft 1202, splines 1210, and collars 1212 may be formed from a single section of tubing with appropriate material removed using conventional methods to form the splines 1210, as will be appreciated by those skilled in the art.

Each spline 1210 also includes an intermediate region or loop 1210c that may be directed substantially transversely outward with respect to the longitudinal axis 1208 to define the expanded state. In the collapsed state, best seen in FIG. 71A, the first and second end regions 1210a, 1210b of the splines 1210 are generally disposed adjacent one another and extend substantially parallel to the longitudinal axis 1208. The collar 1212 preferably has a diameter substantially smaller than a diameter of the tubular shaft 1202 such that the collar 1212 may be disposed within the splines 1210 in the collapsed state. Thus, the intermediate regions 1210c are generally coextensive with the cross-section of the tubular shaft 1202 in the collapsed state.

In the expanded state, best seen in FIG. 71B, the collar 1212 is displaced axially, i.e., away from the tubular shaft

1202. This action displaces the second end regions 1210*b*, thereby causing the intermediate regions 1210*c* of the splines 1210 to move substantially transversely outward. Thus, in the expanded state, the splines 1210 define a diameter that is substantially greater than the diameter of the tubular shaft 1202.

Figure 72A:
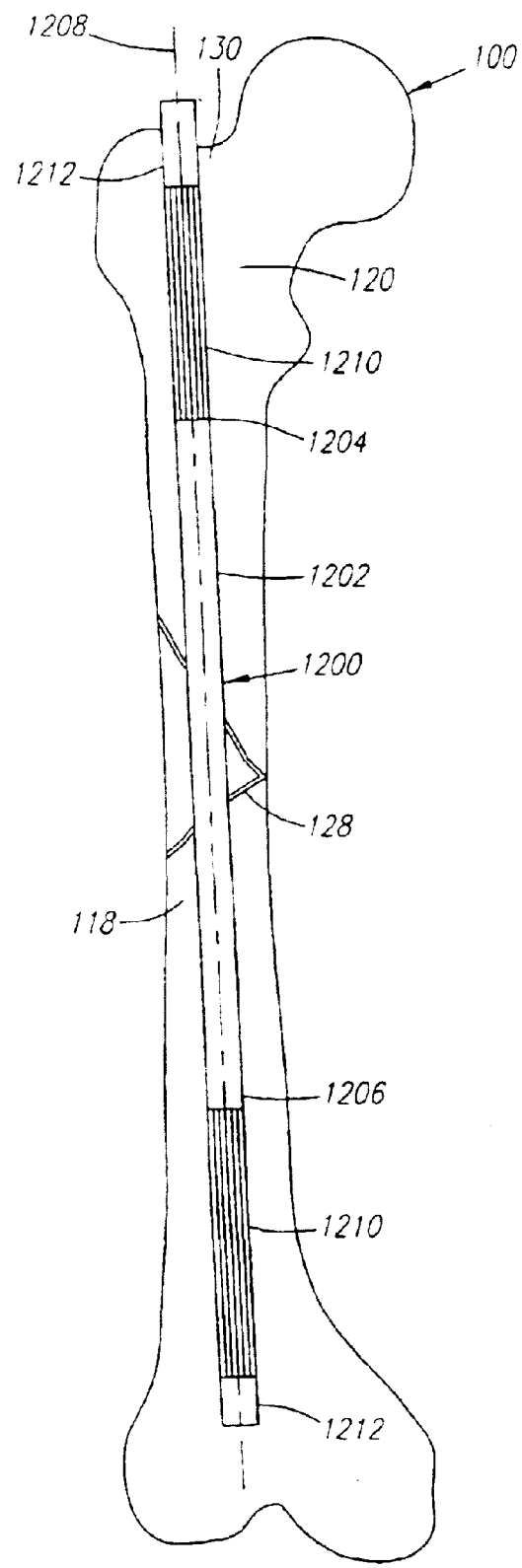
FIGS. 72A and 72B are cross-sectional views of a femur including a fracture being stabilized by the device of FIGS. 70A and 70B.
Figure 72B:
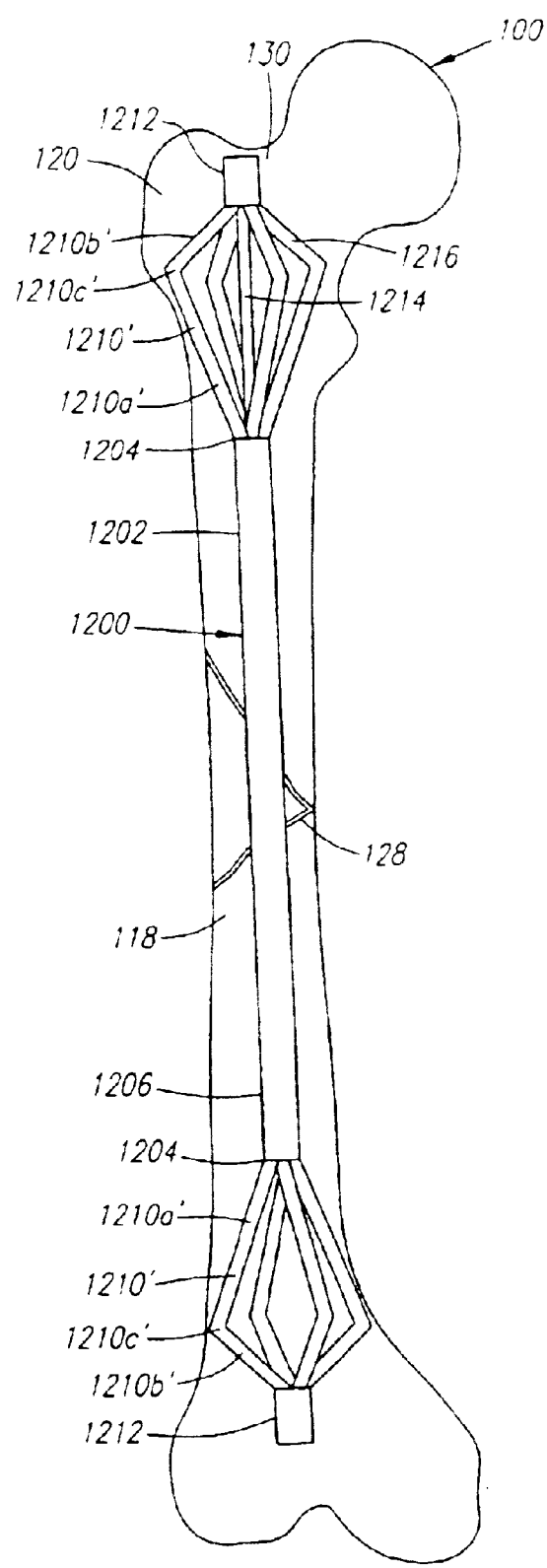

In an alternative embodiment, shown in FIGS. 72A and 72B, the splines 1210' may include first and second end regions 1210*a'*, 1210*b'* and intermediate regions 1210*c'* that are substantially linear in the collapsed state (FIG. 72A). The first end regions 1210*a'* are coupled to the tubular shaft 1202 and the second end regions 1210*b'* are coupled to a collar 1212. The collar 1212 may be displaced axially, i.e., towards the tubular shaft 1202, thereby causing the intermediate regions 1210*c'* to buckle and move substantially transversely outward until they achieve the expanded state (FIG. 72B). The splines 1210' may include scored or thinned regions (not shown) to provide hinges or otherwise ensure that the splines buckle in a predetermined manner, i.e., such that the intermediate regions 1210*c'* move substantially transversely outward.

To cause controlled movement of the collar 1212, and consequently selective expansion and collapse of the splines 1210, the collar 1212 is connected to an actuator (not shown). The actuator is generally disposed within the tubular shaft 1202, and in a preferred embodiment, the actuator includes an elongate control rod 1214 (partially seen in FIG. 72B) and an actuating collar (not shown) disposed within the shaft 1202. The control rod 1214 may be a solid or tubular rod having an outer end 1216 coupled to the collar 1212 and an inner end (not shown) within the tubular shaft 1202. The inner end may have a threaded region for cooperating with a mating threaded region on the actuating collar, similar to the device 800 shown in FIGS. 47 and 48, and described above. As the actuating collar is rotated within the tubular shaft 1202, the control rod is displaced axially within the tubular shaft 1202, thereby displacing the collar 1212 coupled to the splines 1210. Thus, the actuator, via the collar 1212, is coupled to the splines 1210 for selectively expanding the splines 1210 between the collapsed and expanded states.

Alternatively, the actuator may be a control wire (not shown) that is coupled to the collar 1212 and may be pulled, e.g., axially within the tubular shaft 1202, to displace the collar 1212. In this alternative, the splines 1210 may be biased to one of the collapsed and expanded states, which may be overcome by pulling the control wire, e.g., using a tool inserted into the tubular shaft 1202. Other variations may be provided for the actuator, such as mechanical, hydraulic, or pneumatic actuators, as will be appreciated by those skilled in the art.

Turning to FIGS. 72A and 72B, the device 1200 may be deployed within a medullary canal 118 of a fractured femur 100, e.g., having a compound fracture 128. Alternatively, the device 1200 may be deployed in bones other than the femur 100, similar to the embodiments described above. First, the device 1200 may be inserted through a previously formed entry portal 130 into the medullary canal 118 with the splines 1210' collapsed, as shown in FIG. 72A.

Once the device 1200 is fully inserted within the medullary canal 118, a tool (not shown) may be directed through the entry portal 130 and into the tubular shaft 1202 to engage and activate the actuator within the device 1200. For example, the tool may be a drive tool having a rotating head that engages the actuating collar. The drive tool may be pneumatically or electrically driven to rotate the actuating collar, thereby moving the control rod axially within the tubular shaft 1202, and consequently displacing the collar 1212 until the splines 1210 on the proximal end 1204 are expanded. The expanded splines 121 may be sufficiently flexible and/or resilient to adapt to the proximal metaphyseal area 120. Thus, the splines 1212 may firmly engage the walls of the proximal metaphyseal area 120 at a multitude of contact points.

Preferably, the splines 1210 on the distal end 1206 are simultaneously expanded when the splines 1210 on the proximal end 1204 are expanded. Alternatively, the splines 1210 on the distal end 1206 may be independently expanded by a separate actuator, e.g., using a similar tool and method to that described with respect to the proximal end 1204. In a further alternative, an intramedullary device may be provided that includes only a single set of splines, such as the device 1200" shown in FIG. 72B.

After the fracture has healed, the device 1200 may be removed, similar to the embodiments described above. During removal, a tool is generally introduced into the tubular shaft 1202 to engage the actuator and collapse the splines 1210, similar to the method for expanding the splines 1210. In further alternatives, the device 1200 may include an indicator element (not shown) to facilitate removal of the device 1200 and/or the device 1200 may be at least partially composed of a bioabsorbable material, similar to the embodiments described above.

Turning to FIGS. 73 and 74, still another embodiment of an intramedullary device 1300 is shown that includes a tubular shaft 1202, and proximal and distal ends 1304, 1306 defining a longitudinal axis 1308 therebetween. The tubular shaft 1302 is a generally tubular body, e.g., having a circular or other cross-section, similar to the tubular shaft 1210 of the device 1200 described above.

A plurality of splines 1310 extend from the proximal end 1304 and preferably from both the proximal and the distal ends 1304, 1306 of the tubular shaft 1302, as shown. The splines 1310 are expandable between a generally axial collapsed state (shown in FIGS. 73A and 74A) and a substantially transverse expanded state (shown in FIGS. 73B and 74B). The splines 1310 may be substantially flat bands, filaments, or other structures capable of assuming the collapsed and expanded states.

As best seen in FIGS. 73A and 73B, each of the splines 1310 includes a first end region 1310*a* coupled to the tubular shaft 1302 and a second end region 1310*b* that enters the first end region 1310*a* of the tubular shaft 1302. The second end regions 1310*b* of the splines 1310 are coupled to an actuator within the tubular shaft 1302. The first end regions 1310*a* of the splines 1310 may be connected to the tubular shaft 1302, for example, by hinged joints (not shown), or alternatively may be integrally formed with the tubular shaft 1302, similar to the embodiments described above.

Each spline 1310 also includes an intermediate region or loop 1310*c* that may be directed substantially transversely outward with respect to the longitudinal axis 1308 to define the expanded state. In the collapsed state, best seen in FIG. 74A, the first and second end regions 1310*a*, 1310*b* of the splines 1310 are generally disposed adjacent one another and extend substantially parallel to the longitudinal axis 1308, e.g., such that the intermediate regions 1310*c* are generally coextensive with the cross-section of the tubular shaft 1302. In the expanded state, best seen in FIG. 74B, the intermediate regions 1310*c* of the splines 1310 are disposed substantially transversely outward. Thus, in the expanded state, the splines 1310 define a diameter that is substantially greater than the diameter of the tubular shaft 1302.

To cause controlled expansion and collapse of the splines 1310, an actuator (not shown) is generally disposed within the tubular shaft 1302. In a preferred embodiment, the actuator may include a collar (not shown) slidable within the tubular shaft 1302 to which the second end regions 1310*b* are connected. The collar may be controllably displaced axially within the tubular shaft 1302, e.g., using a threaded collar and/or rod arrangement similar to that described above. Thus, the actuator is coupled to the splines 1210 for selectively expanding the splines 1210 between the collapsed and expanded states.

In one embodiment, the splines 1310 may be biased to assume their expanded states, and the collar may be displaced axially, e.g., away from the splines 1310 to pull the second end regions 1310*b* and collapse the splines 1310 to their collapsed states. When the collar is move axially in the opposite direction, e.g., towards the splines 1310, the splines 1310 may be free to expand to the expanded state.

During use, the device 1300 may be deployed within a medullary canal of a fractured bone (not shown), similar to the embodiments described above. The device 1300 may be inserted through a previously formed entry portal into the medullary canal with the splines 1310 collapsed. Once the device 1300 is fully inserted within the medullary canal, a tool (not shown) may be directed through the entry portal and into the tubular shaft 1302 to engage and activate the actuator within the device 1300, i.e., to expand the splines 1210 on the proximal end 1204 to their expanded states. The expanded splines 121 may be sufficiently flexible and/or resilient to adapt to the proximal metaphyseal area and/or to substantially firmly engage the walls of the proximal metaphyseal area at a multitude of contact points.

In one embodiment, the splines 1310 on the distal end 1306 may be simultaneously expanded when the splines 1310 on the proximal end 1304 are expanded. Alternatively, the splines 1310 on the distal end 1306 may be independently expanded by a separate actuator, e.g., using a similar tool and method to that described with respect to the proximal end 1304. In a further alternative, an intramedullary device may be provided that includes only a single set of splines, similar to the embodiments described above.

After the fracture has healed, the device 1300 may be removed, similar to the embodiments described above. During such removal, a tool is generally introduced into the tubular shaft 1302 to engage the actuator and collapse the splines 1310, similar to the method for expanding the splines 1310. In further alternatives, the device 1300 may include an indicator element (not shown) to facilitate removal of the device 1300, and/or the device 1300 may be at least partially composed of a bioabsorbable material, similar to the embodiments described above.

Turning to FIGS. 75A and 75B, another embodiment of an intramedullary device 1400 is shown that includes a tubular shaft 1402, and proximal and distal ends 1404, 1406 defining a longitudinal axis 1408 therebetween, similar to the embodiments described above. A plurality of splines 1410 extend from the proximal end 1404 and preferably from both the proximal and distal ends 1404, 1406 of the tubular shaft 1402, as shown. The splines 1410 are expandable between a generally axial collapsed state (not shown) and a substantially transverse expanded state (shown in FIG. 75B). The splines 1410 may be substantially flat bands, filaments, or other structures having a first end 1410*a* connected to the tubular shaft 1402 and a loose end 1410*b*. Preferably, the splines 1410 are biased to assume the expanded state but may be restrained in the collapsed state by overlying sleeves 1412, that operates similar to the slidable collars described above.

During use, the device 1400 may be deployed within a medullary canal 118 of a fractured femur 100, e.g., having a compound fracture 128. Alternatively, the device 1400 may be deployed in bones other than the femur 100, similar to the embodiments described above. The device 1400 may be inserted through a previously formed entry portal 130 into the medullary canal 118 with the splines 1410 collapsed, as shown in FIG. 75A. Once the device 1400 is fully inserted within the medullary canal 118, the sleeves 1412 may be directed axially to expose and release the splines 1410. Preferably, the splines 1210 automatically expand towards the expanded state, and are sufficiently flexible and/or resilient to adapt to the proximal metaphyseal area 120 and/or firmly engage the walls of the proximal metaphyseal area 120.

After the fracture has healed, the device 1400 may be removed, similar to the embodiments described above. During such removal, a tool is generally introduced to direct the sleeves 1412 back over the splines 1410, similar to the method for expanding the splines 1410. In further alternatives, the device 1400 may include an indicator element (not shown) to facilitate removal of the device 1400.

Any of the devices described herein can be at least partially composed of a bioabsorbable material, a shape memory alloy or polymer, e.g. Nitinol, or other resilient materials, such as stainless steel or a titanium alloy. In addition, similar to the embodiments shown in FIGS. 76A to 77B, an intramedullary device can include a single set of splines that may be used to stabilize a bone fracture, for example, in or adjacent to a neck or other ends of a bone, such as a femur or humerus, or in a hip bone.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

What is claimed is:

1. A device for stabilizing bone, comprising:
a tubular body having first and second end regions defining a longitudinal axis there between,
a first plurality of splines extending from the first end region and expandable between an axial collapsed state and a transverse expanded state,
an actuator movable within the tubular body, the actuator coupled to each spline of the first plurality of splines for selectively expanding the respective splines between the collapsed and expanded state, and
a second plurality of splines extending from the second end region and expandable between an axial collapsed configuration and a transverse expanded configuration, the second plurality of splines coupled to the actuator.

2. The device of claim 1, wherein the actuator comprises a rod coupled to the first plurality of splines, whereby, when the rod is moved axially within the tubular body, an intermediate region of the first plurality of splines is directed substantially transversely outward with respect to the longitudinal axis to define the expanded state.

3. The device of claim 2, wherein each of the first plurality of splines comprises a first end fixed to the first end region of the tubular body, and a second end coupled to a collar, the intermediate region being located between the first and second ends, the rod being coupled to the collar for directing the collar axially, thereby directing the intermediate region substantially transversely outward.

4. The device of claim 3, wherein the first plurality of splines are substantially straight in the collapsed state, and the rod is coupled to the collar for directing the respective second ends towards the first ends, thereby causing the intermediate regions to buckle substantially transversely outward.

5. The device of claim 1, wherein each spline of the first plurality comprises a loop including an outer portion and an inner portion, the outer portion being fixed to the first end region, and the inner portion being coupled to the actuator.

6. The device of claim 5, wherein the actuator is directable towards the first end region, thereby causing the loop to deflect substantially transversely outward.

7. The device of claim 1, wherein the first plurality of splines are biased towards the expanded state, and wherein the actuator comprises a sleeve directable over the first plurality of splines for collapsing them.

8. The device of claim 1, wherein each of the first plurality of splines comprises a first end region coupled to the tubular shaft, and second end region coupled to the actuator.

9. The device of claim 8, wherein the first and second regions extend parallel to the longitudinal axis in the collapsed state.

10. The device of claim 1, wherein the actuator comprises a mechanical actuator, or a hydraulic actuator, or a pneumatic actuator.

* * * * *